(12) United States Patent
Der Sarkissian et al.

(10) Patent No.: US 12,419,849 B2
(45) Date of Patent: *Sep. 23, 2025

(54) REAGENTS, COMPOSITIONS AND METHODS FOR IMPROVING VIABILITY AND FUNCTION OF CELLS, TISSUES AND ORGANS

(71) Applicant: TARGA BIOMEDICAL INC., Montreal (CA)

(72) Inventors: Shant Der Sarkissian, Laval (CA); Nicolas Noiseux, Montreal (CA)

(73) Assignee: TARGA BIOMEDICAL INC., Montreal (CA)

( * ) Notice: Subject to any disclaimer, the term of this patent is extended or adjusted under 35 U.S.C. 154(b) by 0 days.

This patent is subject to a terminal disclaimer.

(21) Appl. No.: 17/870,476

(22) Filed: Jul. 21, 2022

(65) Prior Publication Data

US 2023/0024103 A1 Jan. 26, 2023

Related U.S. Application Data

(63) Continuation of application No. 16/309,474, filed as application No. PCT/CA2017/000151 on Jun. 15, 2017, now Pat. No. 11,446,265.

(Continued)

(51) Int. Cl.
*A61K 31/19* (2006.01)
*A01N 1/125* (2025.01)
(Continued)

(52) U.S. Cl.
CPC ............. *A61K 31/19* (2013.01); *A01N 1/125* (2025.01); *A01N 1/126* (2025.01); *A01N 1/128* (2025.01);
(Continued)

(58) Field of Classification Search
CPC ...... A61K 31/19; A61K 31/16; A61K 31/164; A01N 1/0221; A01N 1/0226; A01N 1/0231; A61P 9/10
See application file for complete search history.

(56) References Cited

U.S. PATENT DOCUMENTS 10,662,218 B2 5/2020 Mazitschek
2010/0209399 A1* 8/2010 Kopyov ................. A61P 19/10
424/93.7

(Continued)

FOREIGN PATENT DOCUMENTS

CN 1276209 A 12/2000
CN 101267779 A 9/2008
(Continued)

OTHER PUBLICATIONS

Nagle DG, Ferreira D, Zhou YD. Epigallocatechin-3-gallate (EGCG): chemical and biomedical perspectives. Phytochemistry. Sep. 2006;67(17):1849-55. doi: 10.1016/j.phytochem.2006.06.020. Epub Jul. 31, 2006. (Year: 2006).*

(Continued)

*Primary Examiner* — Clinton A Brooks
*Assistant Examiner* — Izabela Schmidt
(74) *Attorney, Agent, or Firm* — Smart & Biggar LP; Carmela De Luca

(57) ABSTRACT

Compounds, compositions and methods for improving the viability and/or function of cells or for the in vitro, ex vivo or in vivo protection of cells, tissue, graft or organs from various damages are described. The reagents and composition are based on activation of the heat shock response and/or the antioxidant response and include for example, HSP90 co-factor inhibitor such as Celastrol or Celastrol analogs used alone or in combination with an adjunct agent (e.g., a NRF-2 activator, antioxidant, etc.). Therapeutic enhancement may also include increase in paracrine effector (Continued)

production and signaling. Methods for improving the resistance of cells, tissue, grafts or organs to damages or stress, such as hypoxic or oxidative stress-induced cell death, and/or for improving the viability and retention of transplanted or transfused cells are also described. Therapeutic treatment or prevention of ischemic injury (e.g. myocardial infarct, ischemia/reperfusion injury) and related stressors (hypoxia, oxidative stress, inflammation, sepsis/shock, etc) are also provided.

34 Claims, 35 Drawing Sheets

Related U.S. Application Data

(60) Provisional application No. 62/350,258, filed on Jun. 15, 2016.

(51) Int. Cl.
| | |
|---|---|
| *A01N 1/126* | (2025.01) |
| *A01N 1/128* | (2025.01) |
| *A61K 31/16* | (2006.01) |
| *A61K 31/164* | (2006.01) |
| *A61P 9/10* | (2006.01) |

(52) U.S. Cl.
CPC ............ *A61K 31/16* (2013.01); *A61K 31/164* (2013.01); *A61P 9/10* (2018.01)

(56) References Cited

U.S. PATENT DOCUMENTS

| | | | |
|---|---|---|---|
| 2011/0218143 A1* | 9/2011 | Kaushal .................... | A61P 1/16 514/6.9 |
| 2011/0311508 A1 | 12/2011 | Morimoto | |

FOREIGN PATENT DOCUMENTS

| | | | | |
|---|---|---|---|---|
| CN | 101288671 A | 10/2008 | | |
| CN | 101686951 A | 3/2010 | | |
| CN | 101756956 A | 6/2010 | | |
| CN | 102369014 A | 3/2012 | | |
| CN | 103524592 A * | 1/2014 | | |
| WO | 2007014323 A2 | 2/2007 | | |
| WO | WO-2008013985 A2 * | 1/2008 | ........... | A61K 31/395 |
| WO | WO-2008021210 A2 * | 2/2008 | ........... | A61K 31/155 |
| WO | 2009067245 A1 | 5/2009 | | |
| WO | 2015148802 A1 | 10/2015 | | |

OTHER PUBLICATIONS

Sharma S, Mishra R, Walker BL, Deshmukh S, Zampino M, Patel J, Anamalai M, Simpson D, Singh IS, Kaushal S, Kaushal S. Celastrol, an oral heat shock activator, ameliorates multiple animal disease models of cell death. Cell Stress Chaperones. Jan. 2015;20(1):185-201 (Year: 2015).*
Hyman, A., Simons, K. Beyond HeLa cells. Nature 480, 34 (2011). ttps://doi.org/10.1038/480034a (Year: 2011).*
Andrew J. Boyle, MBBS, PhD , Steven P. Schulman, MD , and Joshua M. Hare, MD, Circulationvol. 114, Issue 4, Jul. 25, 2006; pp. 339-352 (Year: 2006).*
Cypel, M., Neyrinck, A. & Machuca, T.N. Ex vivo perfusion techniques: state of the art and potential applications. Intensive Care Med 45, 354-356 (2019) (Year: 2019).*
Han X, Sun S, Zhao M et al. Celastrol stimulates hypoxia-inducible factor-1activity in tumor cells by initiating the ROS/Akt/p70S6K signaling pathway and enhancing hypoxia-inducible factor-1alpha protein synthesis. PLoSOne 2014; 9: e112470 (Year: 2014).*
S Der Sarkissian, J-F Cailhier, M Borie, L-M Stevens, L Gaboury, S Mansour, P Hamet, N Noiseux Celastrol protects ischaemic myocardium through a heat shock response with up-regulation of haeme oxygenase-1 British Journal of Pharmacology (2014) 171 5265-5279 5265 (Year: 2014).*
Wen-Jian Tang, Jing Wang, Xu Tong, Jing-Bo Shi, Xin-Hua Liu, Jun Li, Design and synthesis of celastrol derivatives as anticancer agents, European Journal of Medicinal Chemistry, vol. 95, 2015, pp. 166-173, ISSN 0223-5234, https://doi.org/10.1016/j.ejmech.2015. 03.039. (Year: 2015).*
Song J, Shi F, Zhang Z, Zhu F, Xue J, Tan X, Zhang L, Jia X. Formulation and evaluation of celastrol-loaded liposomes. Molecules. Sep. 13, 2011;16(9):7880-92. doi: 10.3390/molecules 16097880. PMID: 22143548; PMCID: PMC6264578. (Year: 2011).*
Davenport A, Frezza M, Shen M, Ge Y, Huo C, Chan TH and Dou QP: Celastrol and an EGCG pro-drug exhibit potent chemosensitizing activity in human leukemia cells. Int J Mol Med 25: 465-470, 2010. (Year: 2010).*
Of Van Raemdonck, Dirka,b; Neyrinck, Arnec; Rega, Filipd; Devos, Timothye; Pirenne, Jacquesf. Machine perfusion in organ transplantation: a tool for ex-vivo graft conditioning with mesenchymal stem cells ?. Current Opinion in Organ Transplantation 18(1): p. 24-33, Feb. 2013. (Year: 1013).*
Lada Klaić, Richard I. Morimoto, and Richard B. Silverman, Celastrol Analogues as Inducers of the Heat Shock Response. Design and Synthesis of Affinity Probes for the Identification of Protein Targets ACS Chemical Biology 2012 7 (5), 928-937, (Year: 2012) (Year: 2012).*
Nagle DG, Ferreira D, Zhou YD. Epigallocatechin-3-gallate (EGCG): chemical and biomedical perspectives. Phytochemistry. Sep. 2006;67(17):1849-55. doi: 10.1016/j.phytochem.2006.06.020. Epub Jul. 31, 2006. (Year: 2006) (Year: 2006).*
Sharma S, Mishra R, Walker BL, Deshmukh S, Zampino M, Patel J, Anamalai M, Simpson D, Singh IS, Kaushal S, Kaushal S. Celastrol, an oral heat shock activator, ameliorates multiple animal disease models of cell death. Cell Stress Chaperones. Jan. 2015;20(1):185-201 (Year: 2015) (Year: 2015).*
Hyman, A., Simons, K. Beyond Hela cells. Nature 480, 34 (2011). ttps://doi.org/10.1038/480034a (Year: 2011) (Year: 2011).*
Andrew J. Boyle, MBBS, PhD , Steven p. Schulman, MD , and Joshua M. Hare, MD, Circulationvol. 114, Issue 4, Jul. 25, 2006; pp. 339-352 (Year: 2006) (Year: 2006).*
Cypel, M., Neyrinck, A. & Machuca, T.N. Ex vivo perfusion techniques: state of the art and potential applications. Intensive Care Med 45, 354-356 (2019) (Year: 2019) (Year: 2019).*
Han X, Sun S, Zhao M et al. Celastrol stimulates hypoxia-inducible factor-1activity in tumor cells by initiating the ROS/Akt/p70S6K signaling pathway and enhancing hypoxia-inducible factor-1alpha protein synthesis. PLoSOne 2014; 9: e112470 (Year: 2014) (Year: 2014).*
S Der Sarkissian, J-F Cailhier, M Borie, L-M Stevens, L Gaboury, S Mansour, P Hamet, N Noiseux Celastrol protects ischaemic myocardium through a heat shock response with up-regulation of haeme oxygenase-1 British Journal of Pharmacology (2014) 171 5265-5279 5265 (Year: 2014) (Year: 2014).*
Wen-Jian Tang, Jing Wang, Xu Tong, Jing-Bo Shi, Xin-Hua Liu, Jun Li, Design and synthesis of celastrol derivatives as anticancer agents, European Journal of Medicinal Chemistry, vol. 95, 2015, pp. 166-173, ISSN 0223-5234, https://doi.org/10.1016/j.ejmech.2015. 03.039. (Year: 2015) (Year: 2015).*
Song J, Shi F, Zhang Z, Zhu F, Xue J, Tan X, Zhang L, Jia X. Formulation and evaluation of celastrol-loaded liposomes. Molecules. Sep. 13, 2011;16(9):7880-92. doi: 10.3390/molecules16097880. PMID: 22143548; PMCID: PMC6264578. (Year: 2011) (Year: 2011).*
Davenport A, Frezza M, Shen M, Ge Y, Huo C, Chan TH and Dou QP: Celastrol and an EGCG pro-drug exhibit potent chemosensitizing activity in human leukemia cells. Int J Mol Med 25: 465-470, 2010. (Year: 2010) (Year: 2010).*
Van Raemdonck, Dirka,b; Neyrinck, Arnec; Rega, Filipd; Devos, Timothye; Pirenne, Jacquesf. Machine perfusion in organ transplantation: a tool for ex-vivo graft conditioning with mesenchymal stem cells ?. Current Opinion in Organ Transplantation 18(1): p. 24-33, Feb. 2013. (Year: 1013) (Year: 2013).*

(56) References Cited

OTHER PUBLICATIONS

Edward A. Copelan, Hematopoietic Stem-Cell Transplantation, N Engl J Med 2006;354:1813-26. (Year: 2006).*

Åkerfelt, M., Morimoto, R. & Sistonen, L. Heat shock factors: integrators of cell stress, development and lifespan. Nat Rev Mol Cell Biol 11, 545-555 (2010) (Year: 2010).*

Sánchez-Salinas (Sánchez-Salinas, A., Cabañas-Perianes, V., Blanquer, M., Majado, M.J., Insausti, C.L., Monserrat, J., Sánchez-Ibáñez, M.V., Menchón, P., García-Hernández, A., Gómez-Espuch, J., Morales, A. and Moraleda, J.M. (2012), (Year: 2012).*

Deer EL, González-Hernández J, Coursen JD, Shea JE, Ngatia J, Scaife CL, Firpo MA, Mulvihill SJ. Phenotype and genotype of pancreatic cancer cell lines. Pancreas. May 2010;39(4):425-35) (Year: 2010).*

Lara Planas-Paz, Chantal Pauli, in Principles of Translational Science in Medicine (Third Edition), 2021 (Year: 2021).*

Lada Klaić, Richard I. Morimoto, and Richard B. Silverman, Celastrol Analogues as Inducers of the Heat Shock Response. Design and Synthesis of Affinity Probes for the Identification of Protein Targets ACS Chemical Biology 2012 7 (5), 928-937). (Year: 2012).*

Aceros, H. et al., Celastrol Protects Against Ischemia/Reperfusion-Induced Cardiac Cell Death, Canadian Journal of Cardiology, vol. 31, Issue 10, S4 (Year: 2015).*

Tina Batista Napotnik, Tamara Polajžer, Damijan Miklavičič,Cell death due to electroporation—A review, Bioelectrochemistry, vol. 141, 2021,107871, ISSN 1567-5394 (Year: 2021).*

Der Sarkassian et al., Celastrol protects ischaemic myocardium through a heat shock response with up-regulation of haeme oxygenase-1: Celatrol as a novel drug to treat MI, British Journal of Pharmacology, vol. 171, No. 23, Dec. 2014.

Sharma Sudhish et al. "Celastrol, an oral heat shock activator, ameliorates multiple animal disease models of cell death", Cell Stress and Chaperines, Allen Press Online Publishing, Edinburgh, vol. 20, No. 1, Oct. 2014.

ACEROS "Celastrol protects against ischemia/reperfusioninduced cardiac cell death" Canadian Journal of Cardiology, vol. 31, No. 10, Oct. 2015.

Noiseux et al. Novel infarct sparing drug protects the heart against ischemia-reprefusion (I/R) injury, Journal of the American College of Cardiology, vol. 69, No. 11, Mar. 2017.

Wang et al., "Broad targeting of angiogenesis for cancer prevention and therapy", Seminars in Cancer Biology 35, 2015, S224-S243.

Davenport, Andrew et al., "Celastrol and an EGCG pro-drug exhibit potent chemosensitizing activity in human leukemia cells", International Journal of Molecular Medicine, vol. 25, 2010, 465-470.

Klaic et al., "Celastrol Analogs as Inducers of the Heat Shock Response. Design and Synthesis of Affinity Probes for the indentification of Protein Targets", ACS Chem Biol., 2012, vol. 7. No. 5, pp. 928-937.

Der Sarkassian et al., "Priming of Stem Cells with Celastrol to enheance survival for Cell Therapy", Canadian Journal of Cardiology 28(5), (2012), 532.

Westerheidet et al., "Celastrols as Inducers of the Heat Shock Response and Cytoprotection" The Journal of Biological Chemistry 279(53) (2004), 56053-56060.

Klaic et al., "Remarkable Stereospecific Conjugate Additions to the Hsp90 Inhibitor Celastrol", Journal of the American Chemical Society 133 (2011), 19634-19637.

Naidu et al., Transcription factors Hsf1 and Nrf2 engage in crosstalk for cytoprotection, Trends in Pharmacological Sciences 36(1) (2015), 6-14.

Aceros, Henry et al. Novel heat shock protein 90 inhibitor improves cardiac recovery in a rodent model of donation after circulatory death. The Journal of Thoracic and Cardiovascular Surgery, vol. 163, No. 2, pp. e187-e197.

Nassir, Basil S. et al. HSP90 Inhibitor Improves Lung Protection in Porcine Model of Donation After Circulatory Arrest. Presented at the Fifty-sixth Annual Meeting of The Society of Thoracic Surgeons on Jan. 2020.

Aceros, Henry et al. Celastrol-type HSP90 modulators allow for potent cardioprotective effects. Life Sciences 227 (2019) 8-19.

Huddleson, Charles B. et al. Commentary: You mean there are 89 others? The Journal of Thoracic and Cardiovascular Surgery. Vol. 163, No. 2, pp. e199-e200.

Chambers, David J. Commentary: Heat shock protein 90 inhibition and donor heart protection—a paradoxical concept? The Journal of Thoracic and Cardiovascular Surgery. Vol. 163, No. 2, pp. e201-e202.

Der Sarkissian, Shant et al. Heat shock protein 90 inhibition and multi-target approach to maximize cardioprotection In ischaemic injury. British Journal of Pharmacological Society. 2020; 177, 3378-3388.

Tang, Wen-Jian et al. Design and synthesis of celastrol derivatives as anticancer agents. European Journal of Medicinal Chemistry; 2015, vol. 95, pp. 166-173.

Klaic, Lada et al. Remarkable Stereospecific Conjugate Additions to the Hsp90 Inhibitor Celastrol. Journal of the American Chemical Society. 2011, 133, 19634-19637.

Der Sarkissian, Shant et al. RNA-seq analysis identifies transcriptomic signatures underpinning the therapeutic effeciveness of stem cells in the IMPACT-CABG trial. Presented at the 2017 Till & McCulloch Meetings on Nov. 2017.

Touani, Francesco K. et al. Pharmacological Preconditioning Improves the Viability and Proangiogenic Paracrine Function of Hydrogel-Encapsulated Mesenchymal Stromal Cells. Stem Cells International. vol. 2021, Article ID 6663467.

Der Sarkissian, Shant et al. Optimizing stem cells for cardiac repair: Current status and new frontiers in regenerative cardiology. World J Stem Cells, Jan. 26, 2017; (1); pp. 9-25.

Sharadha, Dayalan Naidu et al. Transcription factors Hsf1 and Nrf2 engage in crosstalk for cytoprotection. Trends in Pharmacological Sciences, Jan. 2015, vol. 36, No. 1.

Foresti, Roberta et al. Small molecule activators of the Nrf2-HO-1 antioxidant axis modulate heme metabolism and inflammation in Bv2 microglia cells. Pharmacological Research, 2013, vol. 76, pp. 132-148.

* cited by examiner

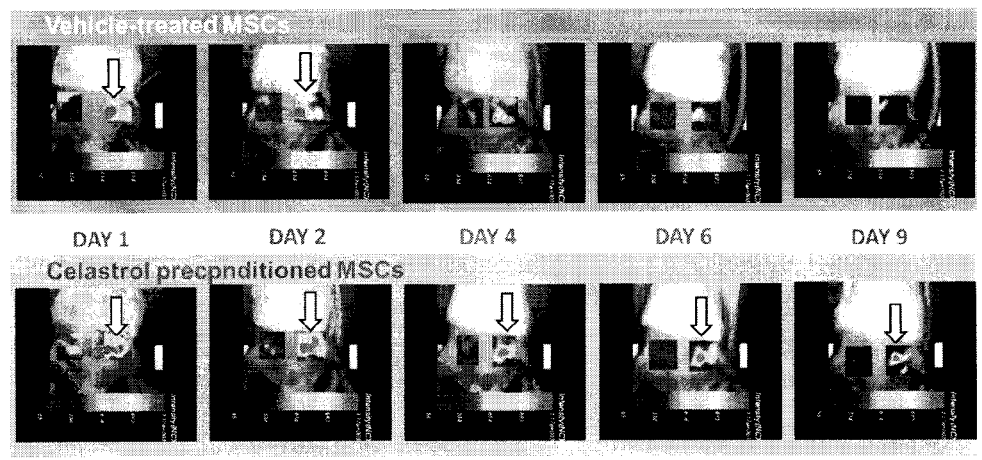
FIG. 2A
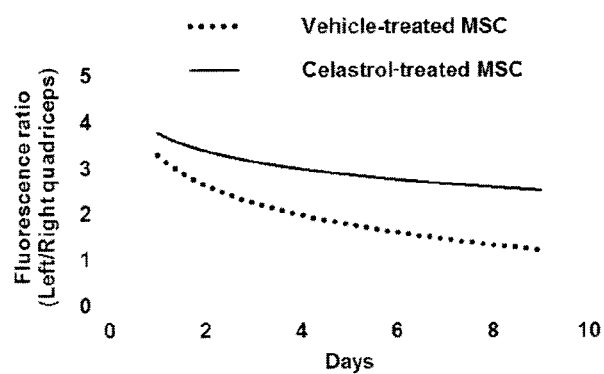
FIG. 2B

|  | Fold-increase |
|---|---|
| Heat shock proteins | |
| HSP90a | 7,0 |
| HSP90b | 2,2 |
| HSP32 (HO-1) | 2,2 |
| HSP70 | 1,8 |
| Growth factors and cytokines | |
| MCSF | 24,4 |
| HGF | 2,1 |
| Antioxidants | |
| GST | 2,8 |
| Thioredoxin | 2,5 |
| Catalase | 1,7 |

| TREATMENTS | VIABILITY; LIVE / DEAD | |
|---|---|---|
| | Paracrine mediator | |
| | Perconditioning H9c2 Hypoxic stress | Pre-conditioning H9c2 Oxidative stress |
| Radicicol 1uM | ≠ | xxx |
| Celastrol 1uM | ✓✓ | x |
| Gedunin 1uM | ≠ | ✓✓ |
| EGCG 1uM | | |
| EGCG 10uM | ≠ | ✓ |
| tBHQ 1uM | | |
| tBHQ 5uM | ≠ | ✓✓ |
| Celastrol 1uM + EGCG 1uM | | |
| Celastrol 1uM + EGCG 10uM | | |
| Celastrol 1uM + tBHQ 1uM | | |
| Celastrol 1uM + tBHQ 5uM | | ✓✓ |
| Gedunin 1uM + EGCG 1uM | | |
| Gedunin 1uM + EGCG 10uM | | ✓✓✓ |
| Gedunin 1uM + tBHQ 1uM | | |
| Gedunin 1uM + tBHQ 5uM | | |

FIG. 22B

A) Celastrol
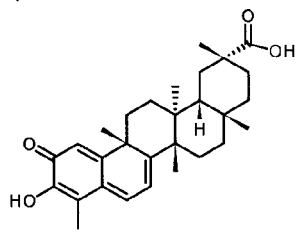
B) Dihydrocelastrol
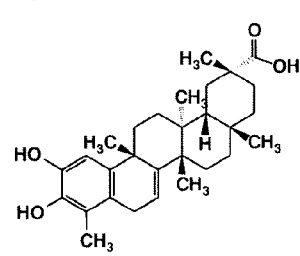
C) Analog 1
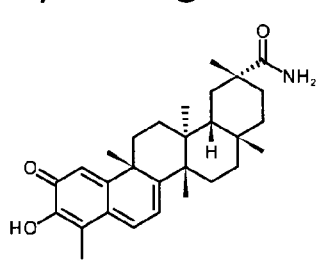
D) Analog 2
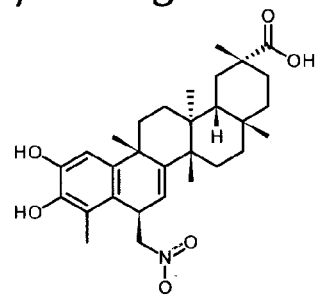
E) Analog 3
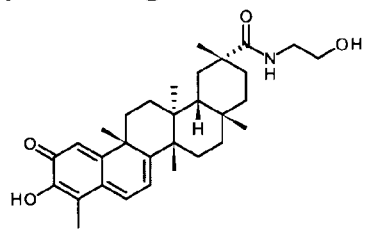
F) Analog 4
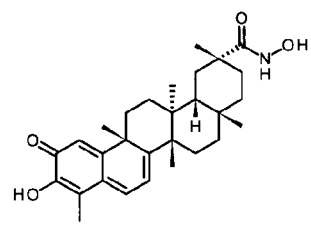
G) Analog 5
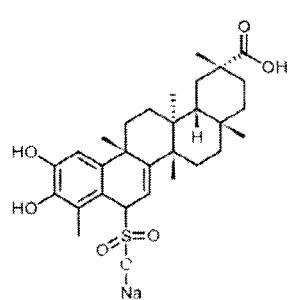
H) Analog 6
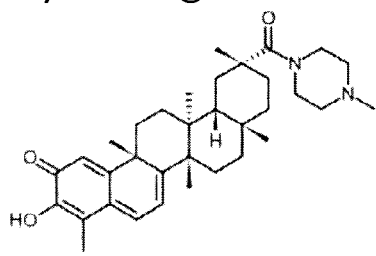
FIG. 23

Adjunct co-treatments with some main related functions

Co-treatments

| | |
|---|---|
| 2HBA | Antioxidant; synthetic analog of curcumin |
| Andrographolide | Inhibitor of NF-κB signaling |
| Ascorbic Acid | Antioxidant; reducing agent |
| Cafestol | Antioxidant |
| Carnosol | Antioxidant |
| CDDO-im | Antioxidant |
| Chalcone | Antioxidant; open chain flavanois; inhibitor of fatty acid synthase and α-amylase |
| CHIR98014 | WNT pathway activator; Inhibits GSK3α and GSK3β |
| Conglobatin | Macrolide dilactone; immunosupressor |
| Curcumin | Antioxidant |
| Cycloastragenol | Telomerase activator |
| 1,2-dithiole-3-thione (D3T) | Antioxidant |
| Doramapimod | Pan-p38 MAPK inhibitor |
| Edaravone | Antioxidant; neuroprotective agent |
| EGCG | Antioxidant |
| Gambogic acid | Anticancer agent; apoptosis inducer |
| Ganetespib | HSP90 inhibitor |
| Gedunin | HSP90 inhibitor; cofactor inhibitor |
| IQ-1 | WNT pathway activator; inhibits protein phosphatase PP2A |
| Limonin | Gedunin analog; HSP90 inhibitor |
| Lonidamide | Anticancer agent; glycolysis inhibitor |
| Melatonin | Endogenous hormone |
| N1016 | HSP90 inhibitor; cytoplasmic inhibitor |
| N886 | HSP90 inhibitor; cofactor inhibitor |
| N997 | Novobiocin analog; HSP90 inhibitor |
| Novobiocin | Aminocoumarin antibiotic; HSP90 inhibitor |
| Pyridoxal 5'-phosphate (P5'-P) | Antioxidant; active form of Vitamin B6 |
| Pyrithione | Antifungal agent |
| Quercetin | Antioxidant |
| Radicicol | HSP90 inhibitor; N-terminal region |
| Resveratrol | Antioxidant; COX-1 inhibitor |
| RTA-408 | Antioxidant |
| SB202190 | p38 MAPK inhibitor |
| SB216763 | WNT pathway activator; inhibits GSK3α and GSK3β |
| SNX-5422 | HSP90 inhibitor; Hsp90α and Hsp90β |
| Sodium Butyrate | Epigenetic modifier; inhibits histone deacetylase |
| Sulforane | Antioxidant; HDAC I and II inhibitor with anticancer activity |
| Tetrabromobenzotriazole (TBB) | Casein kinase 2 inhibitor |
| tert-Butylhydroquinone (tBHQ) | Antioxidant; inhibitor of endoplasmic reticulum Ca2+-ATPase |
| Valproic Acid | Epigenetic modifier; inhibits HDAC I; Epilepsy and bipolar disorder medication |
| Withaferin A | Antioxidant; NF-κB inhibitor |

FIG. 24

|  | HO1 | FGF2 | HSP70 | VEGFa | SDF1 | HGF | IGF-1 | IL-6 |
|---|---|---|---|---|---|---|---|---|
| Celastrol (1uM) | 25.96 | 1.30 | 40.57 | 1.34 | 1.72 | 0.75 | 0.93 | 0.40 |
| Celastrol (1uM) + Ascorbic Acid (1uM) | 38.69 |  | 18.24 | 1.50 |  |  |  |  |
| Celastrol (1uM) + Chalcone (1uM) | 27.91 | 0.94 |  |  |  |  |  |  |
| Celastrol (1uM) + CHIR98014 (1uM) | 33.06 |  |  | 1.20 |  |  |  |  |
| Celastrol (1uM) + Cycloastragenol (1uM) | 26.84 | 1.07 | 12.65 | 1.39 |  |  |  |  |
| Celastrol (1uM) + Doramapimod (1uM) | 25.24 |  |  | 1.24 |  |  |  |  |
| Celastrol (1uM) + Edavarone (1uM) | 27.33 | 1.28 | 19.71 |  |  |  |  |  |
| Celastrol (1uM) + Gambogic acid (1uM) | 69.40 | 1.16 | 91.60 | 1.58 |  |  |  |  |
| Celastrol (1uM) + IQ-1 (1uM) | 18.81 |  |  | 0.56 |  |  |  |  |
| Celastrol (1uM) + Lonidamine (1uM) | 30.58 | 1.27 | 17.35 |  |  |  |  |  |
| Celastrol (1uM) + N0886 (1uM) | 20.12 | 1.01 | 12.67 |  |  |  |  |  |
| Celastrol (1uM) + N0997 (1uM) | 23.67 | 0.97 | 11.96 |  |  |  |  |  |
| Celastrol (1uM) + N955 (1uM) | 32.65 | 1.18 |  | 1.30 |  |  |  |  |
| Celastrol (1uM) + P5'-P (1uM) | 19.69 | 0.94 |  | 0.85 |  |  |  |  |
| Celastrol (1uM) + SB202190 (1uM) | 32.67 |  |  | 1.10 |  |  |  |  |
| Celastrol (1uM) + SB216763 (1uM) | 30.94 |  |  | 1.09 |  |  |  |  |
| Celastrol (1uM) + SNX-5422 -CP2 (1uM) | 25.39 |  | 24.54 |  |  |  |  |  |
| Celastrol (1uM) + Sodium Butyrate (1uM) | 33.17 |  |  | 1.18 |  |  |  |  |
| Celastrol (1uM) + TBB (1uM) | 38.33 |  |  | 1.23 |  |  |  |  |
| Celastrol (1uM) + Valporic Acid (1uM) | 42.48 |  |  | 1.20 |  |  |  |  |
| Celastrol (1uM) + 2HBA (1uM) | 63.80 | 1.45 | 45.47 | 1.93 | 1.74 | 0.72 | 0.49 | 0.16 |
| Celastrol (1uM) + Andrographolide (1uM) | 33.03 | 1.35 | 13.32 | 1.55 |  |  |  |  |
| Celastrol (1uM) + Cafestol (1uM) | 18.77 | 0.90 | 16.52 | 1.32 |  |  |  |  |
| Celastrol (1uM) + Carnosol (1uM) | 28.84 | 1.31 | 14.86 |  | 1.83 | 0.99 | 0.98 | 0.35 |
| Celastrol (1uM) + Conglobatin -CP4 (1uM) | 22.66 | 0.95 | 15.09 |  |  |  |  |  |
| Celastrol (1uM) + Curcumin (1uM) | 30.35 | 1.45 | 17.96 | 1.88 | 2.10 | 1.04 | 1.21 | 0.36 |
| Celastrol (1uM) + D3T (1uM) | 25.29 | 0.98 | 18.63 |  |  |  |  |  |
| Celastrol (1uM) + EGCG (10uM) | 37.62 |  | 106.26 |  |  |  |  |  |
| Celastrol (1uM) + EGCG (1uM) | 25.30 | 1.21 | 50.77 | 1.12 | 1.98 | 0.78 | 0.94 | 0.32 |
| Celastrol (1uM) + Ganetspib -CP6 (1uM) | 33.07 | 1.41 | 37.82 | 0.93 |  |  |  |  |
| Celastrol (1uM) + Melatonin (1uM) | 30.92 |  |  | 1.21 |  |  |  |  |
| Celastrol (1uM) + N1016 (1uM) | 26.14 | 1.14 | 36.09 |  |  |  |  |  |
| Celastrol (1uM) + Novobiocin (1uM) | 35.12 | 1.45 | 20.69 | 1.28 |  |  |  |  |
| Celastrol (1uM) + Pyrithione (1uM) | 24.95 | 1.09 | 12.15 | 1.07 |  |  |  |  |
| Celastrol (1uM) + Quercetin (1uM) | 30.08 | 1.31 | 16.27 | 1.13 |  |  |  |  |
| Celastrol (1uM) + Radicicol -CP7 (1uM) | 34.67 | 1.01 | 28.48 |  |  |  |  |  |
| Celastrol (1uM) + Resveratrol (1uM) | 25.77 | 1.14 | 16.01 | 1.23 |  |  |  |  |
| Celastrol (1uM) + Sulforane (1uM) | 30.19 | 1.12 | 19.81 | 0.90 |  |  |  |  |
| Celastrol (1uM) + tBHQ (1uM) | 26.31 | 1.38 | 16.72 | 1.58 | 3.20 | 1.41 | 1.33 | 0.48 |
| Celastrol (1uM) + tBHQ (5uM) | 31.19 |  | 63.77 |  |  |  |  |  |

FIG. 25A

|  | HO1 | FGF2 | HSP70 | VEGFa | SDF1 | HGF | IGF-1 | IL-6 |
| --- | --- | --- | --- | --- | --- | --- | --- | --- |
| Celastrol (1uM) | 25,96 | 1,30 | 40,57 | 1,34 | 1,72 | 0,75 | 0,93 | 0,40 |
| 2HBA (1uM) | 27,52 | 1,01 |  | 0,94 | 1,13 | 0,58 | 0,54 | 0,37 |
| Carnosol (1uM) | 3,89 | 1,45 |  | 1,64 | 1,89 | 1,33 | 0,76 | 1,14 |
| Curcumin (1uM) | 2,97 | 1,38 |  | 1,82 | 2,05 | 1,29 | 1,14 | 1,32 |
| EGCG (1uM) | 1,14 | 1,20 | 1,04 | 1,19 | 1,57 | 1,26 | 1,11 | 1,02 |
| tBHQ (1uM) | 2,13 | 1,40 |  | 1,51 | 1,92 | 1,65 | 0,92 | 1,16 |
| Celastrol (1uM) + 2HBA (1uM) | 63,80 | 1,45 | 45,47 | 1,93 | 1,74 | 0,72 | 0,49 | 0,16 |
| Celastrol (1uM) + Carnosol (1uM) | 28,84 | 1,31 | 14,86 |  | 1,83 | 0,99 | 0,98 | 0,35 |
| Celastrol (1uM) + Curcumin (1uM) | 30,35 | 1,45 | 17,96 | 1,88 | 2,10 | 1,04 | 1,21 | 0,36 |
| Celastrol (1uM) + EGCG (1uM) | 25,30 | 1,21 | 50,77 | 1,12 | 1,98 | 0,78 | 0,94 | 0,32 |
| Celastrol (1uM) + tBHQ (1uM) | 26,31 | 1,38 | 16,72 | 1,58 | 3,20 | 1,41 | 1,33 | 0,48 |

|  | HO1 | FGF2 | HSP70 | VEGFa | SDF1 | HGF | IGF-1 | IL-6 |
| --- | --- | --- | --- | --- | --- | --- | --- | --- |
| Dihydrocelastrol (1uM) | 6,11 | 1,26 |  | 1,62 | 1,96 | 1,24 | 1,29 | 0,56 |
| 2HBA (1uM) | 27,52 | 1,01 |  | 0,94 | 1,13 | 0,58 | 0,54 | 0,37 |
| Carnosol (1uM) | 3,89 | 1,45 |  | 1,64 | 1,89 | 1,33 | 0,76 | 1,14 |
| Curcumin (1uM) | 2,97 | 1,38 |  | 1,82 | 2,05 | 1,29 | 1,14 | 1,32 |
| EGCG (1uM) | 1,14 | 1,20 | 1,04 | 1,19 | 1,57 | 1,26 | 1,11 | 1,02 |
| tBHQ (1uM) | 2,13 | 1,40 |  | 1,51 | 1,92 | 1,65 | 0,92 | 1,16 |
| Dihydrocelastrol (1uM) + 2HBA (1uM) | 33,82 | 1,13 |  | 1,70 | 2,36 | 0,84 | 0,56 | 0,21 |
| Dihydrocelastrol (1uM) + Carnosol (1uM) | 3,95 | 1,02 |  | 1,72 | 1,89 | 0,86 | 1,25 | 0,48 |
| Dihydrocelastrol (1uM) + Curcumin (1uM) | 3,85 | 1,27 |  | 2,17 | 2,41 | 1,04 | 1,78 | 0,80 |
| Dihydrocelastrol (1uM) + EGCG (1uM) | 2,14 | 1,14 |  | 2,12 | 2,61 | 1,62 | 1,78 | 0,77 |
| Dihydrocelastrol (1uM) + tBHQ (1uM) | 2,88 | 0,98 |  | 1,62 | 2,25 | 1,13 | 1,55 | 0,64 |

|  | HO1 | FGF2 | HSP70 | VEGFa | SDF1 | HGF | IGF-1 | IL-6 |
| --- | --- | --- | --- | --- | --- | --- | --- | --- |
| Analog 1 (1uM) | 33,78 | 1,36 |  | 1,52 | 1,82 | 0,86 | 0,80 | 0,32 |
| 2HBA (1uM) | 27,52 | 1,01 |  | 0,94 | 1,13 | 0,58 | 0,54 | 0,37 |
| Carnosol (1uM) | 3,89 | 1,45 |  | 1,64 | 1,89 | 1,33 | 0,76 | 1,14 |
| Curcumin (1uM) | 2,97 | 1,38 |  | 1,82 | 2,05 | 1,29 | 1,14 | 1,32 |
| EGCG (1uM) | 1,14 | 1,20 | 1,04 | 1,19 | 1,57 | 1,26 | 1,11 | 1,02 |
| tBHQ (1uM) | 2,13 | 1,40 |  | 1,51 | 1,92 | 1,65 | 0,92 | 1,16 |
| Analog 1 (1uM) + 2HBA (1uM) | 41,76 | 1,41 |  | 2,64 | 2,25 | 0,99 | 0,58 | 0,26 |
| Analog 1 (1uM) + Carnosol (1uM) | 32,63 | 1,31 |  | 1,10 | 1,75 | 0,93 | 1,12 | 0,27 |
| Analog 1 (1uM) + Curcumin (1uM) | 36,48 | 1,53 |  | 1,96 | 2,45 | 1,17 | 1,13 | 0,46 |
| Analog 1 (1uM) + EGCG (1uM) | 36,72 | 1,38 |  | 2,15 | 2,52 | 1,10 | 1,13 | 0,39 |
| Analog 1 (1uM) + tBHQ (1uM) | 35,43 | 1,29 |  | 1,56 | 2,29 | 1,01 | 1,11 | 0,33 |

|  | HO1 | FGF2 | HSP70 | VEGFa | SDF1 | HGF | IGF-1 | IL-6 |
| --- | --- | --- | --- | --- | --- | --- | --- | --- |
| Analog 3 (1uM) | 44,75 | 1,74 |  | 1,80 | 1,30 | 0,84 | 0,41 | 0,49 |
| 2HBA (1uM) | 27,52 | 1,01 |  | 0,94 | 1,13 | 0,58 | 0,54 | 0,37 |
| Carnosol (1uM) | 3,89 | 1,45 |  | 1,64 | 1,89 | 1,33 | 0,76 | 1,14 |
| Curcumin (1uM) | 2,97 | 1,38 |  | 1,82 | 2,05 | 1,29 | 1,14 | 1,32 |
| EGCG (1uM) | 1,14 | 1,20 | 1,04 | 1,19 | 1,57 | 1,26 | 1,11 | 1,02 |
| tBHQ (1uM) | 2,13 | 1,40 |  | 1,51 | 1,92 | 1,65 | 0,92 | 1,16 |
| Analog 3 (1uM) + 2HBA (1uM) | 30,21 | 2,03 |  | 3,04 | 2,03 | 1,34 | 0,54 | 0,59 |
| Analog 3 (1uM) + Carnosol (1uM) | 34,16 | 2,41 |  | 3,58 | 2,41 | 1,34 | 0,40 | 0,75 |
| Analog 3 (1uM) + Curcumin (1uM) | 29,84 | 2,15 |  | 3,13 | 2,15 | 1,19 | 0,48 | 0,65 |
| Analog 3 (1uM) + EGCG (1uM) | 24,13 | 1,95 |  | 2,94 | 1,71 | 0,94 | 0,46 | 0,60 |
| Analog 3 (1uM) + tBHQ (1uM) | 28,41 | 2,54 |  | 3,94 | 2,23 | 1,20 | 0,53 | 0,85 |

| Protein of interest | Combination treatment | Fold change | Synergistic or additive combination | Angiogenic expression index |
|---|---|---|---|---|
| FGF2 | Analog 3 (1uM) + tBHQ (1uM) | 2.5 | s | 17.4 |
| VEGF | Analog 3 (1uM) + tBHQ (1uM) | 3.9 | s | |
| SDF1 | Analog 3 (1uM) + tBHQ (1uM) | 2.2 | A | |
| HO1 | Analog 3 (1uM) + Carnosol (1uM) | 34.2 | | 16.8 |
| FGF2 | Analog 3 (1uM) + Carnosol (1uM) | 2.4 | s | |
| VEGF | Analog 3 (1uM) + Carnosol (1uM) | 3.6 | s | |
| SDF1 | Analog 3 (1uM) + Carnosol (1uM) | 2.4 | s | |
| HO1 | Analog 3 (1uM) + Curcumin (1uM) | 29.8 | | 14.9 |
| FGF2 | Analog 3 (1uM) + Curcumin (1uM) | 2.2 | s | |
| VEGF | Analog 3 (1uM) + Curcumin (1uM) | 3.1 | s | |
| SDF1 | Analog 3 (1uM) + Curcumin (1uM) | 2.2 | s | |
| HO1 | Analog 3 (1uM) + 2HBA (1uM) | 30.2 | | 14.2 |
| FGF2 | Analog 3 (1uM) + 2HBA (1uM) | 2.0 | s | |
| VEGF | Analog 3 (1uM) + 2HBA (1uM) | 3.0 | s | |
| SDF1 | Analog 3 (1uM) + 2HBA (1uM) | 2.0 | s | |
| FGF2 | Analog 3 (1uM) + EGCG (1uM) | 2.0 | s | 13.2 |
| VEGF | Analog 3 (1uM) + EGCG (1uM) | 2.9 | s | |
| SDF1 | Analog 3 (1uM) + EGCG (1uM) | 1.7 | A | |

FIG. 26B

| Protein of interest | Combination treatment | Fold change | Synergistic or additive combination | Angiogenic expression index |
|---|---|---|---|---|
| HO1 | Celastrol (1uM) + Curcumin (1uM) | 30.3 | A | 8.0 |
| VEGF | Celastrol (1uM) + Curcumin (1uM) | 1.9 | a | |
| SDF1 | Celastrol (1uM) + Curcumin (1uM) | 2.1 | a | |
| IL6 | Celastrol (1uM) + Curcumin (1uM) | 0.4 | a | |
| VEGF | Celastrol (1uM) + 2HBA (1uM) | 1.9 | s | 7.3 |
| SDF1 | Celastrol (1uM) + 2HBA (1uM) | 1.7 | | |
| IL6 | Celastrol (1uM) + 2HBA (1uM) | 0.2 | | |
| VEGF | Dihydrocelastrol (1uM) + Carnosol (1uM) | 1.7 | a | 7.2 |
| SDF1 | Dihydrocelastrol (1uM) + Carnosol (1uM) | 1.9 | | |
| IL6 | Dihydrocelastrol (1uM) + Carnosol (1uM) | 0.5 | A | |
| HSP70 | Celastrol (1uM) + EGCG (1uM) | 50.8 | s | 4.0 |
| SDF1 | Celastrol (1uM) + EGCG (1uM) | 2.0 | a | |
| IL6 | Celastrol (1uM) + EGCG (1uM) | 0.3 | s | |
| HO1 | Celastrol (1uM) + Carnosol (1uM) | 28.8 | s | 3.7 |
| SDF1 | Celastrol (1uM) + Carnosol (1uM) | 1.8 | a | |
| IL6 | Celastrol (1uM) + Carnosol (1uM) | 0.3 | s | |
| HO1 | Analog 1 (1uM) + Carnosol (1uM) | 32.6 | s | 3.5 |
| SDF1 | Analog 1 (1uM) + Carnosol (1uM) | 1.7 | | |
| IL6 | Analog 1 (1uM) + Carnosol (1uM) | 0.3 | A | |

| Protein of interest | Combination treatment | Fold change | Synergistic or additive combination | Angiogenic expression index |
|---|---|---|---|---|
| VEGF | Dihydrocelastrol (1uM) + EGCG (1uM) | 2.1 | s | 12.9 |
| SDF1 | Dihydrocelastrol (1uM) + EGCG (1uM) | 2.6 | s | |
| HGF | Dihydrocelastrol (1uM) + EGCG (1uM) | 1.6 | s | |
| IGF1 | Dihydrocelastrol (1uM) + EGCG (1uM) | 1.8 | s | |
| HO1 | Analog 1 (1uM) + Curcumin (1uM) | 36.5 | | 11.9 |
| FGF2 | Analog 1 (1uM) + Curcumin (1uM) | 1.5 | a | |
| VEGF | Analog 1 (1uM) + Curcumin (1uM) | 2.0 | a | |
| SDF1 | Analog 1 (1uM) + Curcumin (1uM) | 2.5 | a | |
| IL6 | Analog 1 (1uM) + Curcumin (1uM) | 0.5 | | |
| VEGF | Dihydrocelastrol (1eM) + Curcumin (1uM) | 2.2 | s | 10.9 |
| SDF1 | Dihydrocelastrol (1uM) + Curcumin (1uM) | 2.4 | a | |
| IGF1 | Dihydrocelastrol (1uM) + Curcumin (1uM) | 1.8 | s | |
| HO1 | Analog 1 (1uM) + 2HBA (1uM) | 41.8 | | 9.8 |
| VEGF | Analog 1 (1uM) + 2HBA (1uM) | 2.6 | s | |
| SDF1 | Analog 1 (1uM) + 2HBA (1uM) | 2.3 | s | |
| IL6 | Analog 1 (1uM) + 2HBA (1uM) | 0.3 | a | |
| VEGF | Celastrol (1uM) + tBHQ (1uM) | 1.6 | a | 9.6 |
| SDF1 | Celastrol (1uM) + tBHQ (1uM) | 3.2 | s | |
| IL6 | Celastrol (1uM) + tBHQ (1uM) | 0.5 | | |
| VEGF | Dihydrocelastrol (1uM) + tBHQ (1uM) | 1.6 | A | 9.3 |
| SDF1 | Dihydrocelastrol (1uM) + tBHQ (1uM) | 2.3 | a | |
| IGF1 | Dihydrocelastrol (1uM) + tBHQ (1uM) | 1.5 | s | |
| HO1 | Analog 1 (1uM) + EGCG (1uM) | 36.7 | s | 9.3 |
| VEGF | Analog 1 (1uM) + EGCG (1uM) | 2.1 | s | |
| SDF1 | Analog 1 (1uM) + EGCG (1uM) | 2.5 | s | |
| IL6 | Analog 1 (1uM) + EGCG (1uM) | 0.4 | | |
| HO1 | Dihydrocelastrol (1uM) + 2HBA (1uM) | 33.8 | A | 8.1 |
| VEGF | Dihydrocelastrol (1uM) + 2HBA (1uM) | 1.7 | s | |
| SDF1 | Dihydrocelastrol (1uM) + 2HBA (1uM) | 2.4 | s | |
| IL6 | Dihydrocelastrol (1uM) + 2HBA (1uM) | 0.2 | A | |

FIG. 26C

|  |  | NORMOXIA | | HYPOXIA | |
|---|---|---|---|---|---|
|  |  | Celastrol (1uM) | Celastrol (1uM) + 2HBA (1uM) | Celastrol (1uM) | Celastrol (1uM) + 2HBA (1uM) |
|  |  | avg     sem | avg     sem | avg     sem | avg     sem |
| Antioxidants | HMOX1 | 1,54 ± 0,11 | 1,82 ± 0,08 | 6,47 ± 0,33 | 7,90 ± 0,70 |
|  | NQO1 | 1,63 ± 0,12 | 2,10 ± 0,09 | 2,43 ± 0,13 | 3,89 ± 0,35 |
|  | SOD1 | 1,36 ± 0,10 | 1,12 ± 0,05 | 1,47 ± 0,08 | 1,81 ± 0,16 |
|  | GSR | 1,10 ± 0,08 | 1,06 ± 0,05 | 1,39 ± 0,07 | 1,57 ± 0,14 |
| Growth factors | VEGFA | 0,77 ± 0,05 | 1,72 ± 0,07 | 0,23 ± 0,01 | 7,58 ± 0,68 |
|  | FGF2 | 0,87 ± 0,06 | 1,37 ± 0,06 | 2,03 ± 0,10 | 7,20 ± 0,64 |
|  | TGFB1 | 0,84 ± 0,06 | 1,11 ± 0,05 | 0,52 ± 0,03 | 2,26 ± 0,20 |
|  | PDGFA | 0,79 ± 0,06 | 0,93 ± 0,04 | 1,37 ± 0,07 | 8,93 ± 0,80 |
|  | PDGFB | 1,91 ± 0,14 | 3,57 ± 0,15 | 0,60 ± 0,03 | 1,29 ± 0,11 |
| Tissue and matrix remodeling | MMP2 | 1,28 ± 0,09 | 1,50 ± 0,06 | 0,97 ± 0,05 | 1,82 ± 0,16 |
|  | MMP3 | 4,34 ± 0,31 | 5,57 ± 0,24 | 3,46 ± 0,18 | 16,01 ± 1,43 |
|  | TIMP1 | 0,90 ± 0,06 | 0,84 ± 0,04 | 0,86 ± 0,04 | 2,07 ± 0,18 |
|  | TIMP2 | 1,05 ± 0,07 | 0,93 ± 0,04 | 0,82 ± 0,04 | 2,23 ± 0,20 |

FIG. 26D

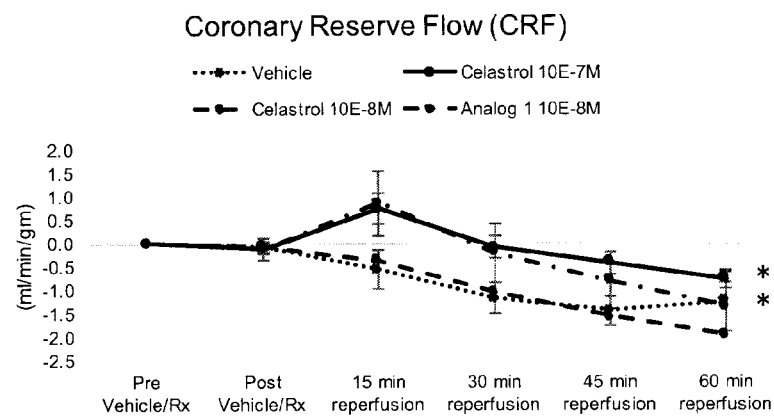
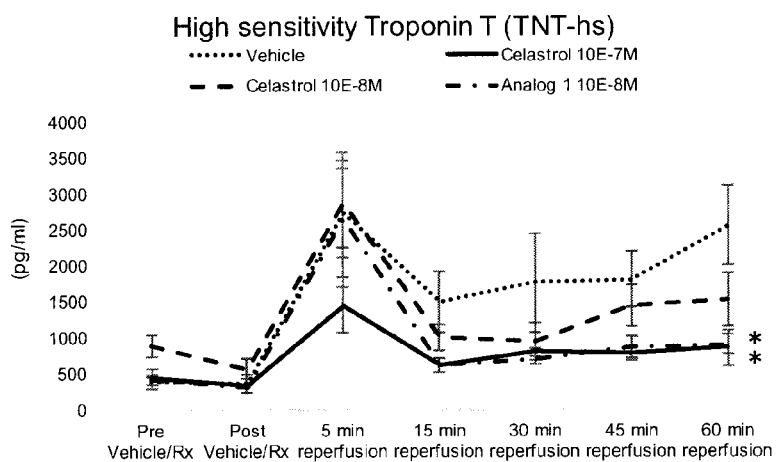
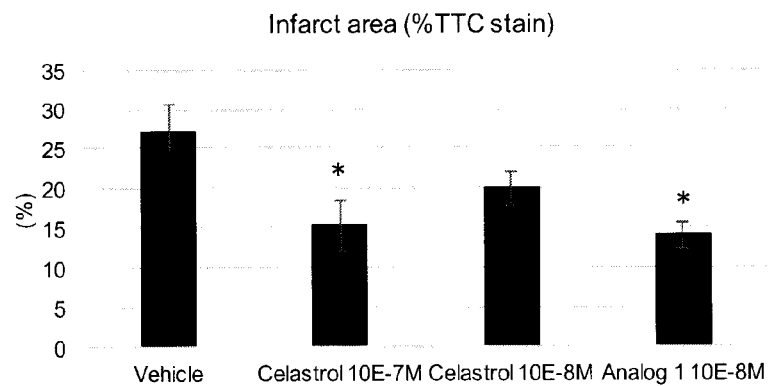
FIG. 33

| Compound | Potency HSR EC50 (uM) | Efficacy HSR max fold induction (%) | Efficacy HSR induction at 1uM dose (fold) | HSR Rank | Potency AR EC50 (uM) | Efficacy AR max fold induction (%) | Efficacy AR induction at 1uM dose (fold) | AR Rank | HSR + AR Rank |
|---|---|---|---|---|---|---|---|---|---|
| Celastrol (1c) | 2,1 | 100 | 36 | | 1,6 | 100 | 3,1 | | |
| Celastrol (2) | 1,7 | 118 | 76 | | 1,1 | 84 | 5,1 | | |
| Celastrol (3) | 1,7 | 110 | 47 | | 1,3 | 103 | 4,2 | | |
| Celastrol AVG | 1,8 | 110 | 53 | 3 | 1,3 | 96 | 4,1 | 3 | 2 |
| Analog 1 | 2,5 | 288 | 98 | 4 | 1,8 | 86 | 4,4 | 4 | 3 |
| Analog 3 | 1,7 | 192 | 64 | 2 | 0,9 | 64 | 4,0 | 1 | 1 |
| Analog 4 | 5,8 | 15 | 3 | 5 | 5,0 | 52 | 1,7 | 5 | 4 |
| Analog 2 | | | 1 | 1 | | | 0,9 | | |
| CDDO analog | 1,1 | 105 | 93 | | 1,4 | 119 | 6,8 | 2 | 1 |

*Rank: (1/Potency) \*ln(AVG Efficacy))*
N=2-3; inductions at 1uM dose
N=1; EC50 and max fold induction

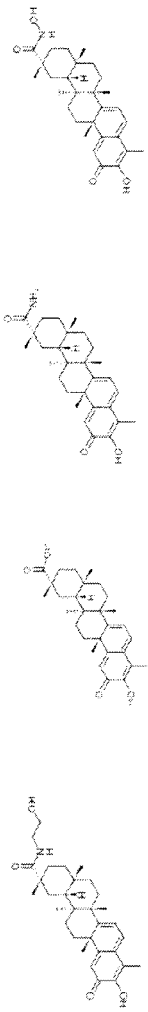

Analog 3    Celastrol    Analog 1    Analog 4

FIG. 35

REAGENTS, COMPOSITIONS AND METHODS FOR IMPROVING VIABILITY AND FUNCTION OF CELLS, TISSUES AND ORGANS

CROSS REFERENCE TO RELATED APPLICATIONS

This application claims the benefit of U.S. provisional Ser. No. 62/350,258 filed on Jun. 15, 2016, the entire content of which is incorporated herein by reference.

TECHNICAL FIELD

The present invention provides reagents, compositions and methods for modulating the state of a cell, a cell preparation, a tissue, a graft or an organ in vitro, ex vivo or in vivo. The present Invention also relates to reagents, compositions and methods for improving the viability and/or function of cells or for the in vitro, ex vivo or in vivo protection of cells, tissues, grafts or organs from various damages. The reagents and composition may comprise an HSP90 co-factor inhibitor such as Celastrol or a Celastrol analog either alone or In combination with an adjunct agent (e.g., NRF-2 activator, antioxidant, etc.).

The present invention particularly relates to treatment or prevention of ischemic injury and related stressors (hypoxia, oxidative stress, Inflammation, shock etc.). The present Invention also particularly relates to cell- and tissue-based therapies (e.g., regenerative medicine, grafts, transplantation, etc).

BACKGROUND ART

Despite numerous technical advances in cardiology during the past decades, ischemic heart disease remains a major cause of morbidity and mortality worldwide. Following myocardial infarction (MI), reperfusion of the ischemic heart Induces additional stress due to a massive increase in free radical production, inflammatory cell infiltration and changes in local pH. Final infarct size can be significantly reduced if cardioprotective measures are set in place. Cardiac pre- and post-conditioning have been studied including mechanical techniques (repetitive short cycles of ischemia/reperfusion (I/R) by coronary clamping), but the simplest and more clinically transferable technique would be pharmacological conditioning. In this setting, cardioprotection would involve a reduction on I/R-induced cell death, with Inhibition of mitochondrial permeability transition pore (mPTP) opening, and lowering of oxidative stress, leading to a reduced infarct area and preservation of ventricular function.

The Applicants Investigated the effect of Celastrol (a plant triterpene) on hypoxic cultures of H9c2 rat cardiomyoblasts and in a rat model of Mi. and treatment efficacy was assessed by echocardiography and histological analysis. The Applicant discovered that in H9c2 cells, Celastrol triggered reactive oxygen species (ROS) formation within minutes, induced nuclear translocation of the transcription factor heat shock factor 1 (HSF1) resulting in a heat shock response (HSR) leading to increased expression of heat shock proteins (HSPs) including HSP70 as well as HSP32 (haeme oxygenase-1, HO-1). Celastrol Improved H9c2 survival under hypoxic stress, and functional analysis revealed HSF1 and HO-1 as key effectors induced by Celastrol promoting cellular and tissue protection. In the rat ischaemic myocardium, daily Celastrol treatment improved cardiac function and reduced adverse left ventricular remodelling at day 14. Celastrol triggered expression of cardioprotective HO-1 and inhibited fibrosis and infarct size. In the peri-infarct area, Celastrol reduced myofibroblast and macrophage infiltration, while attenuating up-regulation of TGF-β and collagen.

The Applicants were the first to report that Celastrol treatment promoted cardiomyocyte survival, reduction of injury and adverse remodelling with preservation of cardiac function and concluded that Celastrol may represent a novel potent pharmacological cardioprotective agent mimicking ischaemic conditioning that could have a valuable impact in the treatment of myocardial infarction (S. Der Sarkissian et al., British J. Pharmacol., 2014, 171:5265-5279).

The Applicant also investigated the effect of Celastrol on the in vitro and ex vivo protection of stem cells to repopulate the injured myocardium. Indeed, stem cell transplantation has been proposed as a novel treatment approach for tissue engineering and regenerative medicine for various disease states. Stem cell-based therapy has been explored in pre-clinical animal models of ischemic disorders or diseases, and has been used in early clinical trials for ischemic disorders such as stroke, MI and peripheral arterial disease (PAD).

Inflammation ensues very rapidly post-MI and is prompted by the detection of high levels of ROS and necrotic cellular debris by resident cells and circulating leukocytes. These cells hone to the injured tissue and further release ROS, proteolytic enzymes, pro-inflammatory and cytotoxic diffusible factors and participate in phagocytosis of necrotic cells and disruption of extracellular matrix (ECM) components. While important for clearing the tissue of compromised cells and debris, Inflammation that becomes excessive or chronic results in infarct expansion, adverse remodeling and poor patient outcomes[1,2,3,4].

Since myocardium generally has only very limited regenerative capability, the space vacated by the death of cardiomyocytes is replaced by a fibrotic scar which adversely impacts cardiac function. Therefore, research into the promotion of myocardial regeneration using cell-based therapeutic strategies, such as stem cell transplantation are of high interest. So far, most of the positive effects of stem cells appear to result from paracrine actions on existing tissues rather than differentiation, incorporation or cellular fusion of the stem cells within the site of the lesion. Paracrine signaling of engrafted cells may act by reducing apoptosis, Inflammation, and fibrosis, and stimulate angiogenesis and other repair processes to occur.[1,2]

Stem cell therapy has the potential to improve healing of ischemic heart, repopulate injured myocardium, and restore cardiac function. It offers a therapeutic solution beyond the limits of conventional treatments, with the prospect of delivering a cure. The tremendous hope and potential of stem cell therapy are well understood, with feasibility and safety having been demonstrated in animal models and clinical trials such as IMPACT-CABG and COMPARE-AMI for autologous CD133+ stem cell transplant for heart failure treatment.[5,6] Yet, recent trials involving cell therapy for cardiovascular diseases have yielded mixed results with inconsistent data re-igniting interest in the unresolved questions regarding the mechanisms responsible for the therapeutic efficacy of stem cells. Indeed, the biggest impediment lessening clinical effectiveness of cell therapy is the poor viability and retention of transplanted cells, particularly in ischemic tissue. Regardless of the cell type, less than 1% of transplanted cells survive in the ischemic myocardium days after transplantation.[7,8]

The Applicant discovered that Celastrol rapidly and strongly activates endogenous cytoprotective properties and increases stem cell survival to hypoxic and oxidative conditions mimicking the ischemic transplant microenvironment. The Applicant observed a dramatic and rapid activation of the PI3K/Akt and p44/42 MAPK (ERK1/2) pathways with upregulation of effectors and important genes involved in cellular protection and survival: Hif1a, HO-1 (HSP32), HSP27, HSP70 and VEGF, as well as increase in Hsf1 translocation from the cytoplasm to the nucleus. The Applicant concluded that pre-conditioning of stem cells with Celastrol could be a safe and efficient therapy for clinical applications such as ischemic cardiovascular diseases (Der Sarkissian et al., Pre-Conditioning of Stem Cells With Celastrol to Enhance their Therapeutic Potential, Circulation 2011; 124:A14198).

Nevertheless, there remain an important need for potent compounds, compositions and methods for Improving the survival and function of cells in an in vitro, ex vivo or in vivo setting by administering said compounds or compositions at the ischemic site or via pre-conditioned cells.

The present description refers to a number of documents, the content of which is herein Incorporated by reference in their entirety.

SUMMARY OF THE INVENTION

The present invention provides in a first aspect thereof, a composition or pharmaceutical composition which may comprise one or more compounds that activate the heat shock response and antioxidant response, one or more compounds that activate Heat shock protein 90 (HSP90) inhibition and Kelch-like ECH-associated protein 1 (KEAP-1) Inhibition, one or more compounds that activate the heat shock factor protein 1 (HSF1) pathway and the Nuclear factor (erythroid-derived 2)-like 2 (NRF2) pathway, one or more compounds that activate Heat shock proteins (HSP) and antioxidants effectors.

The present invention provides in a more particular aspect, a composition or pharmaceutical composition which may comprise one or more compounds selected from a group consisting of natural triterpenes, synthetic triterpene analogs and/or an adjunct agent.

Compounds that may be used to carry the present invention, may include for example, Celastrol, a Celastrol analog, a compound of the withanolide family or an analog thereof, a compound of the limonoid family (e.g., Gedunin) or an analog thereof, a Bardoxolone/CDDO compound or an analog thereof (e.g., CDDO-methyl), a curcuminoid (e.g., Curcumin) or an analog thereof, Carnosol or an analog thereof, tert-Butylhydroquinone (tBHQ) or an analog thereof, Bis(2-hydroxybenzylidene)acetone (2HBA) or an analog thereof, acetylenic tricyclic bis(cyanoenone) (TBE-31) or an analog thereof, epigallocatechin gallate (EGCG) or an analog thereof, gambogic acid or an analog thereof, Novoblocin or an analog thereof, Lonidamine or an analog thereof, Andrographolide or an analog thereof, Edaravone or an analog thereof, Ascorbic acid or an analog thereof, or any combination thereof.

More particularly, the present invention may be carried out by using one or more compound of Formula I

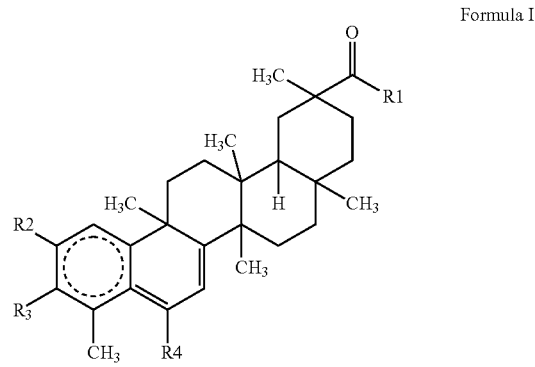

Formula I wherein R1 may be selected, for example, from the group consisting of —H, —F, —Cl, —Br, —I, —CN, -aryl, alkyl, imidazole, —ORa, —NRbRc, —(CH$_2$)$_n$OH, and —(CH$_2$)$_n$NH$_2$;

wherein Ra may be selected from the group consisting of H, a substituted or unsubstituted straight alkyl group of 1 to 6 carbon atoms, a substituted or unsubstituted branched alkyl group of 3 to 6 carbon atoms and a protecting group;

wherein Rb and Rc may independently be selected from the group consisting of —H, —OH, —OCH$_3$ a substituted (e.g. —CH$_2$CH$_2$OH, etc.) or unsubstituted straight alkyl group of 1 to 6 carbon atoms, a substituted or unsubstituted branched alkyl group of 3 to 6 carbon atoms and a protecting group;

wherein n may be 0, 1, 2, 3 or 4;

wherein R2 and R3 may independently be selected from the group consisting of —H, —ORd, =O, —C(=O)OH, —C(=O)ORx, and —C(=O)Rx;

wherein Rd may be H or a lower alkyl group of 1 to 3 carbon atoms;

wherein Rx may be H or a lower alkyl group of 1 to 3 carbon atoms;

wherein R4 may be selected from the group consisting of —H, —OH and a lower alkyl group of 1 to 3 carbon atoms.

In accordance with the present invention, the compound may Include, for example, compounds of Formula Ia, a pharmaceutically acceptable salt, a stereoisomer, a tautomer or a pro-drug thereof,

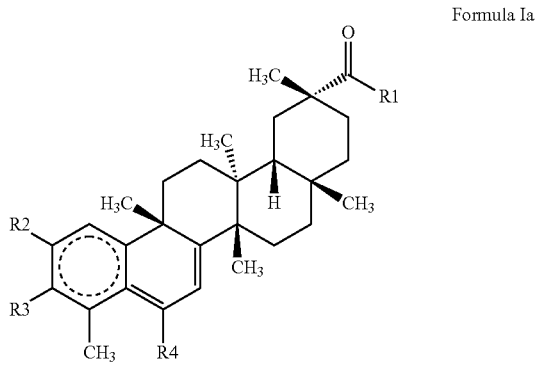

Formula Ia wherein R1 may be selected, for example, from the group consisting of —H, —F, —Cl, —Br, —I, —CN, -aryl, alkyl, imidazole, —ORa, —NRbRc, —(CH$_2$)$_n$OH, and —(CH$_2$)$_n$NH$_2$;

wherein Ra may be selected from the group consisting of H, a substituted or unsubstituted straight alkyl group of 1 to 6 carbon atoms, a substituted or unsubstituted branched alkyl group of 3 to 6 carbon atoms and a protecting group;

wherein Rb and Rc may Independently be selected from the group consisting of —H, —OH, —OCH$_3$ a substituted or unsubstituted straight alkyl group of 1 to 6 carbon atoms, a substituted or unsubstituted branched alkyl group of 3 to 6 carbon atoms and a protecting group;

wherein n may be 0, 1, 2, 3 or 4;

wherein R2 and R3 may independently be selected from the group consisting of —H, —ORd, =O, —C(=O) OH, —C(=O)ORx, and —C(=O)Rx;

wherein Rd may be H or a lower alkyl group of 1 to 3 carbon atoms;

wherein Rx may be H or a lower alkyl group of 1 to 3 carbon atoms:

wherein R4 may be selected from the group consisting of —H, —OH and a lower alkyl group of 1 to 3 carbon atoms.

In accordance with the present invention, compounds of Formula I or Ia encompass those in which R1 may more particularly be selected from the group consisting —ORa and —NRbRc; Ra may selected from the group consisting of H, a substituted or unsubstituted straight alkyl group of 1 to 6 carbon atoms, a substituted or unsubstituted branched alkyl group of 3 to 6 carbon atoms and a protecting group; Rb and Rc may independently be selected from the group consisting of —H, —OH, —OCH$_3$ a substituted or unsubstituted straight alkyl group of 1 to 6 carbon atoms, a substituted or unsubstituted branched alkyl group of 3 to 6 carbon atoms and a protecting group; R2 and R3 may independently be selected from the group consisting of —H, —ORd, and =O, Rd may be H or a lower alkyl group of 1 to 3 carbon atoms; and/or R4 may be —H, or CH$_3$.

Further in accordance with the present invention, compounds of Formula I or Ia encompass those in which R1 may more particularly be selected from the group consisting —ORa and —NRbRc; Ra may be selected from the group consisting of H and a lower alkyl group of 1 to 3 carbon atoms; Rb and Rc may independently be selected from the group consisting of —H, —OH, and —CH$_2$CH$_2$OH; R2 and R3 may independently be selected from the group consisting of —H, —OH, —OCH$_3$ and =O; and/or R4 may be —H, or CH$_3$.

Yet further in accordance with the present invention, compounds of Formula I or Ia encompass those in which R1 may more particularly be selected from the group consisting —ORa and —NRbRc; Ra may be selected from the group consisting of H and —CH$_3$; Rb and Rc may independently be selected from the group consisting of —H, —OH, and —CH$_2$CH$_2$OH; R2 and R3 may independently be selected from the group consisting of —OH, and =O; and/or R4 may be —H.

Exemplary embodiments of the compounds encompassed in the present invention include those of Formula I or Ia where R1 is NRbRc.

Exemplary embodiments of the compounds are provided in FIG. 23 and may include for example, Celastrol analogs Identified as Analog 1, Analog 2, Analog 3, Analog 4, Analog 5, Analog 6 or dihydrocelastrol.

Celastrol analogs that are particularly contemplated by the present invention Includes Analog 1, Analog 2, Analog 3, Analog 4 and dihydrocelastrol. Analog 1 is more particularly contemplated.

In some instances, Celastrol may particularly be excluded from some aspects of the invention. For example, compositions of Celastrol alone or its uses as a sole compound in methods of treating cardiac ischemia or stem cells protection have been disclosed in the literature (Der Sarkissian et al., Pre-Conditioning of Stem Cells With Celastrol to Enhance their Therapeutic Potential, Circulation 2011; 124:A14198; S. Der Sarkissian et al., British J. Pharmacol., 2014, 171: 5265-5279).

Accordingly, when the compositions, methods and uses comprise Celastrol, it may preferably be a compound of Formula I or Formula Ia other than Celastrol or used in combination with another compound, i.e., a compound of Formula I or Formula Ia and/or an adjunct agent.

Alternatively, the present invention may be carried out using a compound of Formula I, Formula Ia, a pharmaceutically acceptable salt, a stereoisomer, a tautomer or a pro-drug thereof having a R1, R2, R3 or R4 group defined herein that is different from that of the corresponding R1, R2, R3 or R4 group of Celastrol.

In accordance with an embodiment of the invention, the adjunct agent may be for example, 2HBA, andrographolide, ascorbic acid, cafestol, camosolbardoxolone-imidazole (CDDO-im), chalcone, N6-[2-[[4-(2,4-dichlorophenyl)-5-(1H-imidazol-2-yl)-2-pyrimidinyl]amino]ethyl]-3-nitro-2, 6-pyridinediamine (CHIR98014), conglobatin, curcumin, cycloastragenol, 1,2-dithiole-3-thione (D3T), doramapimod, edaravone. EGCG, gambogic acid, ganetespib, gedunin, IQ-1, limonin, lonidamines, melatonin, benzamide tetrahydroindolones, N886, alkylamino biphenylamides, novobiocin, pyridoxal 5'-phosphate (P5'-P), pyrithione, quercetin, radicicol, resveratrol, N-(2-cyano-3,12-dioxo-28-noroleana-1,9(11)-dien-17-yl)-2,2-difluoro-propanamide or omaveloxolone (RTA-408), 4-(4-Fluorophenyl)-2-(4-hydroxyphenyl)-5-(4-pyridyl)-1H-imidazole (SB202190), 3-(2,4-Dichlorophenyl)-4-(1-methyl-1H-indol-3-yl)-1H-pyrrole-2, 5-doone (SB216763), SNX-5422 (PF-04929113), sodium Butyrate, sulforane, tetrabromobenzotriazole (TBB), tert-butythydroquinone (tBHQ), valporic acid, withafein A, withanolide, ergosterols, lupenones and analogs of any such adjunct agents.

More specifically, the adjunct agent may Include for example, tBHQ, camosol, curcumin, 2HBA, or EGCG or analogs thereof.

The present invention provides in an additional aspect thereof, a composition or pharmaceutical composition which may comprise, for example, a) one or more compound of Formula I, Formula Ia, a pharmaceutically acceptable salt, a stereoisomer, a tautomer or a pro-drug thereof either alone or in combination with one or more adjunct agent and b) a carrier or pharmaceutically acceptable carrier or excipient.

The present invention provides a method of modulating the state of a cell (an isolated cell), a cell preparation, a tissue (an isolated tissue), a graft (an isolated graft) or an organ (an isolated organ). Such modulation may be done so as to increase or preserve viability or resistance to death, damages and/or stress, as well as the functionality. Such modulation may be done in a manner that Increase resilience profile to cell death, more resistance to oxidative and/or hypoxic stressors, and/or enhanced profile for protein expression that may comprise of enhanced secretion of various proteins Including but not limited to heat shock proteins, antioxidant proteins, growth factors, and/or reducing deleterious expressions such peptide mediators associated with cell senescence.

The method may comprise contacting the cell, cell preparation, tissue, graft or organ with a) a composition that may comprise one or more compound of Formula I, Formula Ia, a pharmaceutically acceptable salt, a stereoisomer, a tautomer or a pro-drug thereof, b) a combination that may comprise one or more compound of Formula I, Formula Ia, a pharmaceutically acceptable salt, a stereoisomer, a tautomer or a pro-drug thereof and an adjunct agent, c) a distinct cell preparation that is contacted or has been contacted with one or more compound of Formula I, Formula Ia, a pharmaceutically acceptable salt, a stereoisomer, a tautomer or a pro-drug thereof or with the combination thereof, or d) a secretome or cell media of a distinct cell preparation that has been contacted with the one or more compound of Formula I, Formula Ia, a pharmaceutically acceptable salt, a stereoisomer, a tautomer or a pro-drug thereof or with the combination thereof.

The present Invention provides in an additional aspect, a method of protecting cells, tissues, grafts or organs from damages or stressors (e.g., oxidative, hypoxic, inflammatory, thermal, osmotic, mechanical) that can be incurred in various pathological conditions (e.g. ischemia, ischemia/reperfusion, shock, sepsis) or manipulation procedures (e.g. freeze/thaw cycles, cell encapsulation, expansion, enrichment and purification steps, graft preparation/manufacturing etc.).

The method may comprise contacting the cells, tissues, grafts or organs with a composition comprising one or more compounds that activate the heat shock response and antioxidant response, one or more compounds that activate the HSP90 inhibition and the KEAP-1 inhibition pathway, one or more compounds that activate the HSF1 pathway and NRF2 pathway, one or more compounds that activate HSPs and antioxidants.

The method may also comprise contacting the cells, tissues, grafts or organs with a composition comprising one or more compounds selected from the group consisting of natural triterpenes, synthetic triterpene analogs and/or an adjunct agent.

The method may more specifically comprise contacting the cells, tissues, grafts or organs with a composition comprising one or more compound of Formula I, Formula Ia, a pharmaceutically acceptable salt, a stereoisomer, a tautomer or a pro-drug thereof. In accordance with the present invention, the method may be performed in vitro, ex vivo, in vivo.

Therefore, in accordance with the present invention, the method may be an ex vivo method performed on a cell preparation, tissue or organ. The cell preparation, tissue or organ thus conditioned may subsequently be administered/transplanted into a mammal in need (e.g., a human mammal). The method may also be an in vivo method performed by administration of the composition, combination, distinct cell preparation or secretome to a mammal in need (e.g., a mammal suffering from or susceptible of suffering from an ischemic disease, undergoing surgery or medical intervention, or having a degenerative disease with cell and tissue loss).

The degenerative disease may comprise cardiomyopathy, hepatic disease such as non-alcoholic fatty liver disease, non-alcoholic steatohepatitis (NAFLD/NASH), cirrhosis, pulmonary disease such as chronic obstructive pulmonary disease (COPD), osteoarthritis, pancreatic disorder such as diabetes, neurodegeneration such as Alzheimers, Parkinsons, dementia, amyotropic lateral sclerosis (ALS) disease, etc.

The composition, combination, distinct cell preparation or secretome may be administered immediately prior to, during or immediately after the surgery or medical intervention and may be administered for example, systemically or locally.

The method may also be an in vitro method performed on cells in culture or prior to freezing.

The cell, cell preparation, tissue, graft or organ may be contacted with the compound, combination, distinct cell preparation or secretome for a duration, for example, of at least between 5 to 180 minutes prior to their use.

In accordance with an embodiment of the present invention, the compound of Formula I or Formula Ia may be used at a concentration of between $10^{-6}$ M to $10^{-10}$ M.

The method may comprise administering the compound, combination, cell preparation or secretome locally or systemically. For example, when a compound, combination or secretome is administered it may administered systemically (e.g., Intravenously) or locally (e.g., topically, at a damaged site). When a cell preparation is administered, it may preferentially be administered locally (e.g., at a site where ischemia is suspected, at a site in need of cytoprotection, etc.).

The cells may be Immortalized or primary cells. The cells may be for example, stem cells, cardiomyocytes, cardiomyoblasts, muscle cells, kidney cells, pancreatic cells, hepatic cells, neurons, endothelial cells, epithelial cells.

The stem cells may be embryonic, multipotent or pluripotent stem cells. Exemplary embodiments of stem cells may include mesenchymal stem cells, hematopoietic stem cells, induced pluripotent stem cells. In accordance with the present invention, the cells are non-cancerous cells.

The cells are preferably from a mammal, such as for example a human. The cells may be suitable for allogenic stem cell transplantation or for autologous stem cell transplantation. The cells may originate from a commercial source or may be isolated from a donor or host. The cells may be selected on the basis of specific and desirable markers.

In accordance with the present invention, the method may comprise additionally contacting the cells, tissues, grafts or organs with one or more adjunct agent. The cells, tissues, grafts or organs may thus be contacted with a composition comprising both a) the compound of Formula I or Formula Ia (or a pharmaceutically acceptable salt, a stereoisomer, a tautomer or a pro-drug thereof) and b) the adjunct agent mixed together or the compound and adjunct agent may be added one after the other.

The cells, tissues, grafts or organ may also be contacted sequentially with the compound of Formula I, Formula Ia (or a pharmaceutically acceptable salt, a stereoisomer, a tautomer or a pro-drug thereof) and the adjunct agent.

The present invention further provides in an aspect thereof a method of preventing or treating ischemic diseases including for example, ischemic cardiovascular diseases, stroke, myocardial infarction (MI), peripheral arterial disease (PAD), or diseases where cell and tissue loss or degeneration occurs for example diabetes, hepatic disease, pulmonary disease, etc.

The method may comprise administering to a mammal in need thereof a composition comprising one or more compounds that activate the heat shock response activation and antioxidant response activation, one or more compounds that activate the HSP90 inhibition and the KEAP-1 inhibition pathway, one or more compounds that activate the HSF1 activation and the NRF2 pathway, one or more compounds that activate HSPs and antioxidants or a secretome of a cell preparation conditioned with such composition.

The method may also comprise administering to a mammal in need thereof a stem cell preparation pre-conditioned with a composition comprising one or more compounds that activate the heat shock response activation and antioxidant response activation, one or more compounds that activate the HSP90 inhibition and the KEAP-1 inhibition pathway, one or more compounds that activate HSF1 and NRF2 pathway, one or more compounds that activate HSPs and antioxidants.

In addition, the method may comprise administering to the mammal in need, a composition comprising one or more compounds selected from the group consisting of natural triterpenes, synthetic triterpene analogs and/or an adjunct agent.

The method may also comprise administering to the mammal in need, a stem cell preparation pre-conditioned with a composition comprising one or more compounds selected from the group consisting of natural triterpenes, synthetic triterpene analogs and/or an adjunct agent.

The method may also comprise administering to the mammal in need, a secretome or culture media of stem cell preparation treated with a composition comprising one or more compounds described herein and/or an adjunct agent.

The method may more specifically comprise administering to a mammal in need thereof a) a composition comprising one or more compound of Formula I, Formula Ia, a pharmaceutically acceptable salt, a stereoisomer, a tautomer or a pro-drug thereof, b) a stem cell preparation pre-conditioned with one or more compound of Formula I, Formula Ia, a pharmaceutically acceptable salt, a stereoisomer, a tautomer or a pro-drug thereof or c) a secretome of a cell preparation conditioned with such composition.

In accordance with the present invention, the method encompasses administration of a composition comprising a combination of a) compound of Formula I, Formula Ia, a pharmaceutically acceptable salt, a stereoisomer, a tautomer or a pro-drug thereof and b) an adjunct agent, administration of stem cells pre-conditioned with a composition comprising such combination or administration of a secretome of a cell preparation conditioned with such combination.

In accordance with an embodiment of the invention, the stem cell preparation may be an autologous stem cell preparation isolated from the mammal in need. In accordance with a further embodiment of the invention, the stem cell preparation may be an allogenic stem cell preparation isolated from a mammal donor. In order to be suitable for administration to a mammal, the allogenic stem cell preparation is preferably HLA-typed matched. The stem cell preparation may also be immune-privileged, hypoimmunogenic or immune-evasive.

The present invention also provides in an additional aspect thereof, a cell preparation, or an isolated cell, tissue, graft or organ preparation pre-conditioned with a composition comprising one or more compounds that activate the heat shock response activation and antioxidant response activation, one or more compounds that activate the HSP90 inhibition and the KEAP-1 inhibition pathway, one or more compounds that activate the HSF1 activation and the NRF2 pathway, one or more compounds that activate the HSP activation and antioxidant response activation or with a secretome of a distinct cell preparation conditioned with such composition.

The present invention provides in a further aspect thereof, an Isolated cell, tissue, graft or organ preparation pre-conditioned with a composition comprising one or more compounds selected from the group consisting of natural triterpenes, synthetic triterpene analogs and/or an adjunct agent.

More specifically, the present Invention provides in yet an additional aspect thereof, a cell preparation or an isolated cell, tissue, graft or organ preparation pre-conditioned with a composition comprising one or more compound of Formula I, Formula Ia, a pharmaceutically acceptable salt, a stereoisomer, a tautomer or a pro-drug thereof or with a secretome of distinct cell preparation conditioned with such composition.

In accordance with the present invention, the isolated cell, tissue, graft or organ preparation may be pre-conditioned with a composition comprising a combination of a) compound of Formula I, Formula Ia, a pharmaceutically acceptable salt, a stereoisomer, a tautomer or a pro-drug thereof and b) an adjunct agent.

In accordance with the present invention, the isolated cell, tissue, graft or organ preparation may be conditioned with a secretome of cells pre-conditioned with a composition comprising a combination of a) compound of Formula I, Formula Ia, a pharmaceutically acceptable salt, a stereoisomer, a tautomer or a pro-drug thereof and b) an adjunct agent.

In accordance with an embodiment of the invention, the composition may be washed from the preparation prior to use or may remain as part of the preparation.

In accordance with an exemplary embodiment, the cell preparation may be a stem cell preparation, for example, stem cells treated in vitro or stem cells harvested from a donor having previously received systemically the treatment.

In accordance with another embodiment of the invention, the cellular preparation may be a cell suspension. In accordance with a further embodiment of the invention, the cellular preparation may in the form of a three-dimensional scaffold. In order to obtain a three-dimensional scaffold, cells may be cultured as cell aggregates, in the presence of microcarriers, on alginate microencapsulates, in hydrogels (e.g., thermoreversible hydrogels, chitosane based hydrogels etc.), in nanostructure scaffolds composed of self-assembling peptides (Meng, X. et al., SpringerPlus, 2014, 3:80).

The present invention further relates to a method of lowering cellular damages in transplantation of stem cells, tissues, grafts or organs, the method may comprise contacting the stem cells, tissues, grafts or organs with a composition comprising one or more compounds that activate the heat shock response activation and antioxidant response activation, one or more compounds that activate the HSP90 inhibition and the KEAP-1 inhibition pathway, one or more compounds that activate the HSF1 activation and the NRF2 pathway, one or more compounds that activate the HSP activation and antioxidant response activation or with a secretome of a cell preparation conditioned with such composition.

The present invention further relates to a method of lowering cellular damages in transplantation of stem cells, tissues, grafts or organs, the method may comprise contacting the stem cells, tissues, grafts or organs with a composition comprising one or more compounds selected from the group consisting of natural triterpenes, synthetic triterpene analogs and/or an adjunct agent.

More particularly, the present invention further provides a method of lowering cellular damages in transplantation of stem cells, tissues, grafts or organs, the method comprising contacting the stem cells, tissues, grafts or organs with a composition comprising at least one compound of Formula I, Formula Ia, a pharmaceutically acceptable salt, a stereoisomer, a tautomer or a pro-drug thereof or with a secretome of a cell preparation conditioned with such composition prior to and/or during and/or subsequent to transplantation.

In accordance with an embodiment of the invention, the method may comprise administering a combination of a)

compound of Formula I, Formula Ia, a pharmaceutically acceptable salt, a stereoisomer, a tautomer or a pro-drug thereof and b) an adjunct agent.

In a further aspect, the present invention relates to the use of one or more compounds that activate the heat shock response activation and antioxidant response activation, one or more compounds that activate the HSP90 inhibition and the KEAP-1 inhibition pathway, one or more compounds that activate the HSF1 activation and the NRF2 pathway, one or more compounds that activate the HSP activation and antioxidant response activation for protecting cells, tissue, graft or organs from stress or damages.

In yet a further aspect, the present invention relates to the use of one or more compounds selected from the group consisting of natural triterpenes, synthetic triterpene analogs and/or an adjunct agent for protecting cells, tissue, graft or organs from stress or damages.

In a more particular aspect, the invention relates to the use of one or more compound of Formula I, Formula Ia, a pharmaceutically acceptable salt, a stereoisomer, a tautomer or a pro-drug thereof for protecting cells, tissue, graft or organs from stress or damages.

In accordance with an additional aspect of the invention the Invention relates to the use of a combination of a) compound of Formula I, Formula Ia, a pharmaceutically acceptable salt, a stereoisomer, a tautomer or a pro-drug thereof and b) an adjunct agent.

In yet an additional aspect the present invention provides a method of treating a patient in need of a surgery or medical Intervention or susceptible of suffering from cellular stress or damages.

In accordance with an embodiment of the invention, the method may comprise administering a composition comprising one or more compounds as defined herein.

In accordance with a more specific embodiment of the invention, the method may comprise administering a composition comprising a compound of Formula I, Formula Ia, a pharmaceutically acceptable salt, a stereoisomer, a tautomer or a pro-drug thereof prior to and/or during the surgery or medical Intervention.

In a further embodiment of the invention thereof, the method may comprise administering a combination of a) compound of Formula I, Formula Ia, a pharmaceutically acceptable salt, a stereoisomer, a tautomer or a pro-drug thereof and b) an adjunct agent.

In accordance with the present Invention, the composition may be administered locally, for example, at a site of surgery or medical intervention. In accordance with another embodiment of the invention, the composition may be administered systemically.

In accordance with the invention, the compounds or compositions may be administered to a mammal in need directly at a site susceptible to cellular damages. The compounds or composition may thus be administered for preventing or treating cellular damages.

The present invention also relates to a kit which may include a first vial comprising a compound of Formula I, Formula Ia, a pharmaceutically acceptable salt, a stereoisomer, a tautomer or a pro-drug thereof and a second vial comprising cells.

In accordance with a further embodiment of the Invention, the kit may comprise a third vial containing an adjunct agent. In accordance with an embodiment of the invention, the cells may be stem cells.

The present invention also relates to a kit where the different components are pre-mixed.

The invention also provides a device suitable for in vivo administration of the composition, combination, distinct cell preparation or secretome to a mammal in need. The device may be, for example, a pre-filled syringe or syringes having a compartment that may accommodate the composition, combination, distinct cell preparation or secretome.

The invention also provides a device suitable for cell, tissue preparation. The device may be, for example, a cell sorting or cell culture or expansion device such as a bioreactor, that may accommodate the composition, combination, distinct cell preparation or secretome.

Additional aspects of the invention are also provided in the following items 1 to 31:

1. A method of improving the resistance of cells to cell death, said method comprising contacting the cells with an effective amount of one or more compounds that activate the HSF1 pathway and the NRF2 pathway.
2. A method of producing a conditioned population of cells with increased resilience profile to cell death, more resistance to oxidative and/or hypoxic stressors, and/or enhanced profile for protein expression that comprises enhanced secretion of at least one of heat shock proteins, antioxidant proteins, and/or growth factors, anti-inflammatory cytokines, chemokines, and/or reduced expressions of deleterious peptide mediators such as senescence associated proteins, said method comprising contacting the cells with an effective amount of one or more compounds that activate the HSF1 pathway and the NRF2 pathway.
3. A method of improving the viability and retention of transplanted or transfused cells, said method comprising contacting the cells with an effective amount of one or more compounds that activate the HSF1 pathway and the NRF2 pathway prior to and/or after transplantation or transfusion.
4. The method of the items set forth herein, wherein said method comprises contacting the cells ex vivo or in vitro prior to transplantation or transfusion.

The method of the items set forth herein, wherein said method comprises contacting the cells in vivo.

5. The method of the items set forth herein, wherein said method comprises contacting the cells in vivo before/after transplantation or transfusion.
6. A method of treating a subject in need of cell transplantation or transfusion, said method comprising (a) contacting the cells to be transplanted with an effective amount of one or more compounds that activate the HSF1 pathway and the NRF2 pathway; and (b) transplanting or transfusing the cells of (a) in said subject.
7. The method of the Items set forth herein, further comprising contacting the transplanted or transfused cells with an effective amount of said one or more compounds after transplantation.
8. The method of the Items set forth herein, wherein said subject is afflicted by organ or tissue ischemia or degeneration and/or wherein said organ or tissue ischemia is cardiac ischemia. Degeneration includes loss of pancreatic cells, cardiac cells, muscle cells, neurons, kidney cells, hepatic cells etc.
10. The method of the items set forth herein, wherein said subject is afflicted by myocardial infarct (MI).
11. The method the items set forth herein, wherein at least one of the one or more compounds is an HSP90 inhibitor.

12. The method of the Items set forth herein, wherein the HSP90 inhibitor is an an HSP90 N or C-terminal inhibitor and more particularly an HSP90 co-factor inhibitor.

13. The method of items set forth herein, wherein at least one of the one or more compounds has NRF2 Inducing activity or antioxidant activity.

14. The method of the items set forth herein, wherein said one or more compounds comprises Celastrol or an analog thereof, a compound of the withanolide family or an analog thereof, a compound of the limonoid family (e.g., Gedunin) or an analog thereof, a Bardoxolone/CDDO compound or an analog thereof (e.g., CDDO-methyl), a curcuminoid (e.g., Curcumin) or an analog thereof, Camosol or an analog thereof, tert-Butylhydroquinone (tBHQ) or an analog thereof, Bis (2-hydroxybenzylidene)acetone (2HBA) or an analog thereof, acetylenic tricyclic bis(cyanoenone) (TBE-31) or an analog thereof, epigallocatechin gallate (EGCG) or an analog thereof, gambogic acid or an analog thereof, Novobiocin or an analog thereof, Lonidamine or an analog thereof, Andrographolide or an analog thereof, Edaravone or an analog thereof, Ascorbic acid or an analog thereof, Gamendazole or an analog thereof, Sulforaphane or an analog thereof, sulphoxythiocarbamate alkyne (STCA) or an analog thereof, or any combination thereof.

15. The method the items set forth herein, wherein said one or more compounds comprises (i) (a) Celastrol or an analog thereof; and (b) EGCG or an analog thereof; (ii) (a) Celastrol or an analog thereof; and (b) tBHQ or an analog thereof; (iii) (a) Celastrol or an analog thereof; and (b) 2HBA or an analog thereof (iv) (a) Celastrol or an analog thereof; and (b) Curcumin or an analog thereof (v) (a) Celastrol or an analog thereof; and (b) Camosol or an analog thereof (vi) (a) Gedunin or an analog thereof; and (b) EGCG or an analog thereof; or (vii) (a) Gedunin or an analog thereof; and (b) tBHQ or an analog thereof, (viii) (a) Gedunin or an analog thereof; and (b) 2HBA or an analog thereof, (ix) (a) Gedunin or an analog thereof; and (b) Curcumin or an analog thereof, (x) (a) Gedunin or an analog thereof; and (b) Camosol or an analog thereof.

16. The method of the items set forth herein, wherein the cell is a stem/pluripotent/progenitor cell or differentiated cell.

17. The method of the items set forth herein, wherein the stem/pluripotent/progenitor cell is a mesenchymal stem cell, a $CD34^+$ cell, or a $CD133^+$ cell.

18. The method of the items set forth herein, wherein the cell is a differentiated cell 19. The method of the items set forth herein, wherein the cell is present in a tissue or an organ.

20. The method of the item set forth herein, wherein said contacting comprises the addition of a single dose or multiple doses of the one or more compounds in the culture medium.

21. The method of the items set forth herein, wherein said contacting comprises administering to the subject a single dose or multiple doses of the one or more compounds.

22. A method of identifying one or more compounds that may be useful for improving the resistance of cells to cell death and/or improving the viability and retention of transplanted or transfused cells, said method comprising (i) contacting a cell with said one or more compounds; (ii) determining whether the HSF1 pathway and the NRF2 pathway are activated in said cell, wherein activation of said pathway is Indicative that said one or more compounds may be useful for improving the resistance of cells to cell death and/or improving the viability and retention of contacted cells, and/or that said one or more compounds may be useful for improving the functionality of cells and/or improving the paracrine secretome of contacted cells.

23. The method of the items set forth herein, wherein the cell is a stem/progenitor cell or differentiated cell.

24. The method of the items set forth herein, wherein the stem/progenitor cell is a mesenchymal stem cell, a $CD34^+$ cell, or a $CD133^+$ cell.

25. The method of the items set forth herein, wherein the cell is a differentiated cell.

26. The method of the items set forth herein, wherein the cell is present in a tissue or an organ.

27. The method of the Items set forth herein, wherein the step of determining whether the HSF1 and NRF2 pathways are activated in said cell comprises measuring the expression of one or more genes under the transcriptional control of HSF1 and/or NRF2, wherein an increase in the expression of said one or more genes is Indicative that the HSF1 and/or NRF2 pathways is/are activated.

28. The method of the items set forth herein, wherein said one or more genes expressed following HSF1 or NRF2 activation are heat-shock proteins (HSPs) (e.g., HSP90, HSP70), glutathione S-transferase, NADPH-quinone oxidoreductase 1 (NQO1), growth factors (e.g., VEGF, FGF2, HGF, IGF), haeme oxygenase 1 (HO1), superoxide dismutases 1-3 (SOD1-3), thioredoxin (TRX), catalase (CAT) and/or glutathione peroxidase (GPx).

29. The method of the items set forth herein, wherein the step of determining whether NRF2 pathways are activated in said cell comprises measuring the expression of one or more pro-inflammatory genes, wherein a decrease in the expression of said one or more genes is indicative that the HSF1 and/or NRF2 pathways is/are activated.

30. The method of the items set forth herein, wherein said one or more inflammatory genes are IL-1β and/or TNFα.

31. The method of the items set forth herein, wherein said method comprises measuring the death of said cell under hypoxic and/or oxidative, hypoxia/reoxygenation stress conditions.

In accordance with the present invention, representative embodiments of HSP90 inhibitors may include for example, Celastrol or an analog of Formula I.

In another aspect, the present invention relates to a composition comprising Celastrol or an analog of Formula I in combination with one or more protective compound.

In accordance with the present invention, the one or more protective compound may be an adjunct agent such as a NRF2 activator or an antioxidant and may comprise, for example, Celastrol, 2HBA, andrographolide, ascorbic acid, cafestol, camosolbardoxolone-imidazole (CDDO-im), chalcone, N6-[2-[[4-(2,4-dichlorophenyl)-5-(1H-imidazol-2-yl)-2-pyrimidinyl]amino]ethyl]-3-nitro-2,6-pyridinediamine (CHIR98014), conglobatin, curcumin, cycloastragenol, 1,2-dithiole-3-thione (D3T), doramapimod, edaravone, EGCG, gambogic acid, ganetespib, gedunin, IQ-1, limonin, lonidamines, melatonin benzamide tetrahydroindolones, N886, alkylamino biphenylamides, novobiocin, pyridoxal 5'-phosphate (P5'-P), pyrithione, quercetin, radicicol, resveratrol, N-(2-cyano-3,12-dioxo-28-noroleana- 1,9(11)-dien-17-yl)-2,2-difluoro-propanamide or omaveloxolone (RTA-408), 4-(4-Fluorophenyl)-2-(4-hydroxyphenyl)-5-(4-pyridyl)-1H-imidazole (SB202190), 3-(2,4-Dichlorophenyl)-4-(1-methyl-1H-indol-3-yl)-1H-pyrrole-2,5-dione (SB216763), SNX-5422 (PF-04929113), sodium Butyrate, sulforane, tetrabromobenzotriazole (TBB), tert-butylhydroquinone (tBHQ), valproic acid, withaferin A, withanolide, ergosterols, lupenones and analogs of any such adjunct agents.

In a further aspect, the present invention relates to a cellular preparation containing live cells that may have improved characteristics following contact with the compositions described herein. The improved characteristics may include an Improved function, an increased expression of genes associated with cytoprotection, an increased viability, an increased survival, an increased resistance to cellular damages from stressors (e.g., oxidative, hypoxic, inflammatory, thermal, osmotic, mechanical) that can be Incurred in various pathological conditions (e.g. ischemia, ischemia/reperfusion, septic shock) or manipulation procedures (e.g. freeze/thaw cycles, cell encapsulation, expansion, enrichment and purification steps, graft preparation/manufacturing etc.).

The cellular preparation may comprise stem cells such as those suitable for preventing or repairing damages due to ischemia. The stem cells may be from a commercial source, isolated from the individual in need of treatment (i.e., autologous) or isolated from a compatible donor (i.e., allogeneic).

In accordance with an embodiment of the present Invention, the cellular or tissue preparation may be pre-conditioned with the composition or reagents described herein. In accordance with a further embodiment of the invention, the cellular preparation may comprise media containing the composition or reagents described herein.

Other objects, advantages and features of the present invention will become more apparent upon reading of the following non-restrictive description of specific embodiments thereof, given by way of example only with reference to the accompanying drawings.

BRIEF DESCRIPTION OF DRAWINGS

In the Appended Drawings:

FIGS. 2A and 28 show that Celastrol preconditioning increases in vivo viability/retention of MSCs. MSCs were treated with conditioning compound or vehicle for 60 minutes. Cells were then washed, labeled with fluorescent cell tracker and injected at t=0 In rat left Ischemic hindlimb. Transplanted cells were imaged in vivo until day 9 using Optix®. 3 million MSC injected in left quadriceps at t=0 are tracked until day 9 using Optix in vivo imaging system. (Log scale).

FIG. 22B shows a compilation map of paracrine viability of H9c2 cells (check marks indicate level of activation; x indicate level of inhibitory effect; ≠ indicates lack of effect; empty cells indicate that the experiment was not performed).

FIG. 23 shows Celastrol analogs tested

FIG. 24 shows a list of potential adjunct agents tested.

FIG. 25A is a table representing mRNA expression of selected genes measured by real-time PCR in human mesenchymal stem cells (hMSC) conditioned with Celastrol alone or in combination with selected adjunct agents. Results are expressed as fold change versus Vehicle-treated cells.

FIG. 25B is a table representing mRNA expression of selected genes measured by real-time PCR in human mesenchymal stem cells (hMSC) conditioned with selected Celastrol analogs alone or In combination with selected adjunct agents. Results are expressed as fold change versus Vehicle-treated cells.

FIG. 26A to 26C shows the result of co-treatment of Celastrol or Celastrol analogs and selected adjunct NRF2 activators on the mRNA expression of cytoprotective gene in human mesenchymal stem cells (hMSCs) measured by real-time PCR. Only treatment combinations that are ≥1.5 fold superior for the expression of VEGF, FGF2, HO1, and SDF1 genes compared to Vehicle-treated cells are retained. Results are expressed as fold change versus Vehicle-treated cells. (Arbitrary angiogenic index: (VEGFa+FGF2+SDF1) *2) (A=Additive effect; S=Synergistic effect).

FIG. 26O shows the TaqMan panel (Thermo Fisher) of antioxidant, growth factor and matrix remodeling mRNA gene expressions following treatment of human mesenchymal stem cells (hMSC) for one hour with Celastrol (1 uM) alone or combined with 2HBA (1 uM) followed by 24 hour incubation in either normoxic or hypoxic (<1% $O_2$) and low serum (0.2% FBS) conditions as may be observed in an infarct microenvironment. Results are expressed as fold change versus Vehicle-treated hMSCs.

FIG. 28 is a picture obtained from confocal microscopy (Olympus, FV1000MPE/BK61WF) experiment showing a pig arteriole conditioned overnight in HBSS media without Celastrol (A) or with (B) Celastrol (1 uM). Vessel sections were stained using the LIIVE/DEAD kit. Arrows point to areas of dead cells and degraded endothelium layer in media containing Vehicle, whereas representative vessel image shows maintenance of the endothelial layer viability and Integrity with Celastrol supplemented media.

FIG. 35 is a Table summarizing the effect of Celastrol (Celastrol 1c: purchased from commercial source; Celastrol 2 and 3 used to generate synthetic analogs) and Celastrol analogs on the heat shock response (HSR) and antioxidant response (AR) measured by Luciferase reporter assays. $EC_{50}$, maximum fold induction and response activations at 1 uM fixed doses are reported. Compounds are ranked according to a compilation of efficacy and potency in HSR and AR pathway stimulation.

DISCLOSURE OF INVENTION

Figure 1:
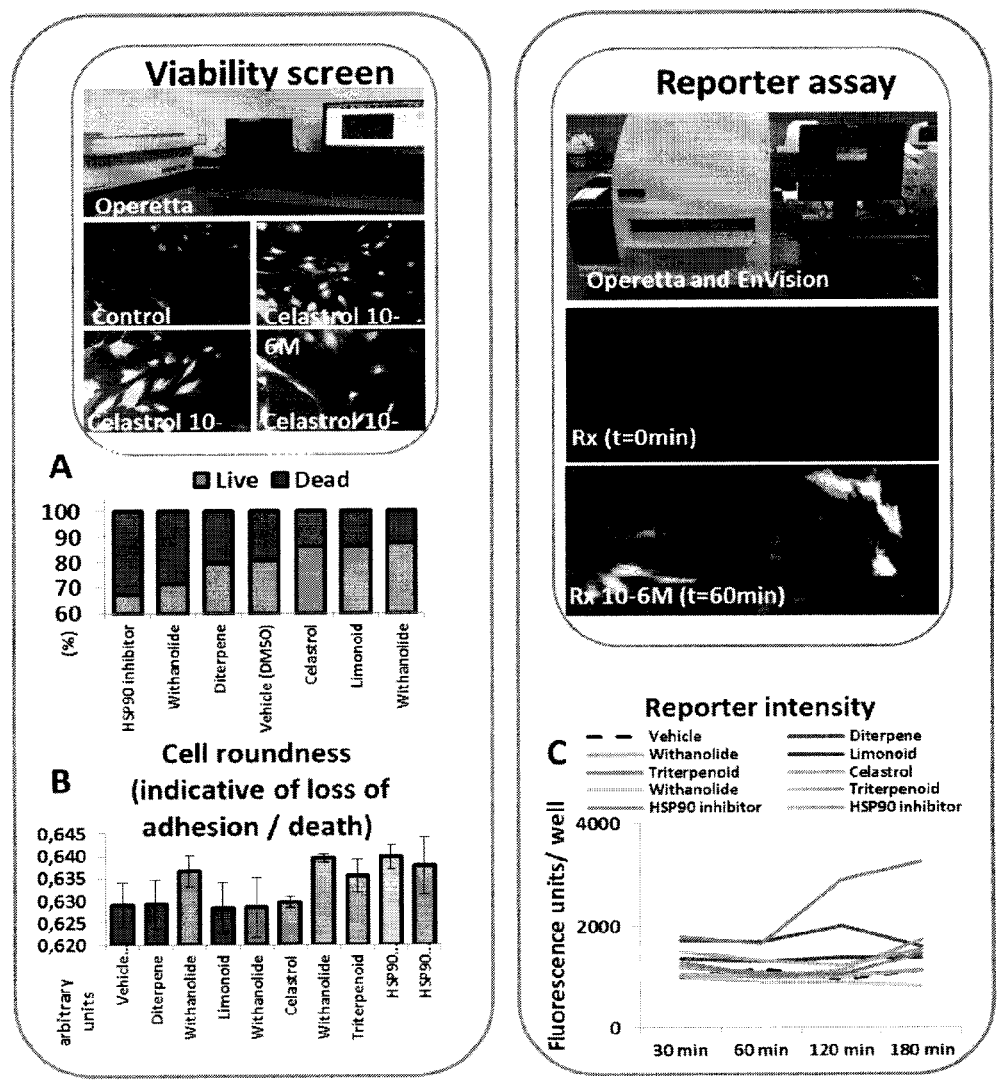
FIG. 1 shows examples of viability (A, B) and reporter based screens (C) of various HSP90 Inhibitors and Celastrol-like compounds. The Perkin Elmer Operetta® High Content Screening System allows detection of various fluorophores and cell morphological changes. The Perkin Elmer Victor Multilabel Counter or EnVision® Multilabel Reader, a Luminometer allows detection of luciferin metabolism. It can also characterize quantitatively the $EC_{50}$ and maximum fold induction using various reporter cell lines.

In the present application, the Applicant showed that Celastrol may be useful to protect cells and tissue from different kinds of damages and may increase the survival of cells that are part of complex tissues, such as grafts and organs. For example, stems cells pre-conditioned with Celastrol alone or in combination with an adjunct agent protect cells from stress and/or damages and stimulate secretion of paracrine mediators and growth factors that enhance the therapeutic profile of cells.

The Applicant also identified Celastol analogues having similar or increased cytoprotective effect and identified several therapeutic combinations having synergistic or additive cytoprotective effects with Celastrol and/or with Celastrol analogues.

Celastrol's mechanisms of Induction of HSR and antioxidant response, leading to upregulation of cytoprotective HPSs is schematized in FIG. 37.

More particularly, Celastrol mechanism of action includes 1) activation of the rapid and transient cellular defense mechanism. More particularly, Celastrol modulates activity of KEAP1, the repressor of the transcription factor Nuclear Factor Erythroid 2-Related Factor 2 (NRF2), thereby allowing translocation of NRF2 to the nucleus and binding to ARE (Antioxidant Response Element) which activates transcription of protective antioxidant mediators and enzymes including HO1 (HSP32).

Celastrol mechanism of action also includes 2) activation of the cellular pathway ensuring extended protection and survival: Celastrol antagonises the essential co-chaperones of HSP90, namely Cdc37, which results in dissociation of the HSF1 from its chaperone repressor HSP90. This leads to HSF1 phosphorylation, trimerization, nuclear translocation and binding to HSE (Heat Shock Element) thereby inducing de novo transcription of cytoprotective Heat Shock Proteins (HSP) including HSP27, HSP32 and HSP70.

Celastrol mechanism of action may further include 3) induction/amplification of protective signaling: Celastrol by stimulating ROS production may activate above described mechanisms thereby leading to activation of protective signaling pathways.

The use of the terms "a" and "an" and "the" and similar referents in the context of describing the invention (especially in the context of the claims) are to be construed to cover both the singular and the plural, unless otherwise indicated herein or clearly contradicted by context.

The terms "comprising", "having", "including", and "containing" are to be construed as open-ended terms (i.e., meaning "including, but not limited to") unless otherwise noted.

Recitation of ranges of values herein are merely intended to serve as a shorthand method of referring individually to each separate value falling within the range, unless otherwise indicated herein, and each separate value is incorporated into the specification as if It were individually recited herein. All subsets of values within the ranges are also incorporated into the specification as if they were individually recited herein.

Similarly, herein a general chemical structure with various substituents and various radicals enumerated for these substituents is intended to serve as a shorthand method of referring individually to each and every molecule obtained by the combination of any of the radicals for any of the substituents. Each individual molecule is incorporated into the specification as if it were Individually recited herein. Further, all subsets of molecules within the general chemical structures and all structures/molecules belonging to the same compound family are also incorporated into the specification as if they were individually recited herein.

Any and all combinations and subcombinations of the embodiments and features disclosed herein are encompassed by the present invention.

Herein, the term "about" has its ordinary meaning. The term "about" is used to indicate that a value includes an inherent variation of error for the device or the method being employed to determine the value, or encompass values close to the recited values, for example within 10% or 5% of the recited values (or range of values).

All methods described herein can be performed in any suitable order unless otherwise indicated herein or otherwise clearly contradicted by context.

The use of any and all examples, or exemplary language (e.g., "such as") provided herein, is intended merely to better illustrate the invention and does not pose a limitation on the scope of the invention unless otherwise claimed.

Unless otherwise defined, all technical and scientific terms used herein have the same meaning as commonly understood by one of ordinary skill in the art to which this invention belongs.

The present invention provides a method of Improving the resistance of cells to cell death (e.g., resistance to oxidative and/or hypoxic stress induced death, other physical or chemical or mechanical stressors including heat, oxidation, $H_2O_2$, hypoxia, encapsulation, etc.), said method comprising contacting the cells with an effective amount of one or more compounds that activate the HSF1 pathway and the NRF2 pathway. The present invention provides the use one or more compounds that activate the HSF1 pathway and the NRF2 pathway for improving the resistance of cells to cell death and improving cellular functionality.

The present invention also provides a method of improving the viability and retention of transplanted or transfused cells, said method comprising contacting the cells with an effective amount of one or more compounds that activate the HSF1 pathway and the NRF2 pathway prior to and/or after transplantation or transfusion.

The present Invention also provides a method of improving the therapeutic profile and functionality of stem cells (activation of beneficial proteins including growth factors, antioxidant enzymes, heat shock proteins, chemokines and anti-inflammatory cytokines for paracrine amelioration of transplant microenvironment), said method comprising contacting the stem cells with an effective amount of one or more compounds that activate the HSF1 pathway and the NRF2 pathway.

The present invention also provides a method of Identifying one or more compounds that may be useful for improving the resistance of cells to cell death (e.g., hypoxic and/or oxidative and/or hypoxia/reoxygenation stress-induced cell death) and/or improving the viability and retention of transplanted or transfused cells, said method comprising (i) contacting a cell with said one or more compounds; (H) determining whether the HSF1 pathway and the NRF2 pathway are activated in said cell, wherein activation of said pathway is indicative that said one or more compounds may be useful for improving the resistance of cells to cell death and/or improving the viability and retention of transplanted or transfused cells.

The present invention also provides a method of treating a subject in need of cell transplantation or transfusion, said method comprising (a) contacting the cells to be transplanted with an effective amount of one or more compounds that activate the HSF1 pathway and the NRF2 pathway; and (b) transplanting or transfusing the cells of (a) in said subject.

The expression "compound that activates the Heat shock factor protein 1 (HSF1) pathway" refers to any agent (small molecules, peptides, proteins, antibodies, oligomers, etc.) capable of directly or indirectly increasing the release of HSF1 from the chaperone repressor HSP90 complex and/or activating its translocation to the nucleus or increasing its cellular content, thus increasing HSF1-mediated transcription. It includes agents that antagonizes the co-chaperone(s) of HSP90, such as Cdc37 and p23, which results in dissociation/activation of HSF1 or HSF1 protein itself.

The expression "compound that activates the Nuclear factor (erythroid-derived 2)-like 2 (NRF2) pathway" refers to any agent (small molecules, peptides, antibodies, oligomers, etc.) capable of directly or indirectly increasing the release of NRF2 from the repressor Kelch-like ECH-associated protein 1 (KEAP1) and/or activating its translocation to the nucleus or increasing its cellular content, thus increasing NRF2-mediated transcription. KEAP1 comprises six Kelch repeats (residues 327-372, 373-423, 424-470, 471-517, 518-564 and 565-611) that mediate Interaction with NRF2. Residues 69-84, and more particularly residues 76-84, of NRF2 (which encompass the conserved ETGE motif), are involved in the interaction with KEAP1. Examples of compounds that activate the NRF2 pathway include Celastrol, tBHQ, CDDO, Camosol, Andrograpsholide, Cafestol, Sulforaphane, Curcumin, EGCG, Pyrithione, Resveratrol, Gedunin, Quercetin, bis(2-hydroxybenzylidene)acetone (2-HBA) or HBB2, 1,2-dithiole-3-thione (D3T), acetylenic tricyclic bis(cyano enone) (TBE31), Anthothecol, Whitanolides, and analogs thereof or members of alkaloid, quinones and quinone methide, gambogic acid, limonoids, rotenoids, terpenoids, furanoids, cathechins, alkenyls, carbohydrates, flavonoids, or aromatic families.

In an embodiment, the method comprises the use of one compound that activates both the HSF1 pathway and the NRF2 pathway. In another embodiment, the method comprises the use of two or more molecules that activate the HSF1 pathway and the NRF2 pathway, e.g. a first compound that activates the HSF1 pathway and a second compound that activates the NRF2 pathway, or a first compound that activates the HSF1 and NRF2 pathways and a second compound that activates only the NRF2 pathway, etc.

In an embodiment, the one or more compounds comprises Celastrol or an analog thereof, a compound of the withanolide family (e.g. Withanolide A, Withaferin A) or an analog thereof, a compound of the limonoid family (e.g., Gedunin) or an analog thereof, a curcuminoid (e.g., Curcumin) or an analog thereof, Sulforaphane or an analog thereof, sulphoxythiocarbamate alkyne (STCA) or an analog thereof, Novobiocin or an analog thereof, Lonidamine or an analog thereof, Gamendazole or an analog thereof, a Bardoxolone/CDDO compound (e.g. CDDO-Im) or an analog thereof, tert-Butylhydroquinone (tBHQ) or an analog thereof, (1E, 4E)-1,5-Bis(2-Hydroxyphenyl)-1,4-pentadien-3-one (HBB2) or an analog thereof, acetylenic tricyclic bis(cyano enone) (TBE-31) or an analog thereof, epigallocatechin gallate (EGCG) or an analog thereof, or any combination thereof. The term "analog" as used herein refers to a compound having the basic or backbone structure of the reference compound, but comprising one or more modifications (e.g., bond order, absence or presence of one or more atoms and/or groups of atoms, and combinations thereof) that do not abolish the biological activity on the HSF1 pathway and/or the NRF2 pathway. For example, Celastrol analogs (pentacyclic triterpene compounds) are described in Klaic et al., *ACS Chem Biol.* 2012 May 18; 7(5): 928-937 and PCT publication No. WO2015/148802.

In an embodiment, at least one of the one or more compounds is an HSP90 inhibitor, an HSP90 N or C-terminal Inhibitor, preferably an HSP90 co-factor Inhibitor.

In an embodiment, at least one of the one or more compounds has NRF2 inducing activity.

In an embodiment, a combination of compounds having improved (e.g., synergistic) activity relative to activity of the compounds used alone are used. Examples of combinations of compounds include (i) (a) Celastrol or an analog thereof; and (b) EGCG or an analog thereof; (ii) (a) Celastrol or an analog thereof; and (b) tBHQ or an analog thereof; (Iii) (a) Gedunin or an analog thereof; and (b) EGCG or an analog thereof; (iv) (a) Gedunin or an analog thereof; and (b) tBHQ or an analog thereof; (v) (a) Celastrol or an analog thereof; and (b) 2HBA or an analog thereof; (vi) (a) Celastrol or an analog thereof; and (b) Curcumin or an analog thereof; or (vii) a) Celastrol or an analog thereof; and (b) Camosol or an analog thereof.

As used herein the term "adjunct agent" refers an agent that may increase cell survival, viability or resistance to stress or damages. An "adjunct agent" may be capable of modulating for example cell phenotype and may Include antioxidants and NRF2 activators. Adjunct agents include for example, 2HBA, andrograpsholide, ascorbic acid, cafestol, camosolbardoxolone-imidazole (CDDO-im), chalcone, N6-[2-[[4-(2,4-dichlorophenyl)-5-(1H-imidazol-2-yl)-2-pyrimidinyl]amino]ethyl]-3-nitro-2,6-pyridinediamine (CHIR98014), conglobatin, curcumin, cycloastragenol, 1,2-dithiole-3-thione (D3T), doramapimod, edaravone, EGCG, gambogic acid, ganetespib, gedunin, IQ-1, limonin, lonidamide, melatonin, benzamide tetrahydroindolones, N886, alkylamino biphenylamides, novobiocin, pyridoxal 5'-phosphate (P5'-P), pyrithione, quercetin, radicicol, resveratrol, N-(2-cyano-3,12-dioxo-28-noroleana-1,9(11)-dien-17-yl)-2,2-difluoro-propanamide or omaveloxolone (RTA-408), 4-(4-Fluorophenyl)-2-(4-hydroxyphenyl)-5-(4-pyridyl)-1H-imidazole (SB202190), 3-(2,4-Dichlorophenyl)-4-(1-methyl-1H-indol-3-yl)-1H-pyrrole-2,5-dione (SB216763), SNX-5422 (PF-04929113), sodium Butyrate, sulforane, tetrabromobenzotriazole (TBB), tert-butylhydroquinone (tBHQ), valporic acid, withaferin A, ergosterols, lupenones and analogs of any such adjunct agents.

As used herein the term "secretome" refers to secreted organic molecules and/or inorganic elements by biological cells, tissues, organs, and organisms.

As used herein the expression "modulating the state of a cell" means a change in the cellular phenotype, in the pattern of expression of certain genes or in the pattern of secretion of certain proteins.

The expression straight alkyl group of 1 to 6 carbon atoms (i.e., C1-C6 alkyl) as used herein means saturated monovalent hydrocarbon radicals having straight or branched moieties and containing from 1 to 6 carbon atoms. The term "branched alkyl group" refers to alkyl group that include one or more tertiary or quaternary carbon atoms.

The alkyl group may be substituted (OH, NH2, I, F, Cl, Br, CN) unsubstituted. Examples of such groups include, but are not limited to, methyl, ethyl, propyl, iso-propyl, n-butyl, iso-butyl, and tert-butyl.

As used herein, the term "substituted" refers to a group in which one or more hydrogen atoms in the group are, independently, replaced with a substituent selected from methyl, ethyl, n-propyl, isopropyl, hydroxy, methoxy, ethoxy, fluorine, chlorine, bromine, iodine, cyano, nitro, amino, alkylamino, dialkylamino, carboxy, chloromethyl, trichloromethyl, trifluoromethyl, methoxyethyl and the like.

As used herein the term "lower alkyl group of 1 to 3 carbon atoms" refers to methyl, ethyl, propyl.

In an embodiment, the one or more compounds are present in a pharmaceutical composition that further comprises one or more pharmaceutically acceptable carriers, excipient, and/or diluents. As used herein, "pharmaceutically acceptable" (or "biologically acceptable") refers to materials characterized by the absence of (or limited) toxic or adverse biological effects in vivo. It refers to those compounds, compositions, and/or dosage forms which are, within the scope of sound medical judgment, suitable for use in contact with the biological fluids and/or tissues and/or organs of a subject (e.g., human, animal) without excessive toxicity, irritation, allergic response, or other problem or complication, commensurate with a reasonable benefit/risk ratio.

The term "pharmaceutically acceptable carriers, excipient, and/or diluents" refers to additives commonly used in the preparation of pharmaceutical compositions and includes, for example, solvents, dispersion media, saline solutions, surfactants, solubilizing agents, lubricants, emulsifiers, coatings, antibacterial and antifungal agents, chelating agents, pH-modifiers, soothing agents, buffers, reducing agents, antioxidants, isotonic agents, absorption delaying agents or the like (see, e.g., Rowe et al., *Handbook of Pharmaceutical Excipients*, Pharmaceutical Press; $6^{th}$ edition, 2009).

In an embodiment, the one or more compounds may be combined/mixed with scaffold materials for cell transplantation/tissue engineering, e.g., biomaterials, polymers and/or matrixes commonly used as scaffold for stem cells.

The one or more compounds may be formulated for administration via any conventional route, such as intravenous, oral, transdermal, intraperitoneal, subcutaneous, mucosal, Intramuscular, Intranasal, Intrapulmonary, parenteral or topical administration. The preparation of such formulations is well known in the art (see, e.g., *Remington: The Science and Practice of Pharmacy*, Lippincott Williams & Wilkins; $21^{st}$ edition, 2005).

Also, as shown in the Examples below, the medium (e.g., secretome) from cells treated with the one or more compounds was able to confer protection against death, and thus in an embodiment the methods described herein comprises culturing a population of cells (e.g., mesenchymal stem cells, CD133$^+$ cells, pancreatic cells, renal cells, epithelial and endothelial cells) In the presence of the one or more compounds, collecting the medium or supernatant from said culture; and contacting cells in the presence of said medium or supernatant.

In an embodiment, the cell is a stem/pluripotent/progenitor cell or differentiated cell, for example an hematopoietic stem cell (HSC), an hematopoletic progenitor cells (HPCs), a multipotent progenitor cell (MPP), a lymphoid progenitor cell, a myeloid progenitor cell, a mesenchymal stem cell (MSC), an adipose derived stem cell (ADSC), etc. In another embodiment, the cell is a differentiated cell.

The starting population of cells may be obtained from the body or an organ of the body containing suitable cells. The cells collected can be enriched for cells having certain characteristics in ways known to those of skill in the art, for example based on expression of certain markers (e.g., CD34$^+$, CD133$^+$). Moreover, the starting cell population may be used directly or frozen and stored for use at a later point in time. Thus, the cell population may first be subjected to enrichment or purification steps, including adhesion to plasticware or negative and/or positive selection of cells based on specific cellular markers in order to provide the starting cell population, for example to provide a starting cell population enriched in MSCs. Methods for isolating said starting cell population based on specific cellular markers may use fluorescent-activated cell sorting (FACS) technology or solid or insoluble substrate to which Is bound antibodies or ligands that interact with specific call surface markers. For example, cells may be contacted with a solid substrate (e.g., column of beads, flasks, magnetic particles) containing the antibodies and any unbound cells are removed. When a solid substrate comprising magnetic or paramagnetic beads is used, cells bound to the beads can be readily isolated by a magnetic separator (e.g. magnetic cell sorting, MACS®, CliniMacs® product line by Miltenyi Biotec®).

The cells may be cultured in media suitable for the maintenance, growth, or proliferation of the cells either in normal culture conditions of bioreactors for large scale manufacturing for example. The culture conditions of the population of cells will vary depending on different factors, notably, the starting cell population. Suitable culture media and conditions are well known in the art. The method of the present invention may be carried out in natural medium, a semi-synthetic medium or a synthetic medium in terms of composition, and may be a solid medium, a semisolid medium or a liquid medium in terms of shape, and any nutrient medium or defined medium used for cell culture, which may be supplemented with one or more suitable factors. Such medium typically comprises sodium, potassium, calcium, magnesium, phosphorus, chlorine, amino acids, vitamins, cytokines, hormones, antibiotics, serum, fatty acids, saccharides or the like. In the culture, other chemical components or biological components may be incorporated singly or in combination, as the case requires. Such components to be incorporated in the medium may be fetal calf serum, human serum, horse serum, insulin, transferrin, lactoferrin, cholesterol, ethanolamine, sodium selenite, monothioglycerol, 2-mercaptoethanol, bovine serum albumin, sodium pyruvate, polyethylene glycol, various vitamins, various amino acids, agar, agarose, collagen, methylcellulose, various cytokines, various growth factors or the like. The media may be chemically defined, serum-free and/or xeno-free.

During or following treatment with the one or more compounds, the cells may be cultured under conditions suitable for their maintenance, growth and/or proliferation.

The amount of the one or more compounds used to mediate the above-noted effects may be determined by the skilled person. In an embodiment, the concentration is about 1 nM to about 1 mM, about 10 nM to 100 µM, or about 100 nM to about 10 µM.

Concentrations of $10^{-5}$ M to $10^{-10}$ M (including individually, from 1 uM to 10 uM, from 5 uM to 10 mM) are also encompassed by the present Invention.

In an embodiment, the above-noted contacting comprises the addition of a single dose or multiple doses of the one or more compounds in the culture medium.

The treatments with compounds may be administered in vivo, in the patient and cells, tissues, organs, and then may be collected as described above The cell population may then be washed to remove the one or more compounds and/or any other component of the cell culture and resuspended in an appropriate cell suspension medium, either washed off or left in contact for short term use or in a long-term storage medium, for example a medium suitable for cryopreservation.

Subjects that may benefit from transplantation/transfusion of cells, and more particularly stem cells, include subjects suffering from heart failure, stenocardia, cardiac infarction (e.g., heart/cardiac ischemia), arrhythmia, valvular heart diseases, myocardial/pericardial diseases, congenital heart diseases (e.g., atrial septal defect, ventricular septal defect, arterial duct patency, tetralogy of Fallot), arterial diseases (e.g., arterial sclerosis, aneurysm, etc.). venous diseases (e.g., phlebeurysm), critical limb or organ ischemia (hepatic ischemia, etc.), degenerative joint disease, osteoarthritis, rheumatoid arthritis, bone disorders (e.g., osteitis, osteoporosis, osteoarthritis, osteosarcoma), skin disorders (e.g., psoriasis, eczema, skin cancer), corneal diseases (e.g., keratoconus, keratitis), liver diseases (e.g., acute and chronic liver failure, hepatitis, genetic deficiency including urea cycle disorder), lung diseases (e.g., COPD, ARDS, pneumonitis), kidney diseases (e.g., CKD), musculoskeletal injuries, tendinitis, systemic disease (e.g. sepsis), cancer, disorders, degenerative diseases including CNS diseases (e.g. Alzheimers, Parkinsons, Dementia, ALS) and spinal injuries.

The one or more compounds may be used in combination with other therapies/drugs used for the treatment of the above-mentioned diseases/disorders/conditions. The one or more compounds may be administered or co-administered (e.g., consecutively, simultaneously, at different times) in any conventional dosage form. Co-administration in the context of the present invention refers to the administration of more than one therapeutic in the course of a coordinated treatment to achieve an improved clinical outcome. Such co-administration may also be coextensive, that is, occurring during overlapping periods of time. For example, the one or more compounds may be administered to the subject before, concomitantly, before and after, or after the additional active agent or therapy is administered. The active agents (e.g., the one or more compounds and the additional active agent) may in an embodiment be combined/formulated in a single composition and thus administered at the same time.

Any suitable amount of the one or more compounds or pharmaceutical composition comprising same may be administered to a subject. The dosages and frequency of administration will depend on many factors including the mode of administration. For the prevention, treatment or reduction in the severity of a given disease or condition, the appropriate dosage of the one or more compounds/composition will depend on the type of disease or condition to be treated, the severity and course of the disease or condition, whether the compound/composition is administered for preventive or therapeutic purposes, previous therapy, the patient's clinical history and response to the compound/composition, and the discretion of the attending physician. The compound/composition is suitably administered to the patient at one time or over a series of treatments. Preferably, it is desirable to determine the dose-response curve in vitro, and then in useful animal models prior to testing in humans. The present invention provides dosages for the compounds and compositions comprising same. For example, depending on the type and severity of the disease, about 1 µg/kg to to 1000 mg per kg (mg/kg) of body weight per day. Further, the effective dose may be about 0.1 mg/kg, 0.2 mg/kg, 0.3 mg/kg, 0.4 mg/kg, 0.5 mg/kg, 1 mg/kg, 5 mg/kg, 10 mg/kg, 15 mg/kg, 20 mg/kg/25 mg/kg, 30 mg/kg, 35 mg/kg, 40 mg/kg, 45 mg/kg, 50 mg/kg, 55 mg/kg, 60 mg/kg, 70 mg/kg, 75 mg/kg, 80 mg/kg, 90 mg/kg, 100 mg/kg, 125 mg/kg, 150 mg/kg, 175 mg/kg or 200 mg/kg, and may Increase by 25 mg/kg increments up to 1000 mg/kg, or may range between any two of the foregoing values. A typical daily dosage might range from about 1 µg/kg to 100 mg/kg or more, depending on the factors mentioned above. For repeated administrations over several days or longer, depending on the condition, the treatment is sustained until a desired suppression of disease symptoms, or clinical endpoint, occurs. The one or more compounds may be administered at the appropriate frequency, e.g., once, once-a-day, twice weekly, weekly, every two weeks, every month However, other dosage regimens may be useful. The progress of this therapy is easily monitored by conventional techniques and assays. These are simply guidelines since the actual dose must be carefully selected and titrated by the attending physician based upon clinical factors unique to each patient. The optimal dose will be determined by methods known in the art and will be Influenced by factors such as the age of the patient and other clinically relevant factors. In addition, patients may be taking medications for other diseases or conditions.

Similarly, when pre-conditioned cells are administered to a patient, the number of cells transfused will take into consideration factors such as sex, age, weight, the types of disease or disorder, stage of the disorder, the percentage of the desired cells in the cell population and the amount of cells needed to produce a therapeutic benefit. In one particular embodiment, the composition is administered by intravenous infusion and comprises at least about $1 \times 10^4$ cells/kg or at least about $1 \times 10^5$ cells/kg, for example from about $1 \times 10^4$ cells/kg to about $1 \times 10^8$ cells/kg or from about $1 \times 10^4$ cells/kg to about $1 \times 10^7$ cells/kg.

The subjects that may be treated using the methods described herein are mammals, including, but not limited to, cows, sheep, goats, horses, dogs, cats, guinea pigs, rats, monkeys or other bovine, ovine, equine, canine, feline, rodent or murine species, primates, and preferably a human being, male or female.

Other applications of the methods described herein Include, for example, preservation of tissues, grafts (e.g., vascular grafts) and ex vivo organ perfusions (e.g. lung perfusion (EVLP)).

MODE(S) FOR CARRYING OUT THE INVENTION

The present invention is illustrated in further details by the following non-limiting examples.

Example 1: HSP90-Cochaperone Inhibitors as Cell Conditioning Agents

In an attempt to identify conditioning compounds that are able to ensure in vivo cellular viability, based on preliminary evidence using Celastrol, over a dozen compounds with structural similarities identified through literature and the Sigma-Aldrich® Structure Search online tool, were screened. The compounds' capacity to improve viability of human MSCs challenged to hypoxic stress was measured. The molecules that were screened, most of which are natural compounds, can be classified as triterpenoids, limonoids, with anolides, sterols, isoprenoides/diterpenes and flavonoids. Classical HSP90 inhibitors were also added to the screen, such as Radicicol that directly target the ATP binding pocket at the NT region of HSP90[9] (NT inhibitor). The screens have shown variable efficacy of compounds in enhancing viability of cells during hypoxic stress (FIG. 1: A, B) and in their capacity to induce HSP expression as seen by reporter based assays (FIG. 1C). For some of the top scoring compounds including with anolides and Gedunin that share structural similarities with Celastrol, emerging evidence shows that many of these efficient conditioning compounds belong to HSP90 modulator families targeting the HSP90 cochaperone interaction[10][11][12].

Figures 3, 4:
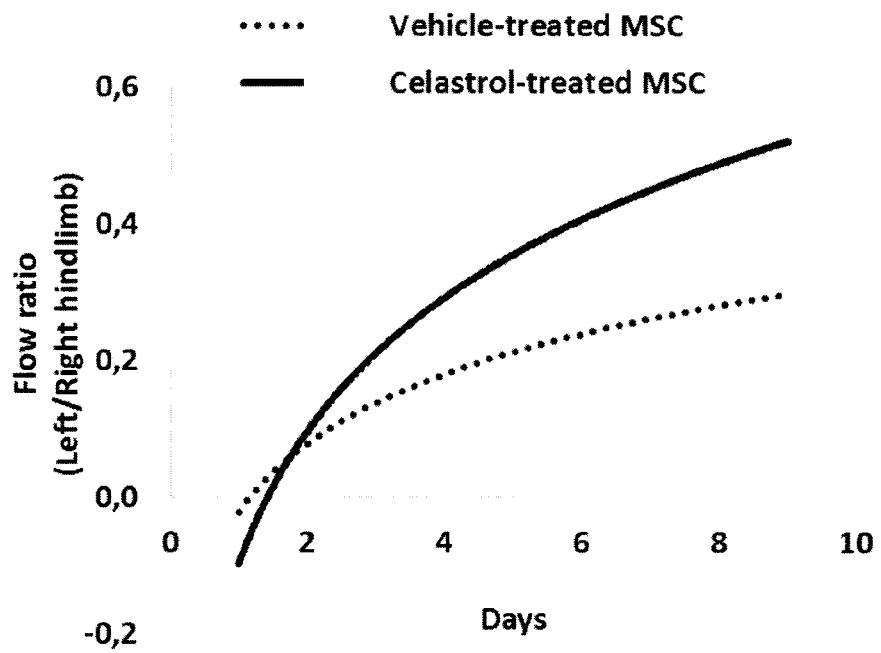
FIG. 3 shows that Celastrol pre-conditioning enhances stem cell therapeutic effect. Celastrol pre-conditioned MSC reestablish blood flow more efficiently in hindlimb ischemia model as seen by laser doppler scanning.
FIG. 4 shows cytoprotective proteins, growth/survival factors and antioxidant proteins released by human mesenchymal stem cells (hMSC) after one hour of Celastrol ($10^{-6}$ M) treatment. Conditioned cell media was collected, concentrated, proteins were separated by gel electrophoresis and analyzed by mass spectrometry and Identified through database search.

Example 2: Celastrol Enhances Transplanted Cell Retention In Vivo and Enhances Paracrine Secretion The results described below show that Celastrol Increases in vivo viability and retention of transplanted cells. Briefly, rat MSCs were treated in suspension with conditioning compounds for 60 minutes. Cells were then washed, labeled with fluorescent cell tracker and injected at t=0 in rat left ischemic hindlimb. Transplanted cells were imaged in vivo until day 9 using Optix™ MX3 Molecular Imaging System from ART (FIG. 2: A,B). The results show improved in vivo viability and retention of pre-treated stem cells, which translates Into a trend for improved blood flow reestablishment as seen through laser Doppler scanning (FIG. 3). Proteomic analysis shows that Celastrol treatment of human MSC preserves and enhances stem cell functionality as seen by Increased levels of heat shock protein (HSP90a by 7,0-fold; HSP90b by 2,2-fold; HO1 by 2,2-fold; HSP70 by 1,8-fold), growth factor and cytokine (MCSF by 24.4 fold, HGF by 2,1-fold) and antioxidant response related genes (GSH by 2,8-fold, TRX by 2,5-fold, CAT by 1,7-fold) in the culture media (FIG. 4).

Briefly, rat MSCs were incubated with low serum media (αMEM 1X, 1% (Fetal Bovine Serum (FBS), 1% Penicillin-Streptomycin (P-S)) containing either Celastrol (10E-6M-10E-8M) or Vehicle (Dimethyl sulfoxide (DMSO)) for one hour. The media is then aspirated, cells are washed with 3 changes of media (αMEM 1X, 1% FBS, 1% P-S). Cells are trypsinated and stained with Vybrant CFDA (Thermo Fisher Scientific) according to the manufacturer's protocol that allows detection in fluorescent imaging (Optix MX2). Cells are then counted using the Countess II FL automated cell counter (Thermo Fisher Scientific) and 3 million viable MSC'c are injected in the ischemic rat hindlimb model, using a 26G needle and syringe at 5 different points in 200 ul total volume.

Sprague-Dawley rats (CD CRL: Charles River) are anesthetized (isoflurane 2.5-3.0% (Abbott Laboratories, Abbott Park, IL), 1 L/min oxygen) and bupivicaine is injected into the thigh (2 mg/kg sc qd) at the site of the Incision. The left common femoral artery Is cleared and the distal portion of the saphenous artery and all collateral branches and veins are dissected. The proximal and distal portion of the artery between the inguinal ligament and the knee is excised. Thus, none of the branches of the femoral artery can form collaterals. The lower right limb of each animal Is kept Intact and serves as a control. The wound Is closed using Vicryl 5-0. The animal receives buprenorphine hydrochloride (0.05 mg/kg s.c. bid 3 days) and is placed in its cage on Diamond soft litter. The day after the surgical procedure, PBS or MSCs pretreated with the vehicle or experimental compound are injected. The animals are anesthetized (isoflurane 2.5-3.0% (Abbott Laboratories, Abbott Park, IL), 1 L/min oxygen) and the cells are Injected directly into the quadriceps with a 26G needle and syringe at 5 different points.

Transplanted cells were imaged in vivo until day 9 using Optix™ MX3 Molecular Imaging System from ART and in parallel, rats undergo Doppler scanning (Moor instruments) of the hindlimb which allows to study the recovery of the blood flow (below the knee) in a model of ischemia of the lower rat limb (n=3) after transplantation of conditioned rMSC.

Celastrol conditioned cells increase viability and retention of stem cells implanted in the rat Ischemic hindlimb and ameliorate compared to vehicle treated cells the progressive recovery (as seen in a logarithmic pattern) the blood flow in the affected limb.

Example 3: Identification of Stem Cell Pharmaco-Optimizers

Criteria for Identifying Stem Cell Pharmaco-Optimizers

The criteria for identifying stem cell pharmaco-optimizers rely on the ability of the treatment to preferably satisfy two main conditions:
1. Treatment of cells would preferably confer an Increased in vivo viability and retention profile especially in the context of stem cell transplantation in hypoxic and/or oxidative microenvironments as observed in ischemic tissues; and
2. Treatment of cells would preferably allow maintenance of normal cellular phenotype and/or functionality as much as possible. However, highly desirable pharmaco-optimizers may also enhance cellular functions to promote a beneficial or therapeutic phenotype. In the case of stem cells, tissue repair involving paracrine activities, the pharmaco-optimizers may preferably enhance secretion of beneficial proteins and/or reduce production of deleterious proteins, thereby having a favourable balance and Impact on the transplant environment.

Methods to Test Candidate Stem Cell Pharmaco-Optimizers

To test the first main condition, MSCs (either sourced from rat or humans) were treated with the candidate pharmaco-optimizers, washed and submitted to hypoxia/serum starvation (<1% $O_2$ in hypoxia chamber in low serum media for 48-72 hours) or oxidative stress (incubation in media for 1 hour spiked with 0-2 mM $H_2O_2$), which mimic the major lethal stressors present in the ischemic transplant microenvironment. Viability status of cells are assessed using the LIVE/DEAD viability/cytotoxicity kit (Life Technologies™) and results are quantified by Operetta high content screening (HCS) apparatus equipped with Harmony automated analysis software (Perkin Elmer™).

To test the second main condition, MSCs were treated with the candidate pharmaco-optimizers for 1 hour, followed by 3 hours washout period. Cell mRNA was extracted and expression of genes of interest was quantified by real time PCR. In additional MSC cultures, cells were treated for one hour, washed and cultured in low serum media for 24 hours. The media containing paracrine factors secreted by MSCs was then placed in contact with H9c2 cardiomyoblast cell line. H9c2 cells were then submitted to the hypoxia/serum starvation (<1% $O_2$ in hypoxia chamber in low serum media for 48 hours) or oxidative stress (incubation in media for 1 hour spiked with 0-1 mM $H_2O_2$). Viability status of H9c2 cells was evaluated using the LIVE/DEAD assay as detailed above.

In order to identify the mechanisms responsible for the protection of conditioned MSC and for the protection afforded to H9c2 via paracrine mechanism when incubated with conditioned MSC media, various molecules were selected as conditioning agents targeting two major cellular pathways, namely the heat shock pathway through HSP90 targeting (HSF1 activation) and/or the Nuclear factor (erythroid-derived 2)-like 2 (NRF2) pathway.

Figure 5:
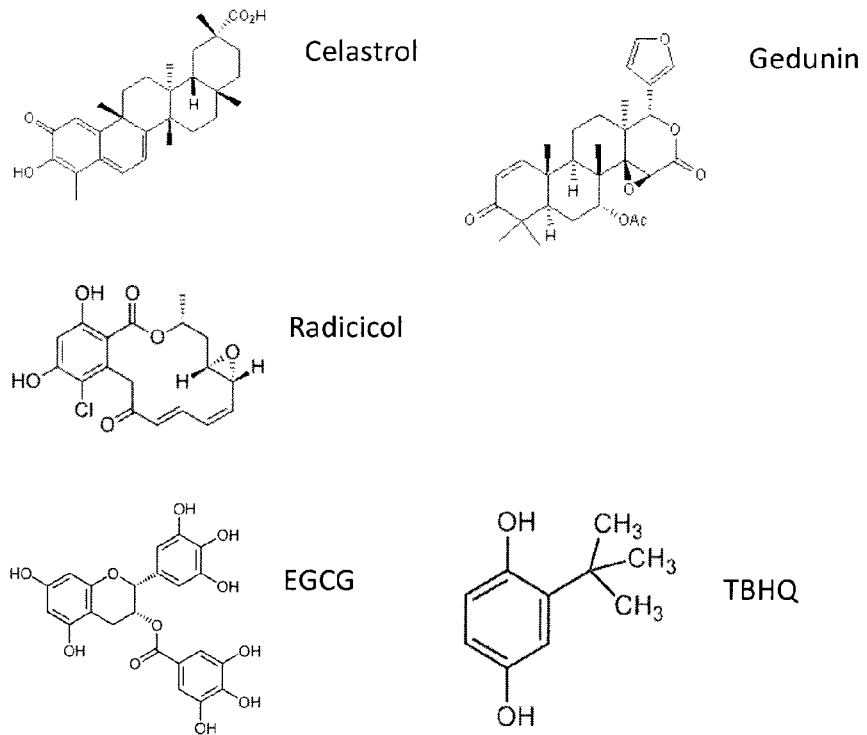
FIG. 5 shows some compounds used in experiments described herein (FIG. 6-22).
Figure 6:
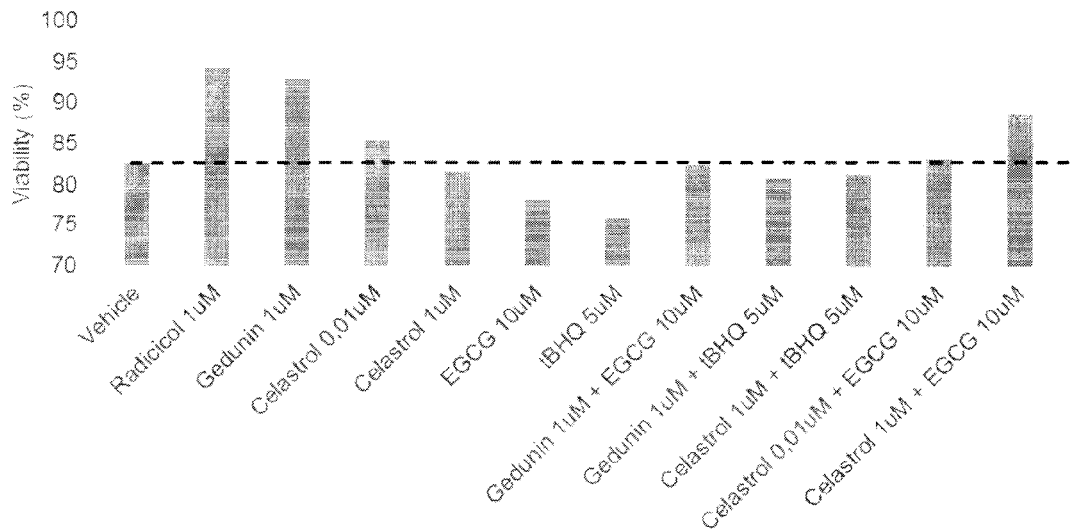
FIG. 6 shows that a 1-hour treatment of rat mesenchymal stem cells (rMSC) with HSP90 inhibitors (Celastrol, Gedunin, Radicicol) but not NRF2 activators alone (EGCG, tBHQ) protect rMSCs from 48-hour hypoxia induced cell death. EGCG potentiates Celastrol-mediated protection.
Figure 7:
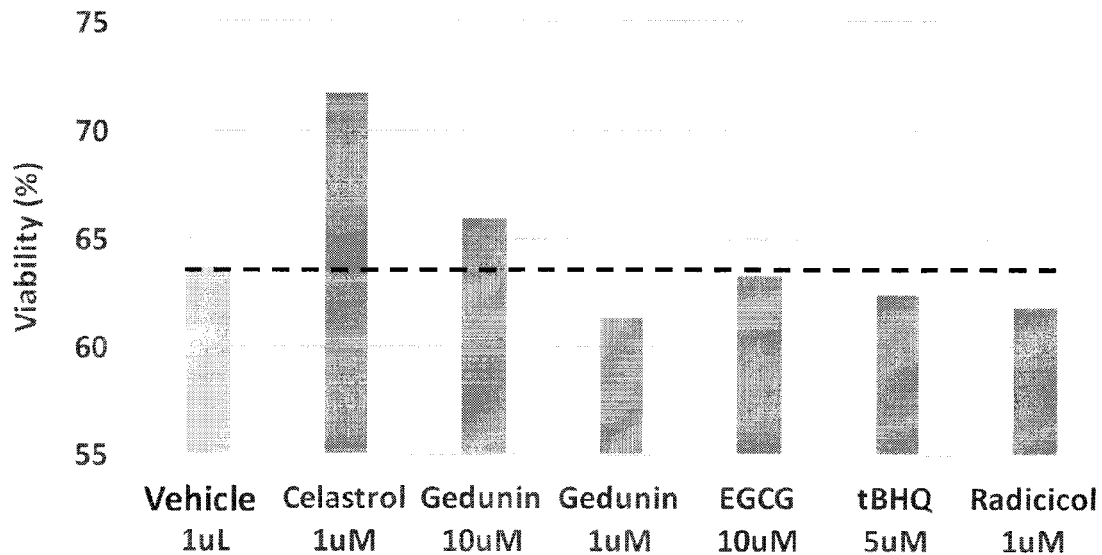
FIG. 7 shows that a 48-hour pre-conditioning of H9c2 with media from rMSC treated with HSP90 co-factor inhibitor (Celastrol; Gedunin high dose) protects H9c2 from 48-hour hypoxia-induced cell death.
Figure 8A:
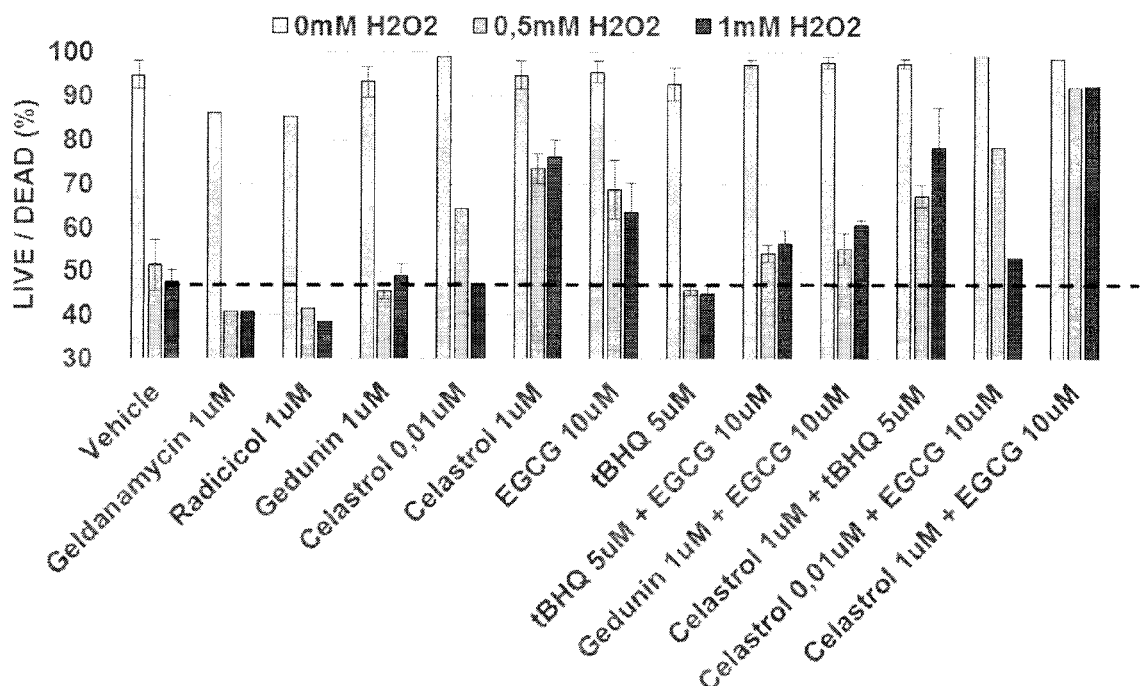
FIG. 8A shows that a 1-hour treatment of rMSC with NRF2 activating compounds (Celastrol, EGCG) but not essentially HSF1 activators (Geldanamycin, Radicicol) protect rMSCs from oxidative stress induced death. EGCG potentiates Celastrol-induced protection.

Tested compounds (FIG. 5):
  Celastrol: Potent HSF1 activator (HSP90-cofactor inhibition); NRF2 activator
  Gedunin: HSF1 activator (HSP90-cofactor inhibition); NRF2 activator
  Radicicol: HSF1 activator (HSP90 classical ATP inhibitor); no reported NRF2 activity
  EGCG: No reported HSF1 activation (HSP90-CT inhibition); NRF2 activator
  tBHQ: No reported HSF1 activation; NRF2 activator The results of these experiments, which are reported in FIGS. 6 to 9, may be summarized as follows:
  Compounds capable of HSF1 induction (Celastrol, Gedunin, Radicicol) protect cells from hypoxia Induced death (FIG. 6);
  HSP90 co-factor Inhibitors (Celastrol, Gedunin) produce a mediator for paracrine efficacy (FIG. 6, 7);
  HSP90 NT inhibitor (Radicicol) does not produce a mediator for paracrine efficacy (FIG. 7);
  HSP90 CT inhibitor (EGCG) does not protect treated cells from hypoxia, but produces additive effect on Celastrol-induced protection. (FIG. 6);
  NRF2 activators (EGCG, Gedunin, Celastrol) protect treated cells from oxidative stress-induced death. EGCG produces additive effect on Celastrol-induced protection (FIG. 8); and
  NRF2 activators (EGCG, tBHQ, Gedunin) except for Celastrol produce a paracrine mediator for protection against oxidative stress-induced death (FIG. 9).

Taken together, these results demonstrate that an optimal pharmaco-conditioning treatment for enhancement of cell viability combines the activity of an HSP90 co-factor inhibitor capable of HSF1 induction (resilience to hypoxia-induced death through direct and paracrine effect) and of an antioxidant NRF2 pathway inducer (resilience to oxidative stress-induced death through direct and paracrine effect). It was discovered that EGCG enhances Celastrol-stimulated cell protection.

In addition to viability enhancement (first criteria for stem cell pharmaco-optimizer selection), the enhancement of the expression profile (second criteria for stem cell pharmaco-optimizer selection) through quantification of mRNA expression of HSPs, growth factors (GF), antioxidant proteins/enzymes and cytokines Implicated in inflammation was assessed. Mono and combination treatments were tested.

Combination Treatments Tested—First Experiment:
  Celastrol (1 µM) or Gedunin (1 µM)+EGCG (1 µM, 10 µM) or TBHQ (1 µM, 5 µM)

Figure 10:
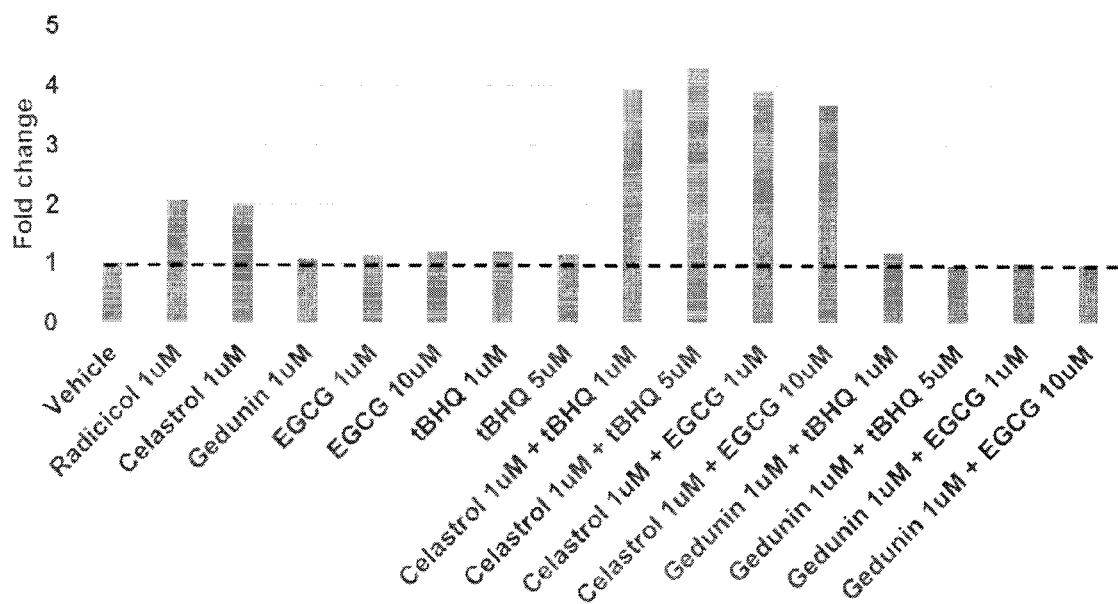
FIG. 10 shows HSP70 mRNA expression in rMSC following 1-hour treatment and 3-hour washout. EGCG and tBHQ produce synergistic increase of Celastrol-induced HSP70 expression.
Figure 11:
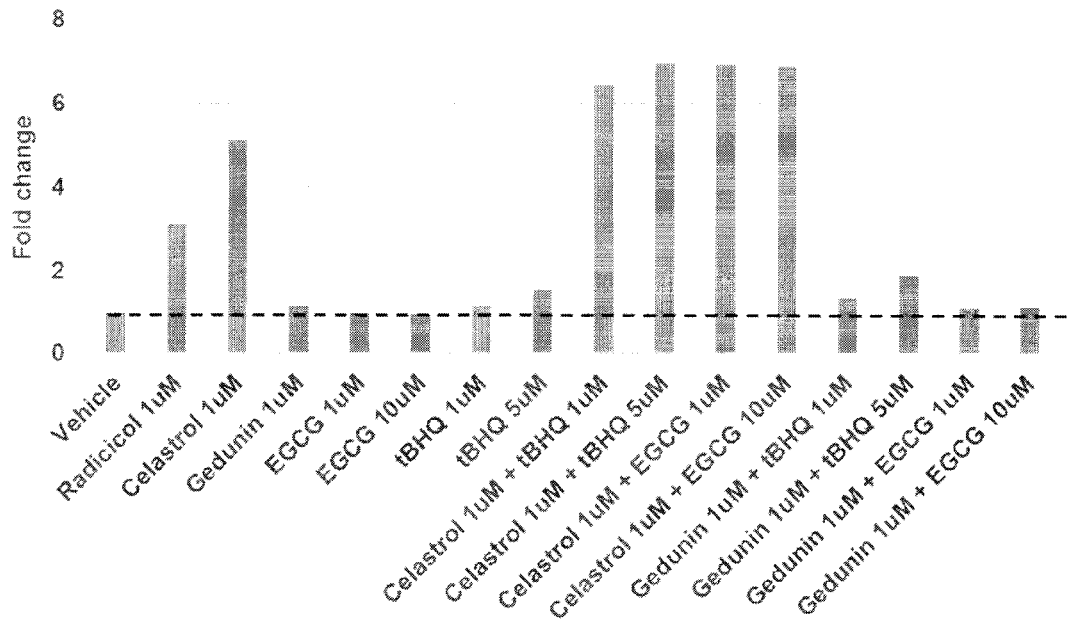
FIG. 11 shows HSP32 (HO-1) mRNA expression in rMSC following 1-hour treatment and 3-hour washout. EGCG and tBHQ produce synergistic Increase of Celastrol-induced HSP32 expression.
Figure 12:
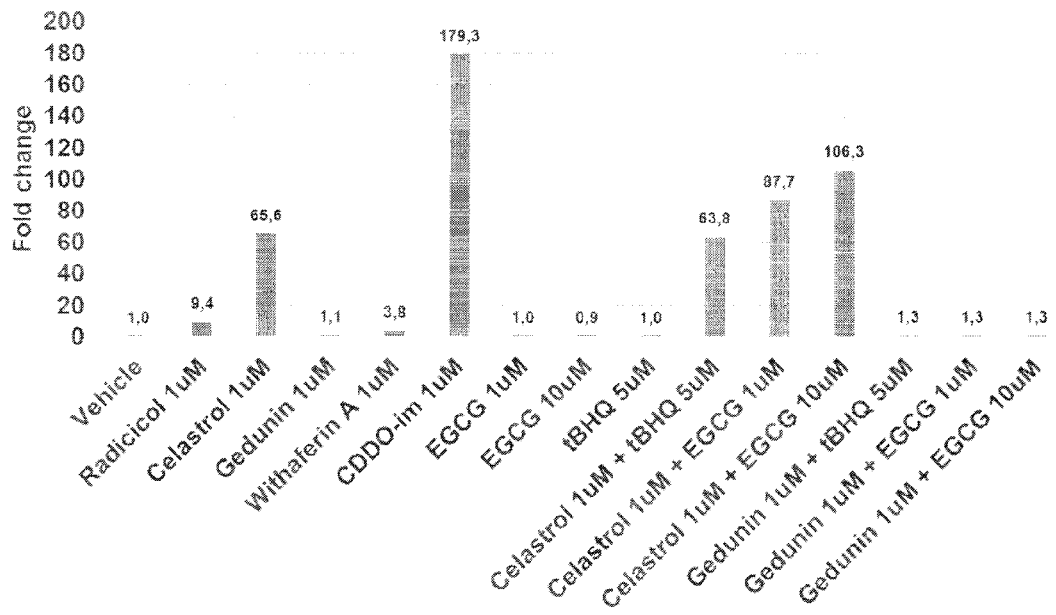
FIG. 12 shows HSP70 mRNA expression in human MSC (hMSC) following 1-hour treatment and 3-hour washout. EGCG produces synergistic increase of Celastrol-induced HSP70 expression.
Figure 13:
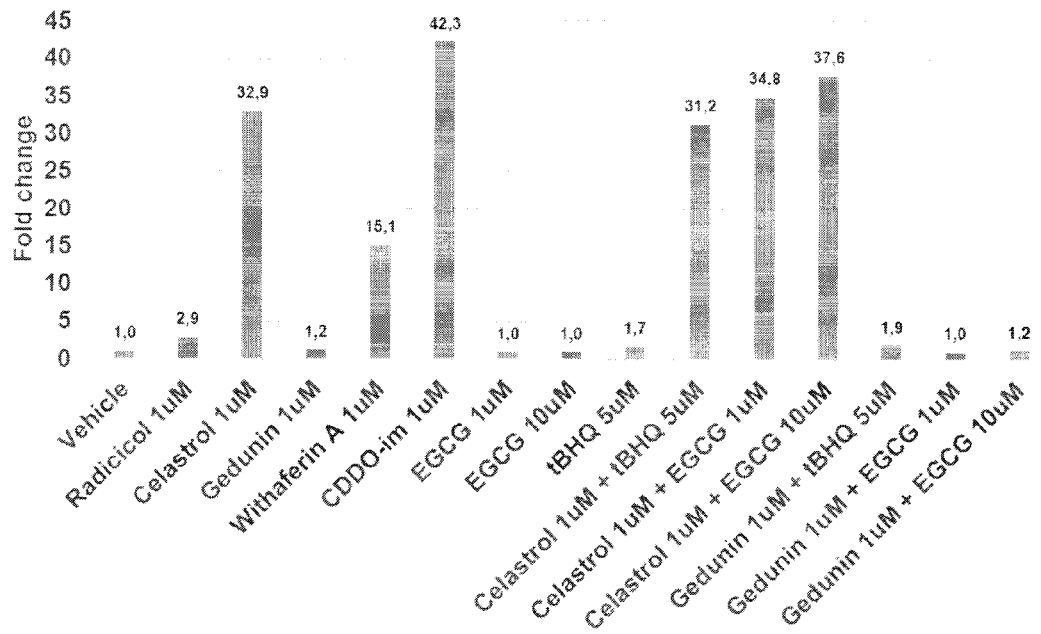
FIG. 13 shows HSP32 (HO-1) mRNA expression in human MSC (hMSC) following 1-hour treatment and 3-hour washout. EGCG produces synergistic increase of Celastrol-induced HSP32 expression.
Figure 14:
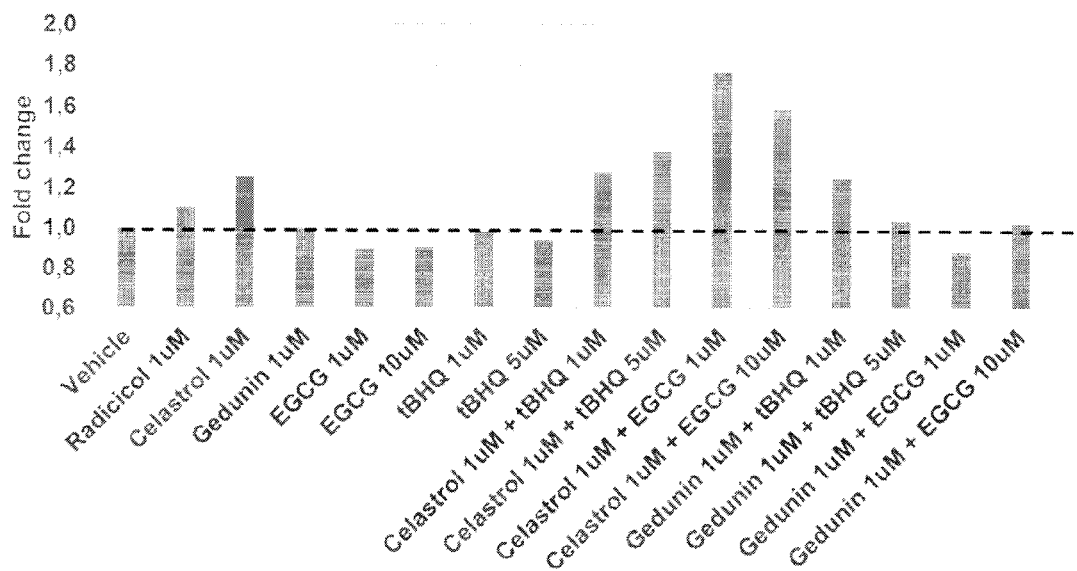
FIG. 14 shows FGF2 mRNA expression in rMSC following 1-hour treatment and 3-hour washout. EGCG and tBHQ produce synergistic increase of Celastrol-induced FGF2 expression. The combination of TBHQ and Gedunin also increased FGF2 mRNA expression.
Figure 15:
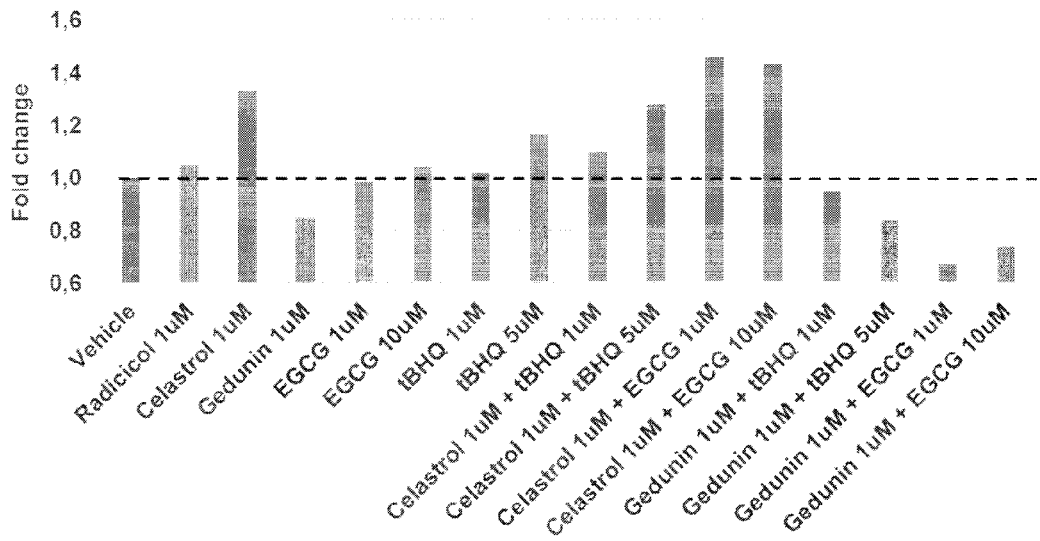
FIG. 15 shows VEGFα mRNA expression in rMSC following 1-hour treatment and 3-hour washout. EGCG produces synergistic increase of Celastrol-induced VEGF expression.
Figure 16:
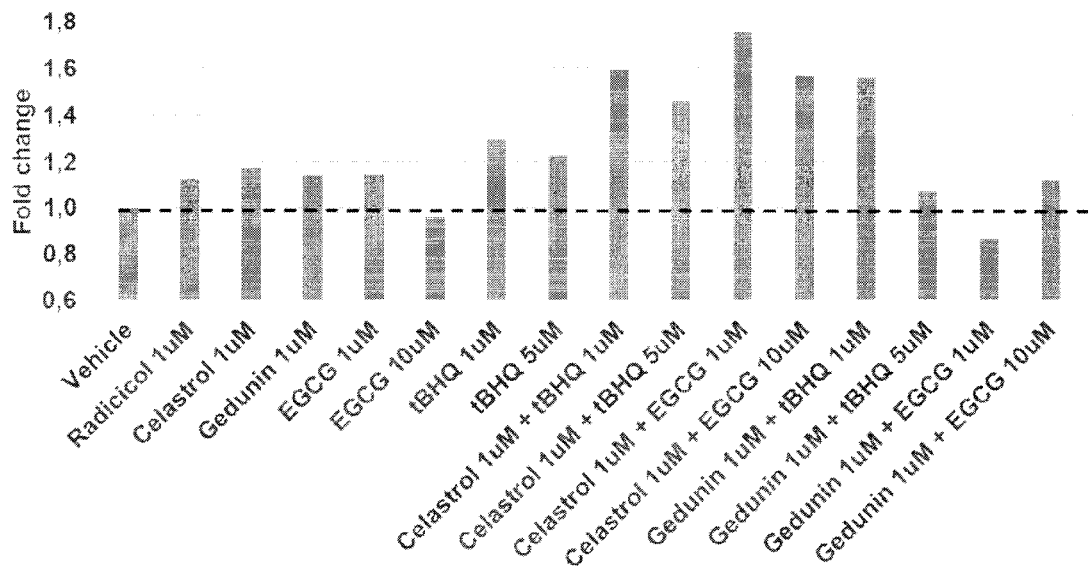
FIG. 16 shows Catalase (CAT) mRNA expression in rMSC following 1-hour treatment and 3-hour washout. EGCG and tBHQ produce synergistic increase of Celastrol-induced CAT expression.
Figure 17:
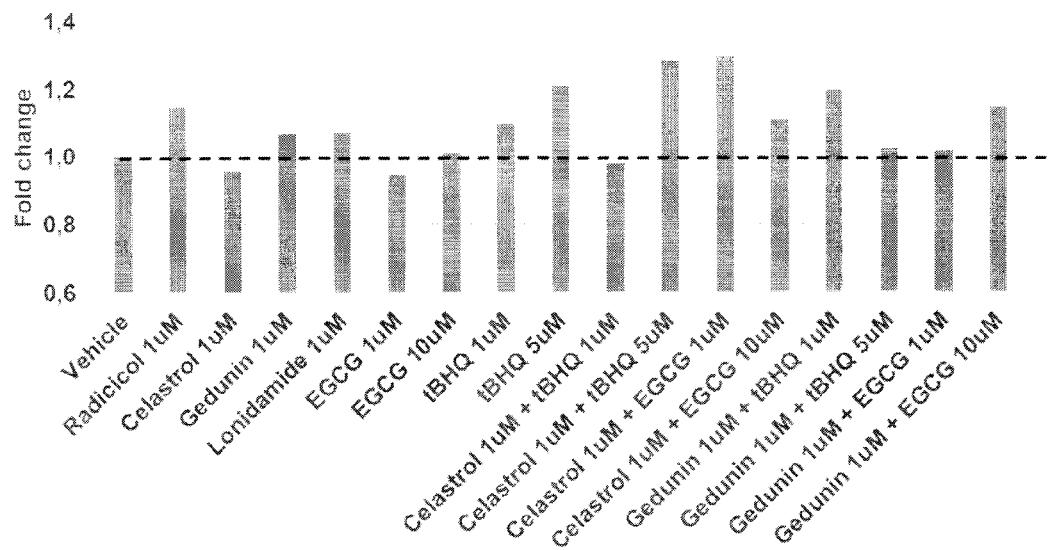
FIG. 17 shows Glutathione peroxidase (GPx) mRNA expression in rMSC following 1-hour treatment and 3-hour washout. EGCG and tBHQ produce synergistic increase of Celastrol-induced GPx expression.
Figure 18:
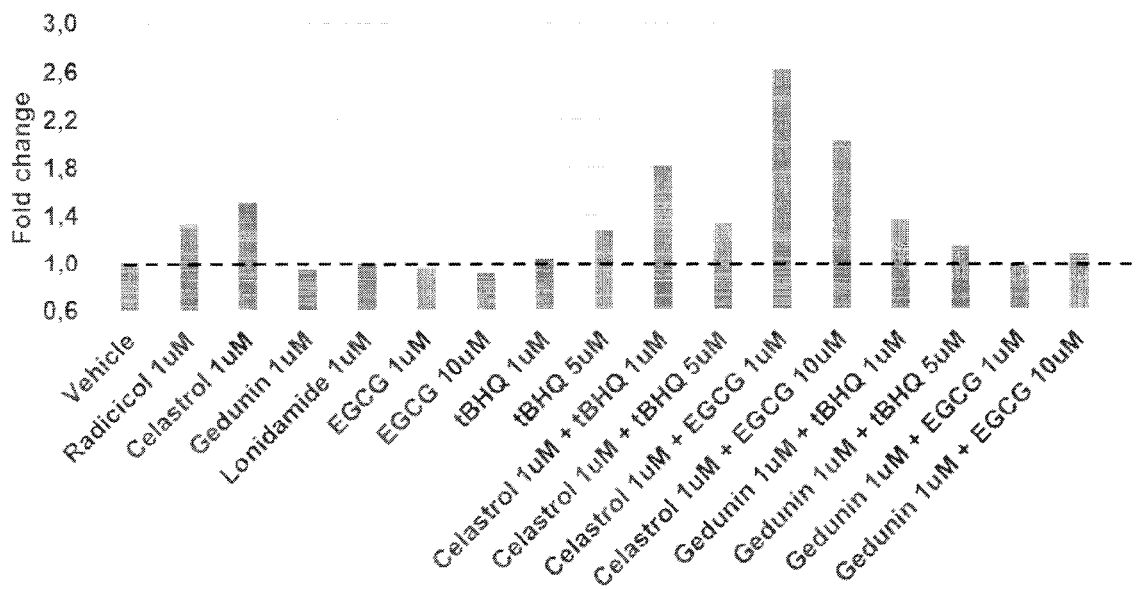
FIG. 18 shows Glutathione reductase (GR) mRNA expression in rMSC following 1-hour treatment and 3-hour washout. EGCG produces synergistic increase of Celastrol-induced GR expression. tBHQ displays synergistic effect only at low dose.
Figure 19:
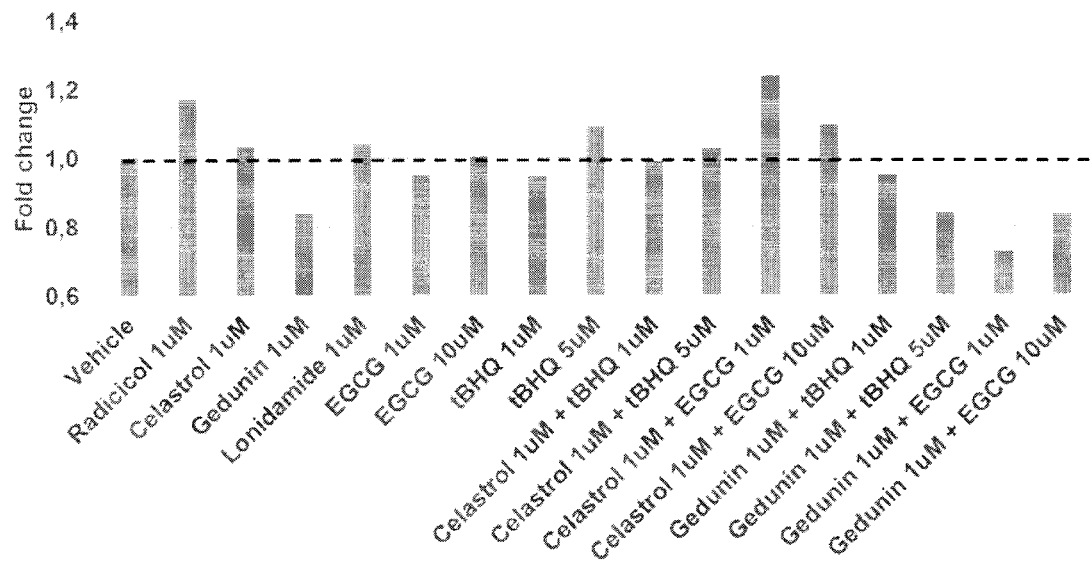
FIG. 19 shows Superoxide dismutase 1 (SOD1) mRNA expression in rMSC following 1-hour treatment and 3-hour washout. EGCG produces synergistic increase of Celastrol-induced SOD1 expression.
Figure 20:
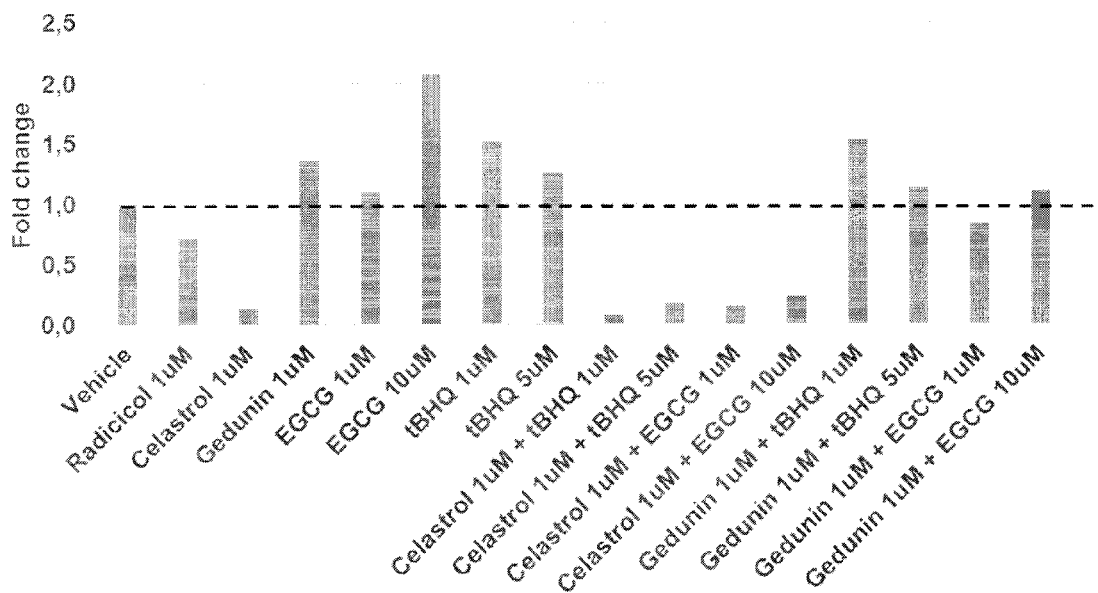
FIG. 20 shows IL-1p mRNA expression in rMSC following 1-hour treatment and 3-hour washout. Celastrol and Gedunin downregulate IL-1β expression induced by EGCG and tBHQ.

The results of these experiments, which are reported in FIGS. 10 to 21, may be summarized as follows:
Expression of HSPs
  EGCG and tBHQ produce synergistic increase of Celastrol-induced HSP70 and HSP32 expression (FIG. 10, 11). In two other rMSC cell lines, EGCG also produced synergistic increase of Celastrol-induced HSP70 expression, whereas tBHQ had no effect on Celastrol-induced changes
  EGCG produce synergistic dose-dependent increase of Celastrol-induced HSP70 and HSP32 expression in human MSC (FIG. 12, 13);
Expression of Growth Factors (GFs)
  EGCG synergistically enhances Celastrol stimulated expression of FGF2 and VEGF, whereas TBHQ increases and decreases both Celastrol and Gedunin expressions of FGF2 and VEGF respectively (FIG. 14, 15).
Expression of Antioxidant Factors
  EGCG synergistically enhances Celastrol stimulated expression of CAT, GPx, GR and SOD1 (FIG. 16, 17, 18, 19).
  tBHQ synergistically enhances Celastrol stimulated expression of CAT, GPx, GR (at low dose tBHQ), and has no effect on SOD1 expressions.
Expression of Inflammatory Cytokines.
  Celastrol and Gedunin downregulate IL1β induced expression by EGCG and tBHQ (FIG. 20);
  EGCG and tBHQ potentiates Celastrol- and Gedunin-induced downregulation of TNFα (FIG. 21).

Together, these results show that EGCG synergistically potentiates Celastrol-stimulated expressions of favourable factors for stem cell function. Without wishing to be bound by theory, this may be due to the inhibition by EGCG of an unknown Celastrol functionality repressor or stabilization of HSP90 conformation for enhanced Celastrol effect. It cannot be excluded that the synergistic effect may also be secondary at least in part to activation of an NRF2 mediator and/or normalisation of the cell redox balance. Indeed, tBHQ, which has no HSP90 inhibiting activity, shows certain synergistic or additive effects on Celastrol stimulated expression in at least one rat line of MSCs. Finally. EGCG and tBHQ co-treatments with Celastrol or Gedunin further downregulate inflammatory cytokines.

Figures 21, 22A:
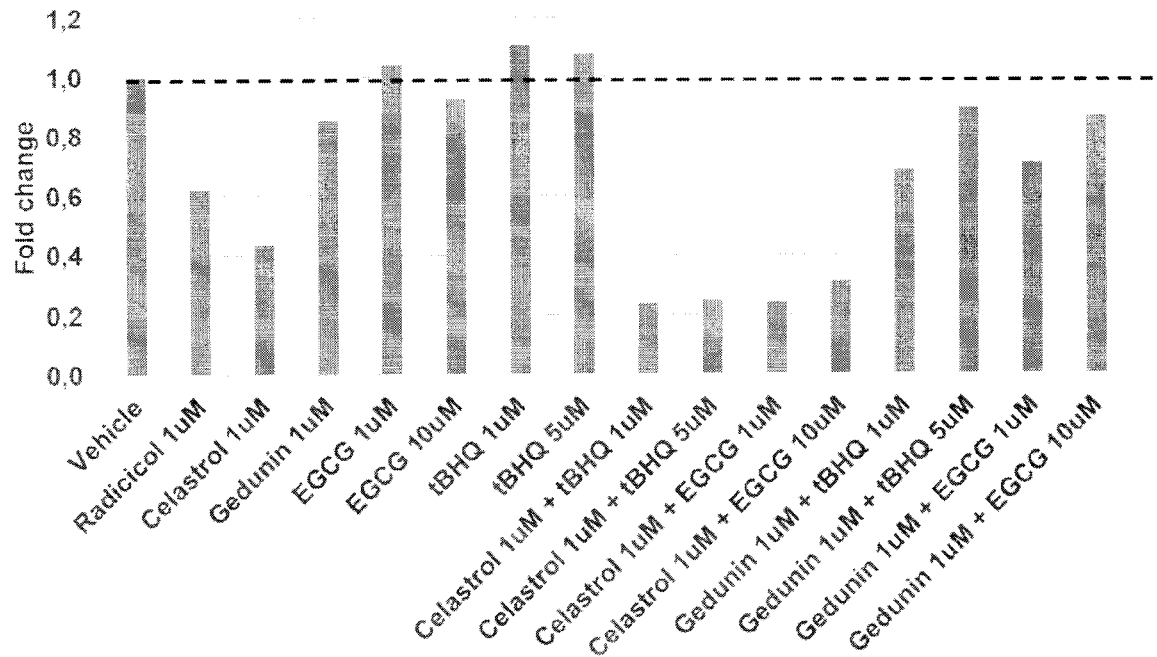
FIG. 21 shows TNFα mRNA expression in rMSC following 1-hour treatment and 3-hour washout. EGCG and tBHQ synergistically accentuate Celastrol- and Gedunin-induced downregulation of TNFα.
FIG. 22A shows a compilation map of rMSC viability and expression results (check marks indicate level of activation; x indicate level of inhibitory effect; ≠ indicates lack of effect; empty cells indicate that the experiment was not performed).

A compilation of the viability and expression results is presented in FIGS. 22A and 22B. These results provide evidence that an optimal pharmaco-conditioning treatment providing a suitable transplant micro-environment combines:

1. HSP90 inhibitor effect (HSP90 co-factor inhibition capable of HSF1 Induction), which was shown to enhance cellular viability to hypoxia-induced death and promote increased expression of various beneficial paracrine factors (HSPs, GF, antioxidant molecules) and reduced expression of inflammatory mediators; and
2. NRF2 activity (with potential HSP90 CT inhibition), which was shown to enhance resistance to oxidative stress-induced death, and to enhance (either additively or synergistically) the expression of certain beneficial paracrine factors and/or to further down-regulate inflammatory cytokine mediators.

Figure 8B:
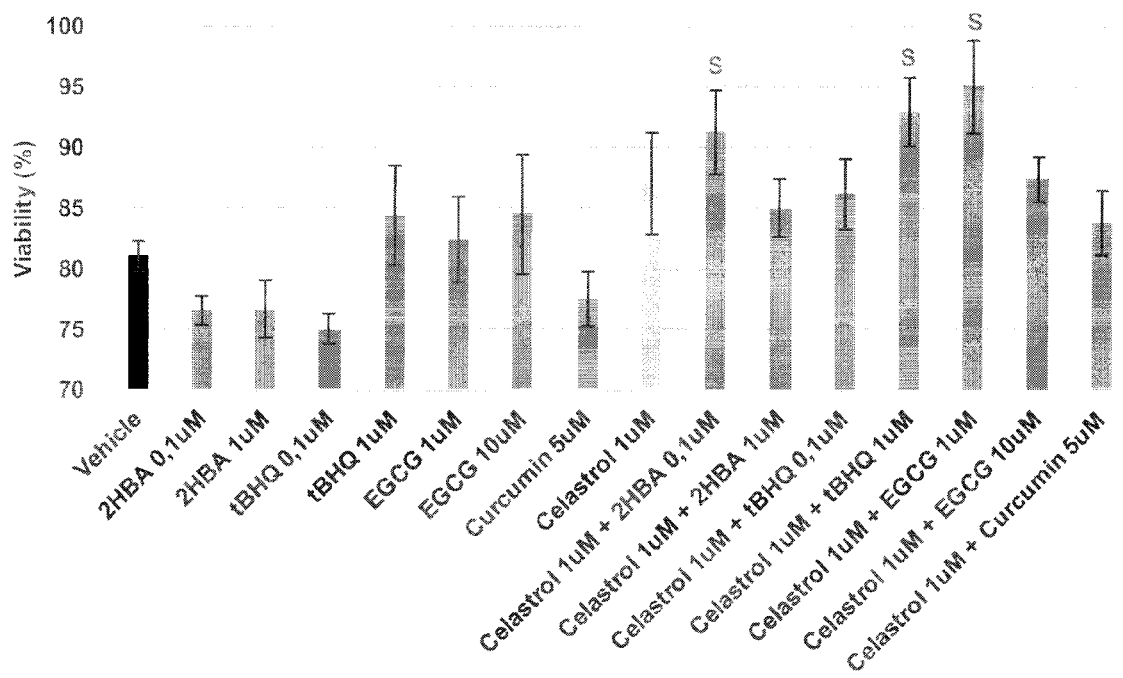
FIG. 8B shows that a 1-hour treatment of H9c2 cardiomyoblasts with Celastrol combined with either 2HBA, tBHQ or EGCG produces a synergistic increase in viability of cells following oxidative challenge (incubation in 1 mM $H_2O_2$ for 1 hour).
Figure 9:
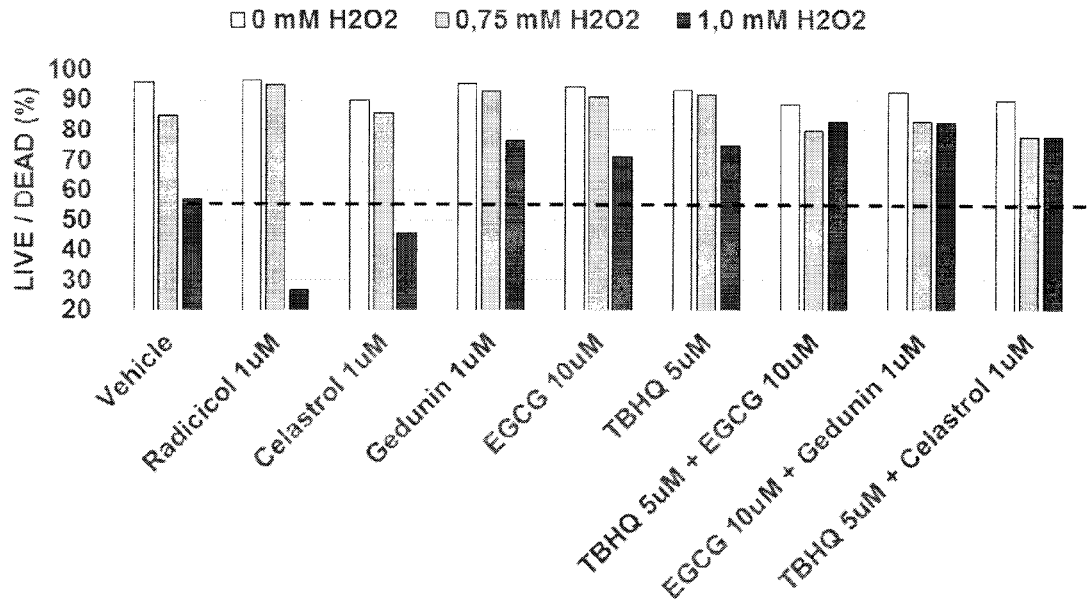
FIG. 9 shows that a 24-hour preconditioning with media from rMSC treated with NRF2 activator (Gedunin. EGCG, tBHQ) protects H9c2 cells from oxidative stress induced death. Potent HSF1 activators alone (Radicicol, Celastrol) show no protection.

Interestingly, the Applicant found that, 2HBA, tBHQ and EGCG also produce synergistic increase when combined with Celastrol in increasing the viability of H9c2 cardiomyoblasts challenged by an oxidative stress (incubation in 1 mM $H_2O_2$ for 1 hour) (FIG. 8B).

Example 4: Identification of Celastrol Analogs as Stem Cell Pharmaco-Optimizers

Using a similar approach to that described in Example 3, the Applicant tested several Celastrol analogs including those exemplified in FIG. 23 and Identified several that have the ability to act as stem cell pharmaco-optimizers (FIG. 24, 25A, 25B, 26A-26D).

The Applicant also tested several combination treatment of Celastrol or Celastrol analogs with potential adjunct agents (e.g., NRF-2 activators and/or antioxidants, FIG. 24) and identified several combinations having synergistic effect (S) or additive (A) on the expression of HSPs, growth factors (GF), antioxidant proteins/enzymes, cytokines, matrix remodeling proteins (FIGS. 25A, 25B and FIGS. 26A to 26D). As may be seen from these data, Analog 3, Analog 1, Dihydrocelastrol and Celastrol are the best HSP90 inhibitors and 2HBA, EGCG, curcumin, tBHQ and Camosol are among top adjunct agents identified.

Figure 26E:
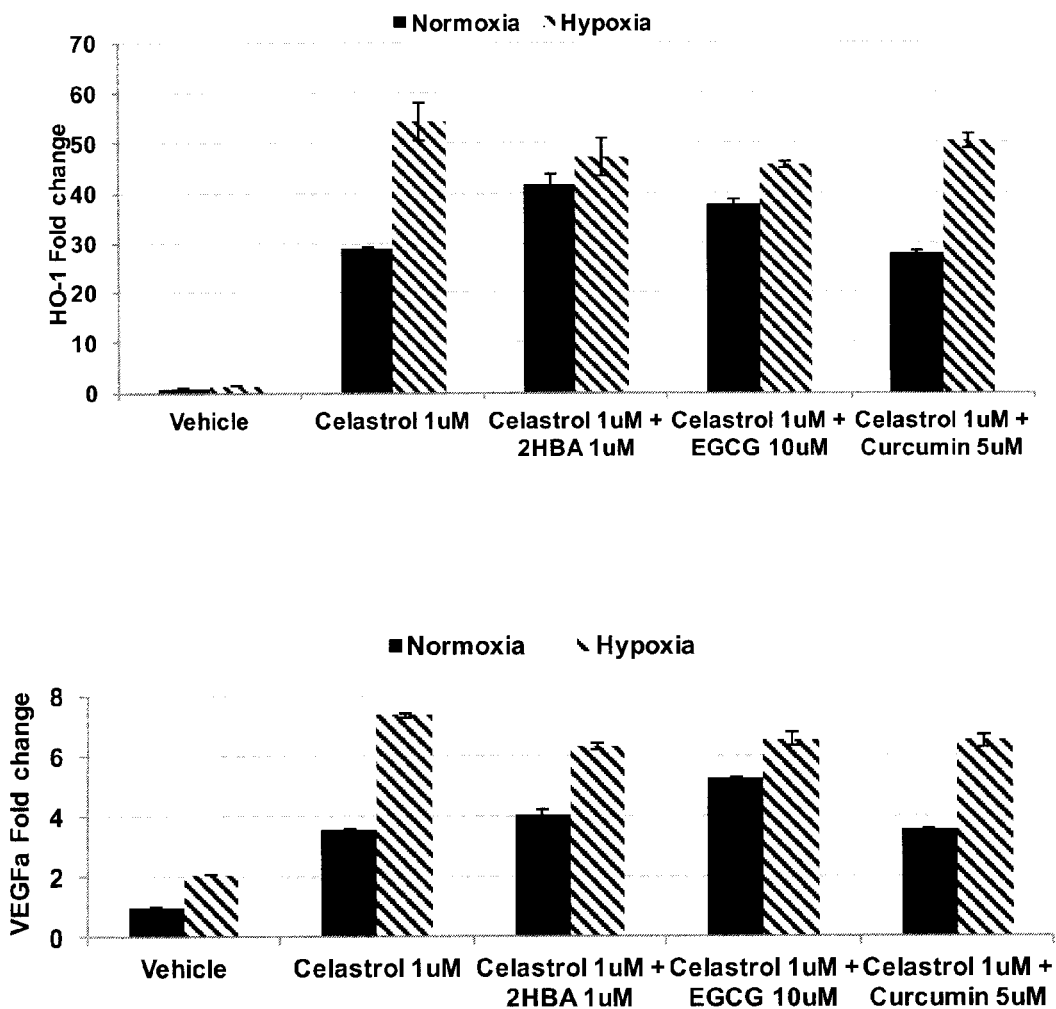
FIG. 26E shows the real-time PCR expression of HO-1 (top panel) and VEGFa (bottom panel) gene mRNA following treatment of H9c2 cardiomyoblasts with Celastrol (1 uM) either alone or combined with adjunct treatments (2HBA 1 uM; EGCG 10 uM or Curcumin 5 uM) for one hour followed by 3 hour incubation in either normoxic or hypoxic (<1% $O_2$) low serum (0.2% FBS) and low glucose condition as may be observed in an infarct microenvironment. Results are expressed as fold change versus Vehicle-treated h9c2.
Figure 26F:
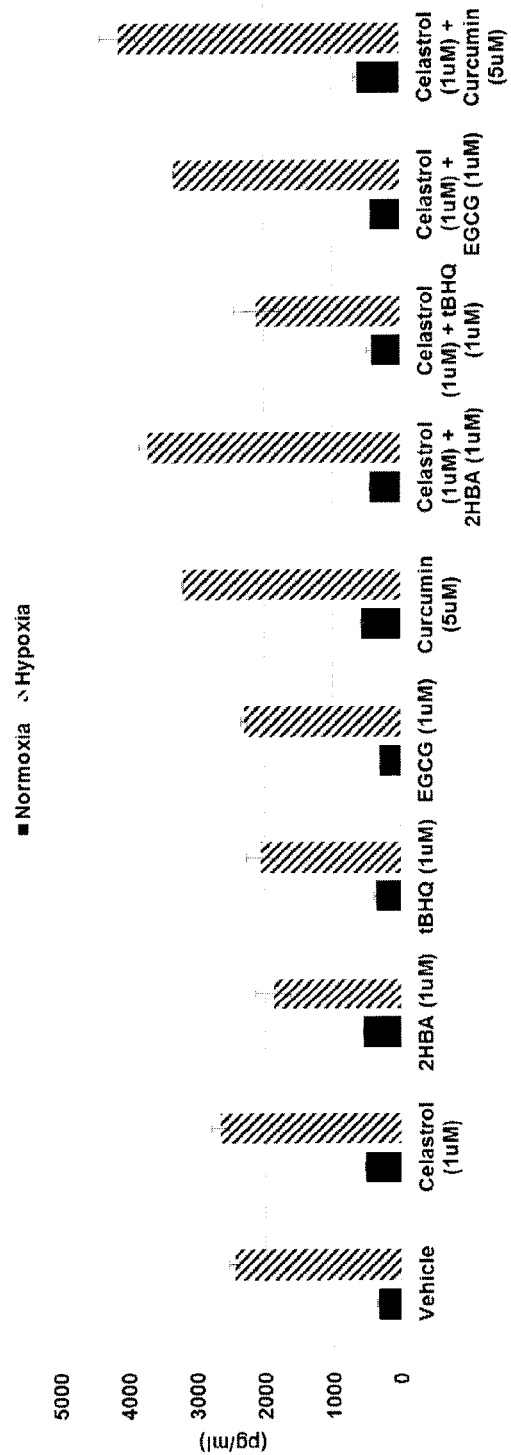
FIG. 26F shows the result VEGFa protein content measured (Thermo Fisher; Bio Plex 200, Bio Rad) secreted by human mesenchymal stem cells (hMSCs) in the culture medium following one hour co-treatment of Celastrol (1 uM) and selected adjunct compounds (1 uM) followed by 48 hour incubation in either normoxic or hypoxic (<1% $O_2$) and low serum (1% FBS) conditions as may be observed in an infarct microenvironment.

In addition, 1-hour treatment of human mesenchymal stem cells (hMSC) with Celastrol combined with 2HBA, EGCG, tBHQ or Curcumin produce additive to synergistic increase in VEGF protein after 48 hours in normal culture whereas culturing the same cells for 48 hours in hypoxic condition as encountered in an infarct microenvironment produces even greater expression of VEGF protein (FIG. 26F). The same observation is essentially viewed, that is, increased mRNA expression of HO-1 antioxidant and VEGFa angiogenic factor in H9c2 cardiomyoblasts treated for 1-hour with Celastrol combined with 2HBA and EGCG adjuncts followed by 3 hour washout period in normoxic or hypoxic condition (FIG. 26E).

Example 5: Celastrol Increases rMSC Viability Following Cryopreservation

Figure 27A:
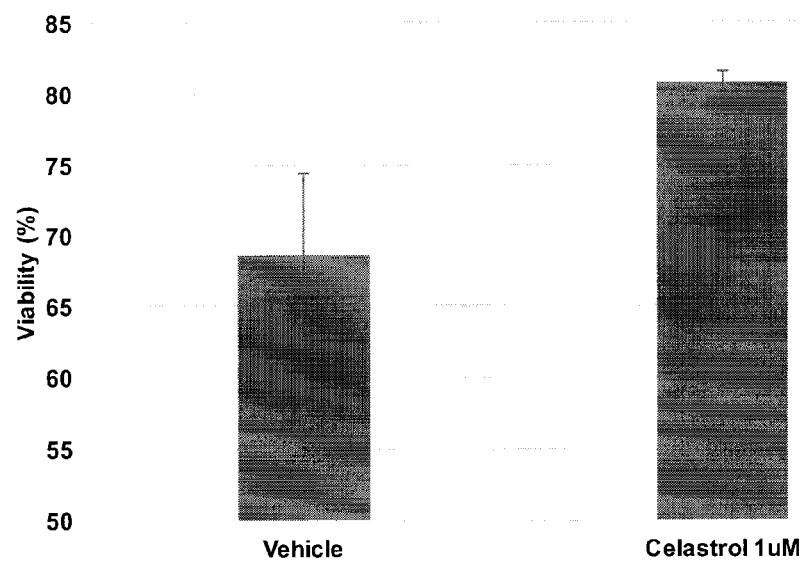
FIG. 27A shows that 1-hour preconditioning with Celastrol before cryopreservation increases rMSC viability following cell thaw.

Proper cryopreservation is an important aspect for cell processing labs which are required to demonstrate that their cryopreservation protocol results in acceptable post-thaw viability (≥70%) before transplant. For example, studies have demonstrated that cryopreservation induces significant alterations of thawed hepatocytes and impairs their viability, attachment and function. The results presented in FIG. 27A show that a one hour preconditioning of rMSC with Celastrol prior to cryopreservation increases rMSC viability post-thawing.

Mesenchymal stem cells (MSC) are Isolated from male rats (175-200 g) hindlimb bone marrow, and expanded as described. Briefly, bone marrow mononuclear cells (BMNCs) are isolated by Ficoll-Paque (Amersham) gradient centrifugation and cultured in Minimum Essential Medium alpha 1X (αMEM 1X: Gibco 12571) with 10% FBS (Gibco) and 1% penicillin-streptomycin (P-S: Invitrogen 15140). After 48 h, nonadherent cells are discarded, and cells are washed with new medium. MSC are separated from hematopoletic cells based on preferential attachment to polystyrene surface. Multilineage potential of MSC is confirmed by in vitro adipogenic and osteogenic/chondrogenic differentiation assays with specific culture conditions and staining. Immunophenotyping is performed by multiparameter flow cytometry (FACScan®; Becton Dickinson; Mountain View, CA, USA) with monoclonal antibodies directed against surface antigens such as CD29, CD34, CD45, CD90, CD105 (Coulter Immunology, Hialeah, FL, USA). For in vitro experiments, MSC will be used between $4^{th}$ and $10^{th}$ passage.

Cell Viability Protocol (Freeze/Thaw Cycle)

MSC are resuspended in 10% serum media (αMEM 1X, 10% FBS, 1% P-S) and plated using a multichannel pipette in 96 well plates at a density of 4000 cells per well and incubated at 37 C. Each experimental and control conditions are plated in triplicate. The next day, the media is gently aspirated and replaced with low serum media (αMEM 1X, 1% FBS, 1% P-S) containing either Celastrol (10E-6M) or Vehicle (DMSO) for one hour. The media is then aspirated, cells are washed with 3 changes of media (αMEM 1X, 1% FBS, 1% P-S). Cells are trypsinated and counted using the Countess II FL automated cell counter (Thermo Fisher Scientific).

Freezing cells: Following trypsination and counting steps as described above, cells are aliquoted at the desired density, DMSO is added (1:10 final dilution) to the cellular concentrate and transferred to pre-labelled cryovials. Cryovials are placed in freezing container and transfer to −80° C. overnight, and later transferred to −150° C.

Thawing cells: Frozen cells are rewarmed by pouring pre-warmed culture medium on top of the frozen aliquot. Vials are centrifuged (200×g; 3 min), supernatant is aspirated and cells are re-suspend in pre-warmed 10% serum media (αMEM 1X, 10% FBS, 1% P-S). Trypan blue dilution is added to a cell aliquot and viability is measured using the Countess II FL automated cell counter (Thermo Fisher Scientific).

Figure 27B:
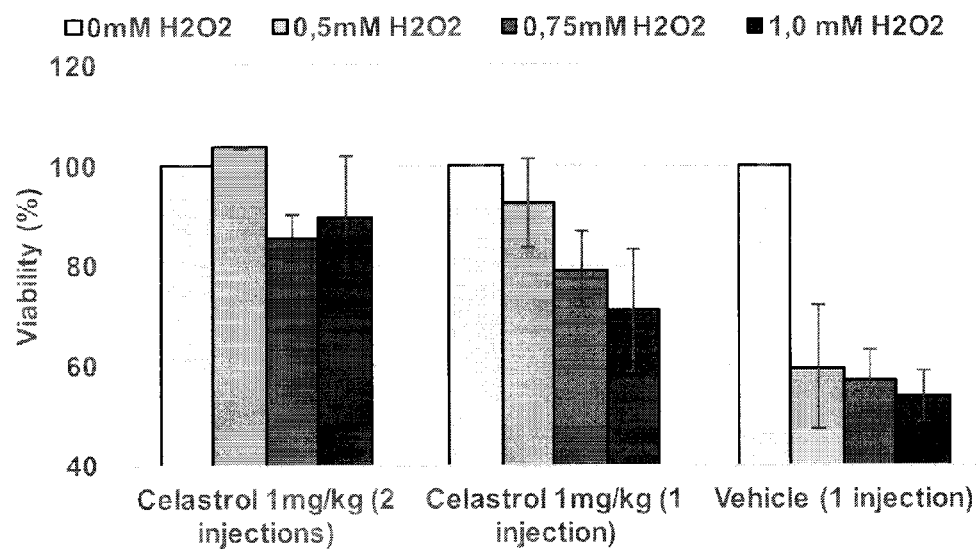
FIG. 27B shows that in vivo Celastrol treatment dose-dependently conditions rMSC to withstand oxidative stress induced death.

Example 6: Celastrol Increases Resistance to Oxidative Stress Induced Death In Vivo The results presented in FIG. 27B show that in vivo conditioning of Sprague-Dawley rats with either one or two intraperitoneal injections of Celastrol (1 mg/kg; 12 hours interval), dose dependently conditions bone marrow cells to withstand oxidative stress induced death (see details below).

Mesenchymal stem cells (MSC) are isolated as described in Example 5.

In Vivo Conditioning

Sprague-Dawley rats (CD CRL; Charles-River) receives 1 or 2 intraperitoneal injections of Celastrol (1 mg/kg) or Vehicle at 12 hours interval. Rats were then sacrificed and MSC were isolated as described above. MSC were placed in culture by resuspending in 10% serum media (αMEM 1X, 10% FBS, 1% P-S) and plated using a multichannel pipette in 96 well plates at a density of 4000 cells per well and incubated at 37 C. Each experimental and control conditions are plated in triplicate.

Cells are then challenged by incubation with 1% serum media containing 0 mM, 0.5 mM, 0.75 mM, or 1 mM hydrogen peroxide (ACP Chemicals, H7000) for 60 minutes. Cells are then gently washed twice with warm αMEM 1X media stained with the LIVE/DEAD kit (Thermo Fischer Scientific) according to the manufacturer's protocol. Images are captured and analysed using a High content screening (HCS) system Operetta, running Harmony High-Content Imaging and Analysis software ver. 4.1 (Perkin Elmer, Waltham, MA). The results presented herein show that in vivo treatment of Sprague-Dawley rats with either one or two Injections of Celastrol, dose-dependently conditions bone marrow cells to withstand oxidative stress induced death.

Example 7: Celastrol Preserves Endothelial Layer Viability

Figure 28:
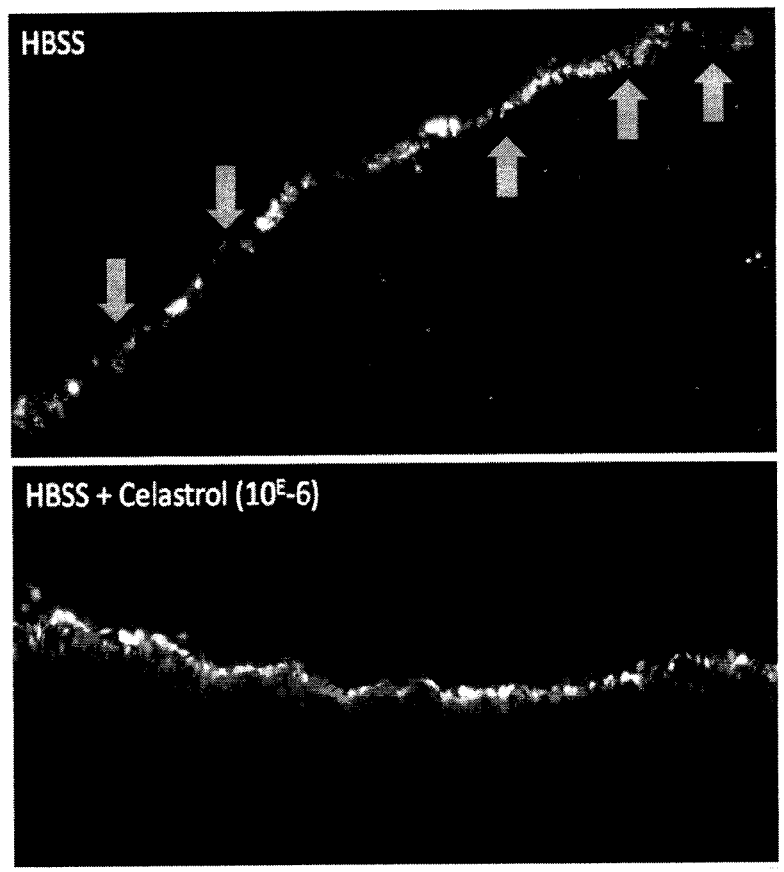

Pig carotid artery was harvested, dissected into closed rings and semi-circles open rings structures and placed overnight in Hank's Balanced Salt Solution (HBSS) or HBSS containing Celastrol at 10E-6M final concentration. Carotid rings were stained with the LIVE/DEAD kit (Thermo Fischer Scientific) according to the manufacturer's protocol. Tissues were imaged by confocal microscopy (Olympus, FV1000MPE/BK61WF) with 20X dipping objective. Z-stacks of carotid endothelial surface were also obtained. FIG. 28 show preservation of endothelial layer viability and integrity with Celastrol compared to the negative control without Celastrol where arrows point to dead cells and loss of endothelial layer Integrity (FIG. 28).

Example 8: Celastrol Induces Cytoprotective Mediators

Figure 29A:
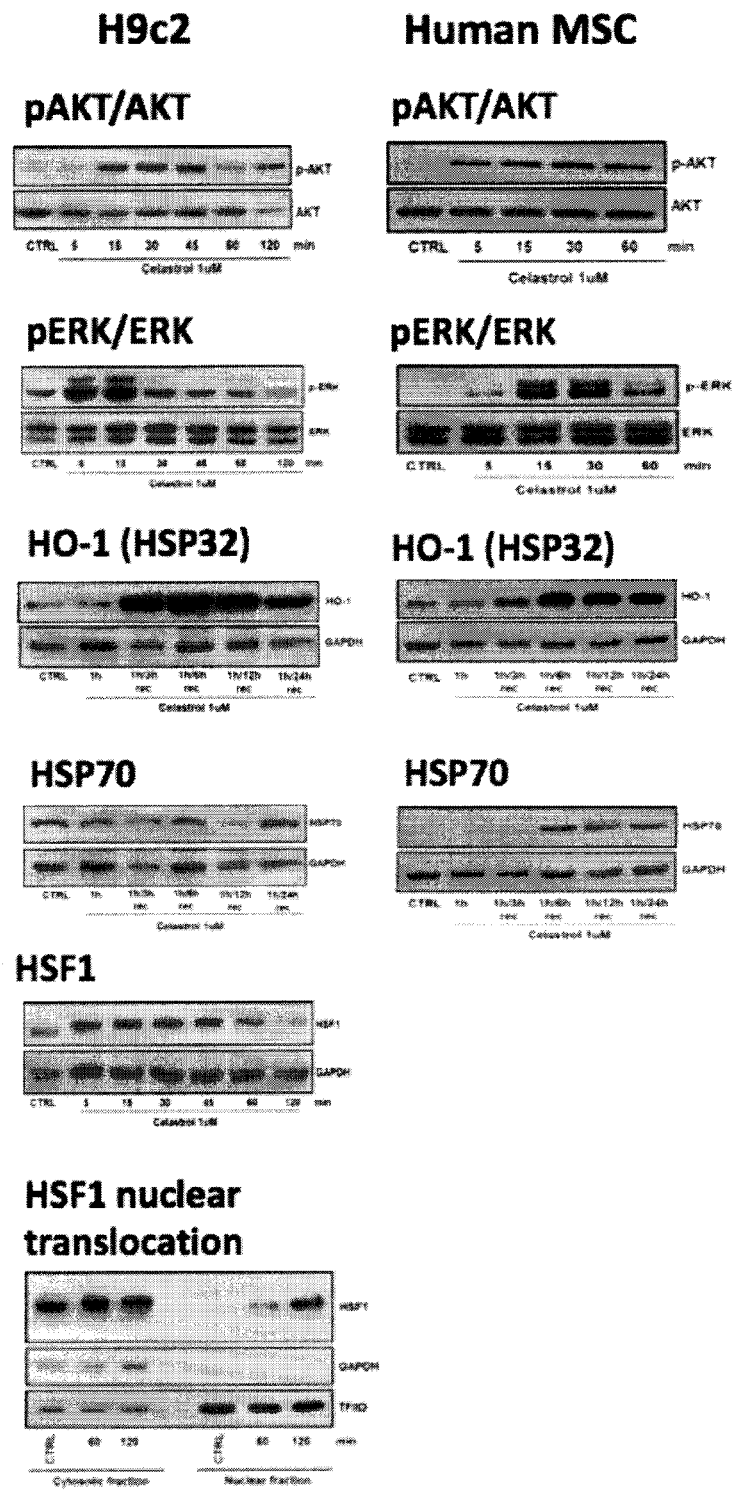
FIGS. 29A and 29B are Western blots showing the protein expression in either total cell extracts or nuclear and cytoplasmic fractions in different cell types stimulated by Celastrol (1 uM) for 5 to 120 minutes followed by 0 to 24 hours recuperation).
Figure 29B:
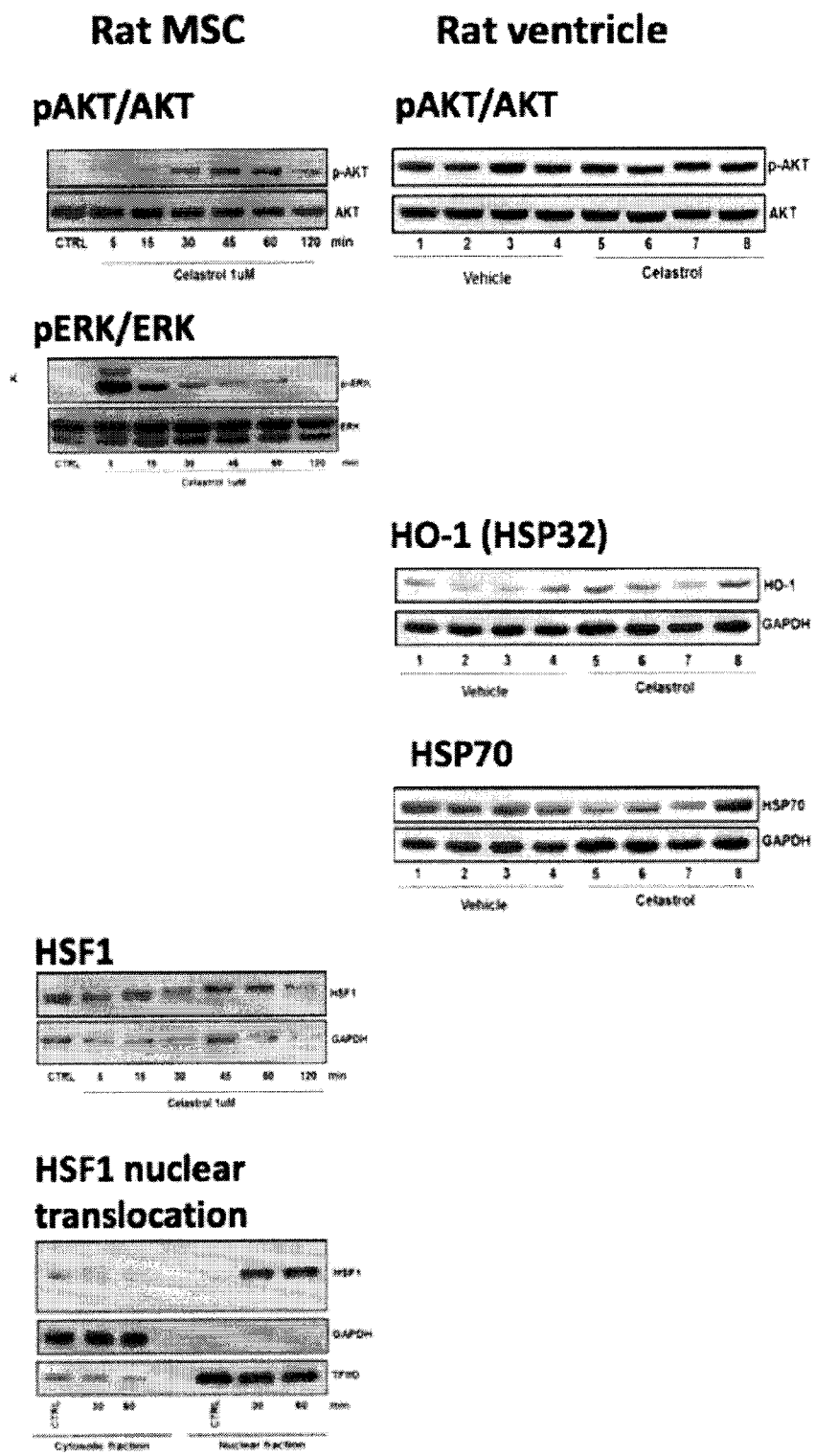

Celastrol Induces cytoprotective mediators (survival kinases: pAkt/Akt, pERK/ERK; antioxidant HO1; Heat shock response proteins: HSF1, HSP70) and protein expression kinetics similarly in various cell types (times tested 5 to 120 min treatments for $10^4$M dose and either 0 to 24 hour recuperation following 1 hour treatment with $10^4$M Celastrol). FIGS. 29A and 29B represent Western Blot and viability assays performed in various rat and human cell lines (H9c2 rat cardiomyoblast; human and rat MSC; rat neonatal cardiomyocytes; INS-1 insulin producing rat beta cell line).

More particularly INS-1 cells were cultured. In complete media (RPMI supplemented with filtered solutions: 1 mM Na pyruvate+50 µM b mercaptoethanol, 10 mM Hepes Ultra pure, 2 mM L-Glutamine) containing 10% FBS. Cells are trypsinated (0.25% Trypsin-EDTA), centrifuged at 1500 RPM for 5 minutes and resuspended in complete INS media supplemented with 1% FBS. Cells are counted using a hemacytometer and 1-2 million cells are resuspended in Sarstedt tubes containing 9 mls of 1% FBS complete INS media and 2.5 ul or 5.0 ul of 1 mM Hsp90 inhibitor (Celastrol: Cayman Chemical 70950, Geldanamycin: Cayman Chemical 13355, or Radicicol: Cayman Chemical 13089) resuspended. In DMSO. Control samples are prepared similarly but by replacing Hsp90 inhibitor with either 2.5 ul or 5.0 ul of DMSO vehicle. The volume of cell suspensions are completed to a final volume of 10 ml with 1% FBS complete INS media. Suspensions are gently mixed by a few inversions and tubes are placed at 37 C for 30 minutes. Inversions are repeated after 15 minutes. Tubes are then centrifuged at 1500 RPM for 5 minutes, the media is gently aspirated, and the cells are washed with 12 mls of warm RPMI solution. The spin and wash cycle Is repeated twice more before resuspending cells with 2.5 ml or 5.0 ml of complete INS media containing 1% FBS, for the pellets containing 1 or 2 million cells respectively. Next, using a multichannel pipette, 100 ul aliquots of cell suspension containing 40,000 cells each are plated in 96 well plates. Each experimental and control conditions are plated. In quadruple and Incubated. In normoxic or hypoxic condition for 6 hours. Hypoxia (<1% oxygen) Is achieved by placing culture plates in an air tight hypoxia chamber (Billups-Rothenberg) and flushed for 10 minutes at a flow rate of 15-20 liters per min with a gas mixture of 5% $CO_2$ balanced with 95% $N_2$. After 6 hours of incubation, media from hypoxia-challenged and normoxic control cultures is replaced with 90 ul of 10% FBS complete INS media, and 10 ul of PrestoBlue reagent is added to each well. After 60 minutes of incubation, viability is quantified by fluorescence acquisition using a plate reader.

Figure 29C:
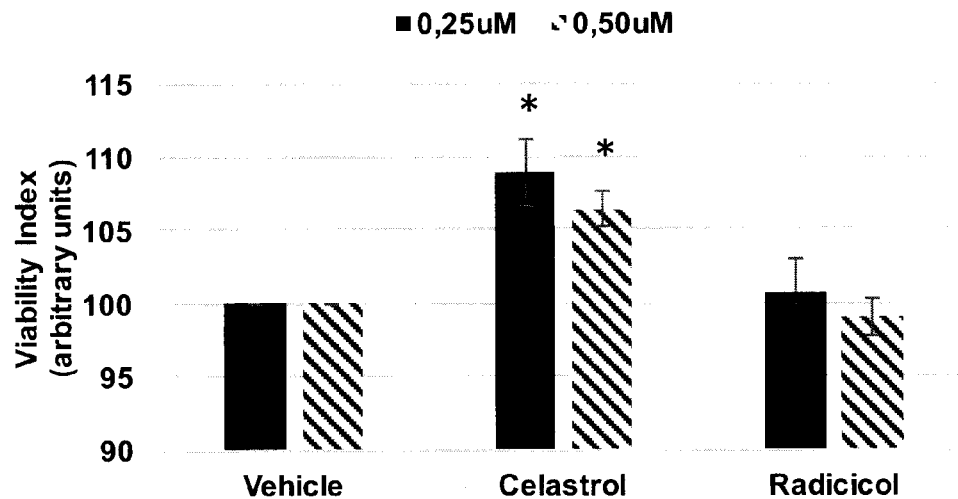
FIG. 29C is a histogram representing the viability index of insulin-secreting INS-1 cells pre-conditioned for 30 minutes with Celastrol or Radiciol at concentrations of 0.25 uM or 0.50 uM after a 6 hour hypoxic challenge. Results are compared to Vehicle-treated cells.

These data show that short preconditioning of INS-1 cells with Celastrol protects cell viability when challenged by lethal hypoxic stress (FIG. 29C).

Example 9: Celastrol Rescue Rats from Lethal Drop in Blood Pressure Induced by LPS In addition to the effect of Celastrol in decreasing infarct size and the preservation of cardiac function in rats, the Applicant observed a modulation of blood pressure. In treated rats. Considering the potential of the compounds and combinations described herein in the preservation of organs and tissues to damage (i.e., ischemic, oxidative, inflammatory, necrotic) and in the preservation of systemic pressure/ perfusion, their use in shock models (i.e. septic, cardiogenic) would be desirable in view of the high rates of organ failure and mortality associated with these conditions. Indeed, in the United States, more than 750,000 annual cases of severe septicemia are diagnosed with a mortality rate of 25-30% (Crit Care Med 29 (7): 1303Y1310, 2001). caused by failure of multiple organs including cardiac dysfunction as a critical manifestation (Circulation 116 (7): 793Y802, 2007). We propose the addition of a septic shock model either the endotoxic model induced by the bacterial lipopolysaccharide (LPS) in the rat (Life Sci., 1997; 60 (15): 1223-30).

Figure 30:
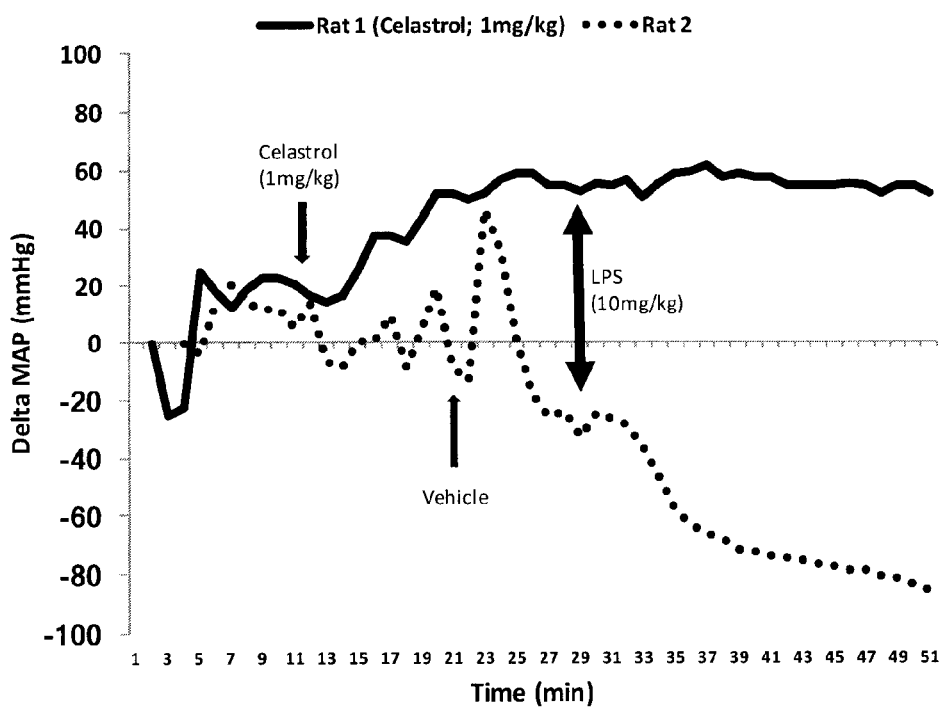
FIG. 30 is a graph showing that Celastrol 1 mg/kg prevents lethal drop of blood pressure in rat receiving 10 mg/kg dose of LPS.

Briefly SD rats are anesthetized with isoflurane 2.5-3.0% (Abbott Laboratories, Abbott Park, IL), 1 L/min oxygen and placed on a heated blanket to prevent hypothermia. The left external carotid artery is cannulated with gelco #20 and relayed to a pressure sensor. Alternatively, depending on the size, the left femoral artery is cannulated. The rats are kept at 2% isoflurane, 1 L/min oxygen, and basal pressure measurements are collected. The pressure kinetics in response to i.v. injection via the jugular vein of LPS (20 to 50 mg/Kg) and injection I.p. of Celastrol (1 mg/Kg) is determined. It is noteworthy to mention that the dose of LPS in animals may be variable and also depend on the age of the animals (Infection and immunity, March 1996, Vol. 64, no. 3, p769). In our experiment, both rats received a first bolus of LPS at 10 mg/kg. Following transient drop in blood pressure (BP) for both rats, BP stabilized and regained baseline value. Then either an injection of a bolus of 300 ul i.p. of Celastrol (1 mg/Kg) or vehicle (10% DMSO, 70% Cremophor EL/ethanol (3:1). 20% PBS) was performed in distinct rats (see arrow; FIG. 30 before re-injection of 10 mg/kg bolus LPS in both rats resulting. In a lethal drop. In blood pressure in Vehicle treated rats whereas blood pressure is preserved in rats having received a single injection of Celastrol (FIG. 30).

Example 10: Celastrol Induces the Expression of Hsp32 (HO-1) in the Kidney of Rats The Applicant previously showed that Celastrol promoted cardiomyocyte survival, reduction of injury and adverse remodelling with preservation of cardiac function in the rat ischemic myocardium. The Applicant tested whether this protective effect could be observed in other types of Ischemic diseases.

Rats are anaesthetized with 2.0%-3.0% isoflurane (Abbott Laboratories) in 1 L/min of oxygen, and placed in supine position on a heating pad. Rats receive a single bolus injection of Vehicle solution or Celastrol ((Cayman Chemical 70950) 50 mM stock solution resuspended in 0.2 uM filter sterilized vehicle: DMSO (Sigma 154938) (4% total volume), PBS 1X (96% total volume)) via the external jugular vein at a dose of 1 mg/kg. Rats are shaved, ophthalmic ointment is applied to corneas, and bupivacaine (2 mg/kg s.c.) Is injected at the site of the 3-4 cm incision starting at the base of the sternum to the ombilic. The incision is maintained open with retractors, and the intestines are wrapped in sterile saline damped gauze. The left kidney (K) is isolated and the renal artery is occluded with a vascular clip. The intestines are replaced in the abdominal cavity and the skin is closed with temporary 3-0 sutures (Ethicon). Rats receive buprenorphine hydrochloride (0.05 mg/kg s.c.) and are maintained with 1.0%-2.0% isoflurane (Abbott Laboratories) in 1 L/min of oxygen for 30 minutes of ischemia and an additional 45 minutes of reperfusion following removal of the clip. Rats are exsanguinated by perfusion with 40 mM KCl supplemented saline and organs are harvested, rinsed in cold phosphate buffered saline (PBS1X), preserved in 10% formalin buffered with PBS overnight for paraffin embedded for histological/immunohistological sections or snap frozen in liquid nitrogen for western blot expression analysis.

Figure 31:
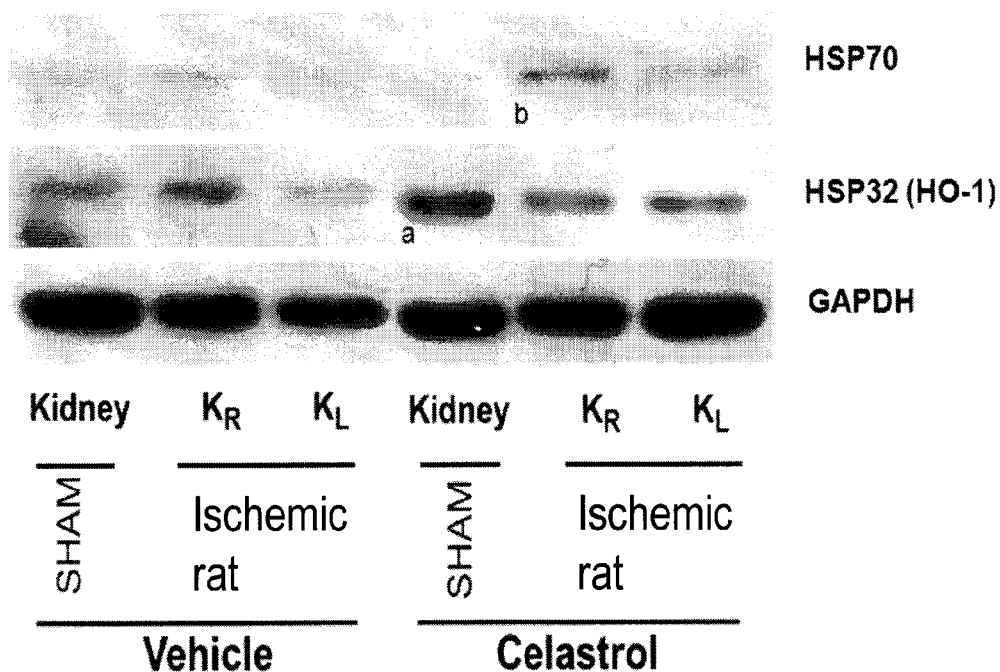
FIG. 31 is a picture of a Western blot showing that a single injection of Celastrol (1 mg/kg) induces the expression of Hsp32 (HO-1) within 60 minutes in the kidneys of rats (see a). Celastrol increases the expression of Hsp70 in the non-ligated control kidney of rats undergoing renal Ischemia, suggesting an increase in systemic sensitivity and a cytoprotective response (see b).

Results of the Western Blot analysis presented herein demonstrate that a single injection of Celastrol (1 mg/kg) induces the expression of Hsp32 (HO-1) within 60 minutes in the kidney of rats (FIG. 31). Moreover, Celastrol increases the expression of Hsp70 in the non-ligated control kidney of rats ($K_R$) undergoing renal ischemia, suggesting an increase in sensitivity and a cytoprotective response. This phenomenon is of particular interest because it suggests the possibility of conferring systemic cytoprotections during clinical interventions akin to remote conditioning with possible generation of systemic neuro-humoral protective mediators, thus reducing potential associated complications (e.g. stroke incidence resulting from surgical procedure).

Example 11: Effect of Celastrol and Celastrol Analogs on Cell Viability and Protection from Stress and Damage The Applicant tested the effect of Celastrol or Celastrol analogs on hypoxic cultures of H9c2 rat cardiomyoblasts and in a rat model of myocardial infarction. The combinations of Celastrol or Celastrol analogs with adjunct agents may tested in a similar fashion.

In Vitro Studies
Cell Culture and Stimulation:

For survival to hypoxic challenge and oxidative challenge, H9c2 cardiomyoblasts are submitted to the hypoxia/serum starvation (<1% $O_2$ in hypoxia chamber in low serum media for 48 hours) or oxidative stress (incubation in media for 1 hour spiked with 0-1 mM $H_2O_2$). Viability status of H9c2 cells was evaluated using the LIVE/DEAD assay.

Next, the hypoxia/reoxygenation challenge is performed. Briefly, viability analysis was performed in rat H9c2 cardiomyoblasts as previously reported. For hypoxia/reoxygenation stress, cells were cultured in DMEM no glucose (Life Technologies), serum starved and placed. In hypoxic conditions (<1% $O_2$) for 18 h. At reoxygenation (normoxic conditions), cells were treated with Celastrol ($10^{-10}$ to $10^{-6}$ mol/L, Cayman Chemical, Ann Arbor, MI), Celastrol analogs or vehicle (Dimethyl sulfoxide (DMSO), Sigma-Aldrich Canada, Oakville, ON; final concentration <1% v/v) in DMEM high glucose 1% FBS for 1 h, then reoxygenation was continued in DMEM high glucose for an additional 5 h.

Figure 32:
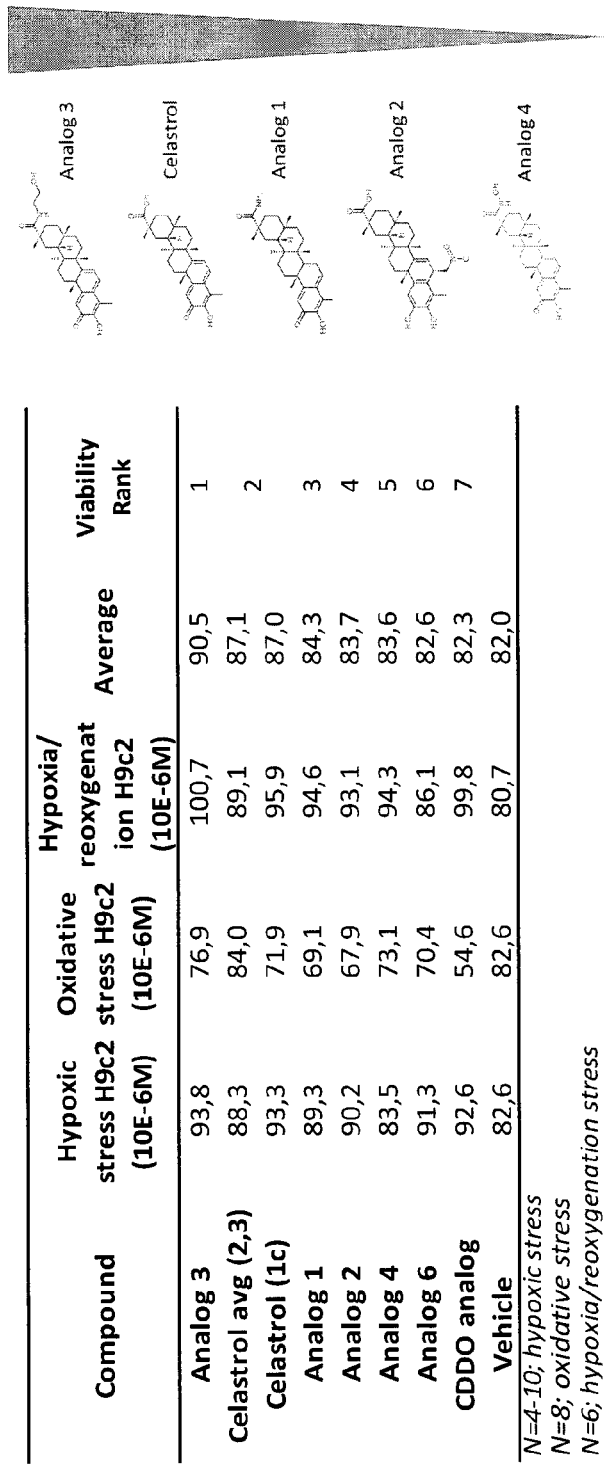
FIG. 32 is a Table summarizing the effect of Celastrol (Celastrol 1c: purchased from commercial source; Celastrol 2 and 3 used to generate synthetic analogs) and Celastrol analogs on the viability of H9c2 cells during hypoxic stress, oxidative stress and hypoxia/reoxygenation stress.
Figure 33:
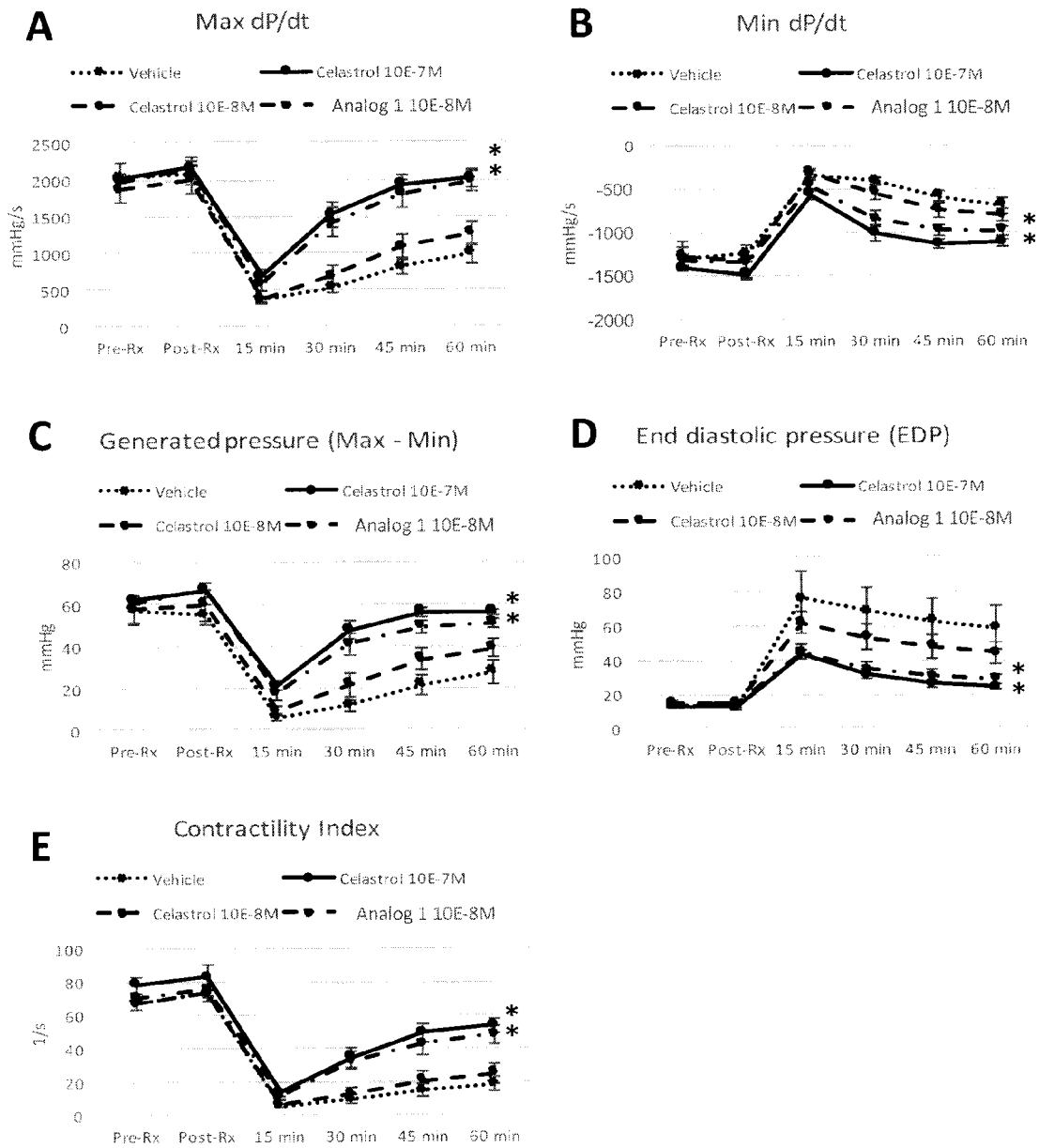
FIG. 33 A to H indicate Celastrol ($10^7$ mol/L, best dose) and Analog 1 ($10^{-8}$ mol/L dose) protected the heart from I/R-Induced systolic dysfunction as shown by changes in A, B) +/−dP/dt, C) generated pressure (maximum−minimum pressure), D) end diastolic pressure (EDP), and E) contractility index compared to Vehicle (DMSO) treatment following warm global cardiac ischemia with reperfusion. F) Coronary reserve flow (CRF) was preserved with treatments, G) high sensitivity troponin T (TNT-hs) release and H) infarct area measured by TTC stain was significantly reduced in Celastrol and analog treatment groups compared to vehicle (DMSO) treated hearts following I/R injury.

The results presented in FIG. 32 show that Celastrol (1 uM) (Celastrol 1c: purchased from commercial source; Celastrol 2 and 3 used to generate synthetic analogs) and Celastrol analogs Analog 3 (1 uM), Analog 1 (1 uM), Analog 2 (1 uM) and Analog 4 (1 uM) are effective at protecting H9c2 cardiomyoblasts from hypoxia and hypoxia/reoxygenation stress.

Example 12: Celastrol and Celastrol Analogs for Use in Treatment of Ischemic Disease Lewis rats (250-300 g, Charles River, St Constant, QC) were used in all ex vivo and in vivo experiments. All animals were handled according to the Guide for the Care and Use of Laboratory Animals.

Ex Vivo Studies
Isolated Perfused Heart Preparation:

Rats were randomly assigned to the following groups: Vehicle (n=6), Celastrol or Celastrol analogs $10^{-8}$, $10^{-7}$ or $10^{-6}$ mol/L (n=5 each). Under isoflurane anesthesia rats were injected with Heparin (I.P, 1000 I.U, Novartis, Dorval, QC) and hearts were harvested and immediately submerged in ice cold Krebs buffer (in mmol/l: NaCl 113, KCl 4.5, $NaH_2PO_4$ 1.6, $CaCl_2$ 1.25, $MgCl_2+6H_2O$ 1, D-Glucose 5.5, $NaHCO_3$ 25). The heart was retrogradely perfused using a Langendorff system (Radnoti, Monrovia, CA) with a constant aortic pressure of 60-70 mmHg, using Krebs buffer at 37° C., bubbled with 5% $CO_2$ balanced $O_2$. A latex balloon connected to a pressure transducer was Inserted in to the left ventricle (LV) and adjusted to 15 mmHg (LV preload). Hearts were paced at 300 bpm and allowed 20 minutes of stabilization.

Intraventricular pressures were continuously measured using a Power lab 8/30 polygraph (ADinstruments, Colorado Springs, CO), recorded and analysed using LabChart pro v.7.3.7 (ADinstruments).

To ensure that Celastrol, Celastrol analogs or vehicle (DMSO) were in contact with the heart at the moment of the initiation of reperfusion, the system was primed at the moment of inducing warm global Ischemia, achieved by stopping cardiac pace and perfusion for 30 minutes. Reperfusion was started using Krebs buffer with Celastrol ($10^{-8}$, $10^{-7}$ or $10^{-6}$ mol/L) or vehicle for 10 minutes, then continued (Krebs buffer) for a total reperfusion time of 120 minutes.

Cardiac effluent was collected for 5 minutes at the end of stabilization, at 5 minutes reperfusion and then every 15 minutes for 60 minutes in total. Volumes were measured and samples kept at –80° C. until analysis.

At the end of reperfuslon, hearts were sliced transversally (1-2 mm), and stained with 5% 2,3,5-Triphenyl-tetrazolium chloride in phosphate buffer saline pH 7.4 (TTC, Sigma-Aldrich Canada) for 20 min at 37° C.[15]. Slices were weighed, then images were taken using a Stemi 508 Stereo microscope coupled to a AxioCam ERc 5s camera and processed with Zen 2.3 imaging software (Carl Zeiss Canada, Toronto, ON). Analyses were performed using ImageJ 1.51 h freeware (NIH, Bethesda, MD). Infarct area was normalised to the weight of the heart tissue slice. One slice per heart was snap frozen for gene and protein expression.

The results presented in FIG. 33A-H indicate Celastrol ($10^{-7}$ mol/L, best dose) and Analog 1 ($10^{-8}$ mol/L dose) protected the heart from I/R-induced systolic dysfunction as shown by changes. In A, B)+/−dP/dt, C) generated pressure (maximum−minimum pressure), D) end diastolic pressure (EDP), and E) contractility index compared to Vehicle (DMSO) treatment following warm global cardiac ischemia with reperfusion. F) Coronary reserve flow (CRF) was preserved with treatments, G) high sensitivity troponin T (TNT-hs) release and H) infarct area measured by TTC stain was significantly reduced in Celastrol and analog treatment groups compared to Vehicle (DMSO) treated hearts following I/R injury.

In Vivo Studies

Rats were randomly assigned to the following groups: Sham (n=6), Vehicle (n=8), Celastrol 1 mg/Kg (n=6) or Celastrol analogs. Under 2% isoflurane anesthesia, baseline echocardiography using a Sonos 5500 Imaging System (Philips, Philips Healthcare, Andover, MA, USA) with a 12 MHz transducer was performed as described[12]. All measures were acquired by the same experienced observer, blinded to the treatment. For each measurement, three to five cardiac cycles were analysed and averaged.

After echocardiography, the animal was intubated and mechanically ventilated, then bupivacaine 2 mg/kg was injected, and a left thoracotomy was performed, exposing the heart. Using a 5-0 silk slipknot, an occlusion of the left anterior descending coronary artery was performed. Visual blanching and electrocardiographic changes confirmed myocardial ischemia. In Sham animals, suture was not ligated. After 30 minutes, the suture occlusion was released. Celastrol, Celastrol analogs or vehicle was injected intraventricularly for acute systemic delivery, then the chest was closed. Buprenorfine (0.05 mg/Kg sc) and carprofen (5 mg/Kg sc) were Injected at the end of surgery. Animals were left to recuperate for 24 h, then a second echocardiography was performed. Animals were sacrificed, cardiac tissue was snap frozen, and blood was collected in heparinized tubes, then centrifuged at 4° C. Plasma was collected, snap frozen and kept at −80° C. until analysis.

Figure 34:
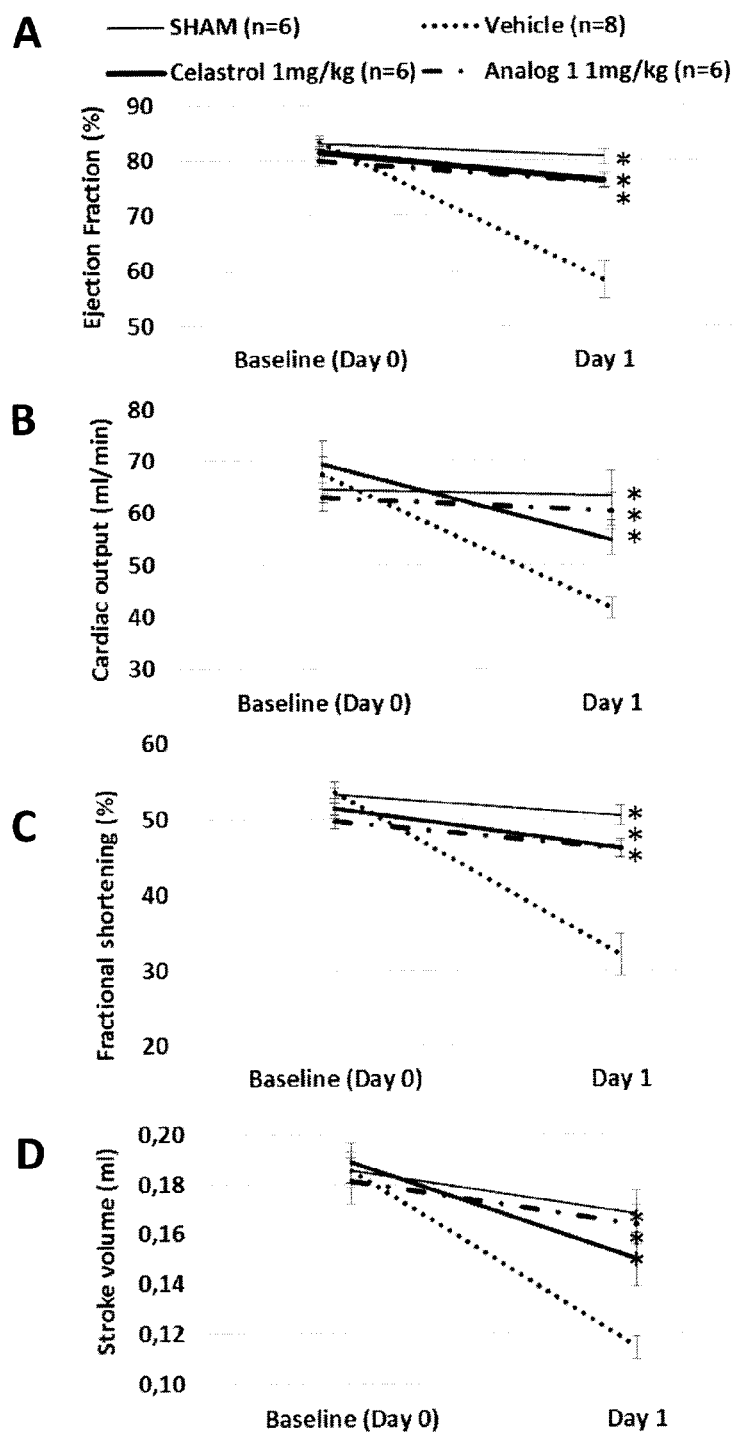
FIG. 34 A to D indicate Celastrol (1 mg/Kg) and Analog 1 (1 mg/Kg) protect cardiac function following I/R injury by preserving A) ejection fraction (EF), B) cardiac output (CO), C) fractional shortening (FS) and D) stroke volume (SV) compared to Vehicle (DMSO) treated animals.
Figure 36:
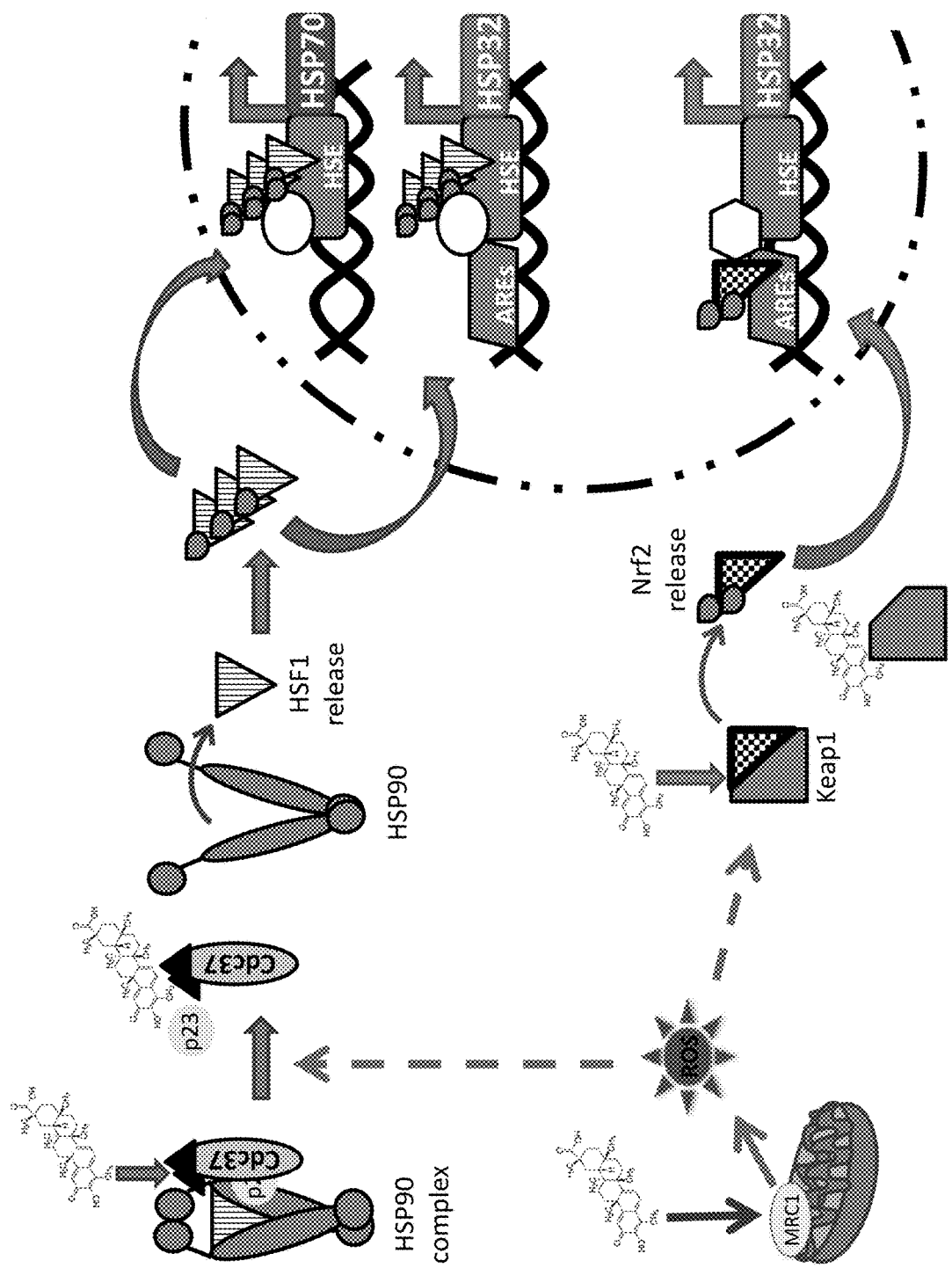
FIG. 36 is a schematic diagram showing Celastrol's proposed mechanisms of induction of HSR and AR, leading to upregulation of cytoprotective genes.

Results of FIG. 34 indicate Celastrol (1 mg/Kg) and Analog 1 (1 mg/Kg) protect cardiac function following I/R injury by preserving A) ejection fraction (EF), B) cardiac output (CO), C) fractional shortening (FS) and D) stroke volume (SV) compared to Vehicle (DMSO) treated animals, and these in vivo protective effects of Celastrol were related to a significant Increase in tissue expression of cardioprotective HSP70 and HO-1.

Statistical Analyses

Data are expressed as mean t standard error or median with 95% confidence interval. ANOVA test was used for group comparison of non-repeated measurements. For repeated measurements, linear mixed-effect models were used to compare groups (MIXED procedures in SAS software, version 9.3; SAS Institute, Cary, NC, USA). Between-group differences were assessed. For non-normally distributed measurements, such as indexes and ratios, a log transformation of the measurements was used. For hemodynamic measurements, as much as 200 measurement per rats per time points were used in the model, with each single measurement weighted accordingly (i.e. 1/200). For all analyses. P<0.05 was considered statistically significant.

Example 13: Celastrol and Celastrol analogs modulate expression of genes under the control of HSR and ARE elements H9c2 rat cardiomyoblasts were seeded at a density of 5,000 cells per well in 96 well plates in DMEM 10% FBS complete medium and transfected using lipofectamine with the Cignal Reporter Assay Heat shock response and Antioxidant response kits (SABiosciences, Qiagen) according to the manufacturers' protocol. The next day, Celastrol, analogs and various other compounds were added to the wells in triplicate at a dose range of 10E-5 to 10E-10M in DMEM 1% FBS media for 4 hours followed by 3 hours of washout period complete media prior to measuring the signaling activity using the Dual Luciferase Assay (Promega) The results summarized in FIG. 35 show that Celastrol (Celastrol 1c: purchased from commercial source; Celastrol 2 and 3 used to generate synthetic analogs), and Celastrol analogs Analog 1, Analog 3, and Analog 4, are among the most potent and efficient compounds tested to stimulate the expression of reporter genes controlled in part by heath shock responsive elements (HSR) or antioxidant responsive elements (ARE).

Although the present invention has been described hereinabove by way of specific embodiments thereof, it can be modified, without departing from the spirit and nature of the subject Invention as defined in the appended claims. In the claims, the word "comprising" is used as an open-ended term, substantially equivalent to the phrase "including, but not limited to". The singular forms "a", "an" and "the" include corresponding plural references unless the context clearly dictates otherwise.

What is claimed is:

1. An in vitro or ex vivo method of modulating the state of a cell, a cell preparation, a tissue, a graft or an organ so as to increase resistance to hypoxia reoxygenation stress the method comprising:

contacting the cell, the cell preparation, the tissue, the graft or the organ with:

a) a composition comprising one or more of the following compounds:

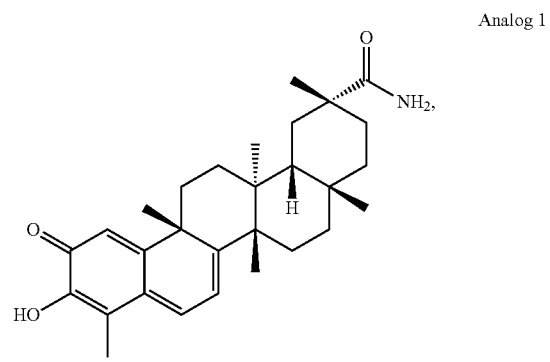

-continued

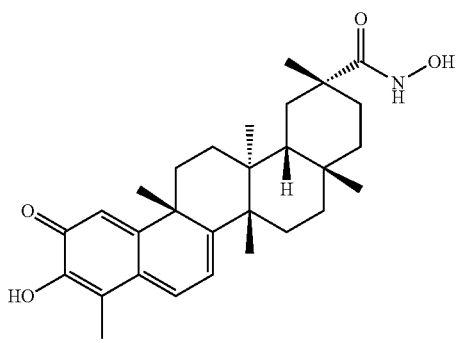
Analog 4 or
a pharmaceutically acceptable salt, a stereoisomer, or a tautomer thereof,
b) a secretome of: a distinct cell preparation that has been contacted with a composition comprising the one or more of the Analog 1, the Analog 2, the Analog 3, and the Analog 4, or a pharmaceutically acceptable salt, a stereoisomer, or a tautomer thereof or with the combination thereof,
wherein the cell or cell preparation is non-cancerous.

2. The method of claim 1, wherein the compound is Analog 1:

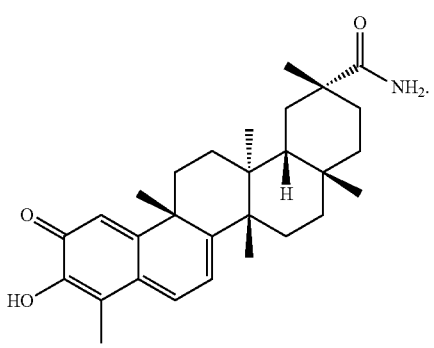
Analog 1

3. The method of claim 1, wherein the compound is Analog 2:

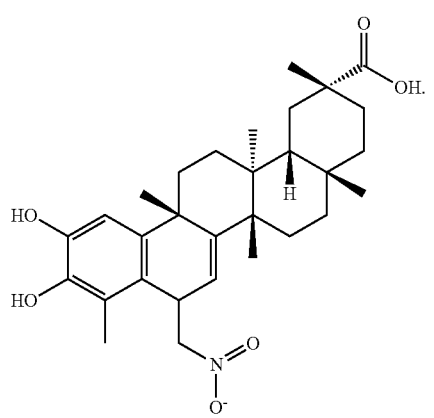
Analog 2

4. The method of claim 1, wherein the compound is Analog 3:

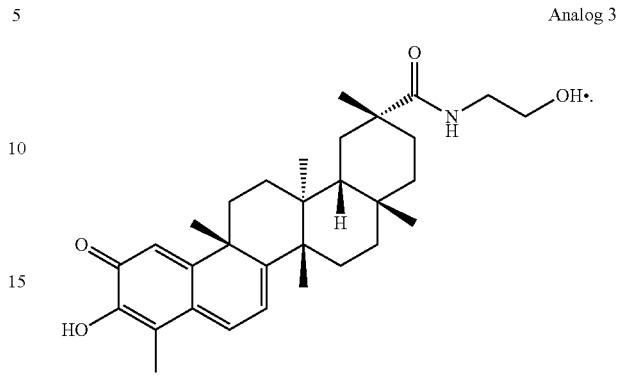
Analog 3

5. The method of claim 1, wherein the compound is Analog 4:

Analog 4

6. The method of claim 1, further comprising contacting the cell, the cell preparation, the tissue, the graft or the organ with: one or more adjunct agent selected from: of tert-butylhydroquinone (tBHQA), bis(2-hydroxybenzylidene) acetone (2HBA), epigallocatechin gallate (EGCG), carnosol, curcumin, ascorbic acid, melatonin, edaravone and andrographolide.

7. The method of claim 1, wherein the cell, tissue, graft or organ is suitable for transplantation in a mammal.

8. The method of claim 7, wherein the mammal suffers from or is susceptible of suffering from an ischemic disease or degenerative disease.

9. The method of claim 8, wherein the ischemic disease is stroke, myocardial infarction (MI), peripheral arterial disease (PAD), transient ischemic attack, microangiopathy, brain ischemia, bowel ischemia, liver ischemia, pulmonary ischemia, renal ischemia, or vascular dementia.

10. The method of claim 1, wherein the method is performed in vitro on cells prior to freezing or during conditioning.

11. The method of claim 1, wherein the cells or the cell preparation comprises stem cells.

12. The method of claim 11, wherein the stem cells are mesenchymal stem cells, CD34+ cells, CD133+ cells, pluripotent, induced pluripotent stem cells, hematopoietic stem cells or progenitor cells.

13. The method of claim 11, wherein the stem cells are autologous stem cells isolated from a mammal in need.

14. The method of claim 11, wherein the stem cells are allogenic stem cells isolated from a mammal donor.

15. The method of claim 14, wherein the allogenic stem cells from the mammal donor is HLA-typed matched, immune-privileged, hypoimmunogenic or immune-evasive with the a mammal in need.

16. The method of claim 1, wherein the method is performed in vitro.

17. The method of claim 16, wherein the method is performed during ex vivo organ perfusion.

18. The method of claim 17, wherein the organ is a heart, kidney, liver or lung.

19. The method of claim 1, wherein the method further comprises transplanting the cell, cell preparation, tissue, graft or organ into a subject in need thereof.

20. A method of transplanting cells, a tissue, a graft or an organ, the method comprising:
contacting the cells, tissue, graft or organ with:
a) a composition comprising one or more of the following compounds:

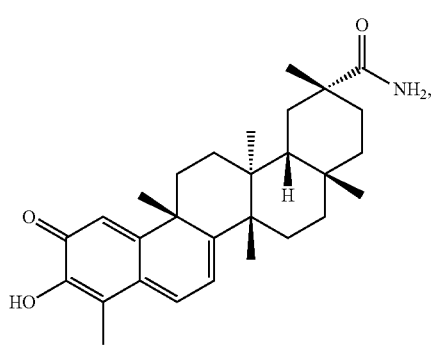

Analog 1

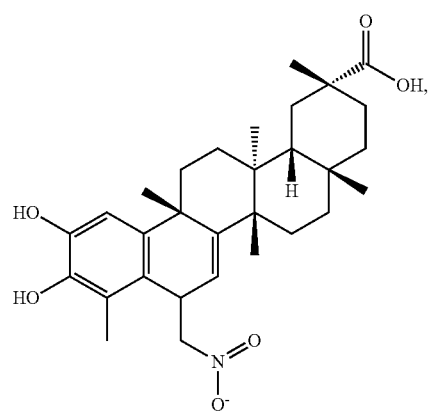

Analog 2

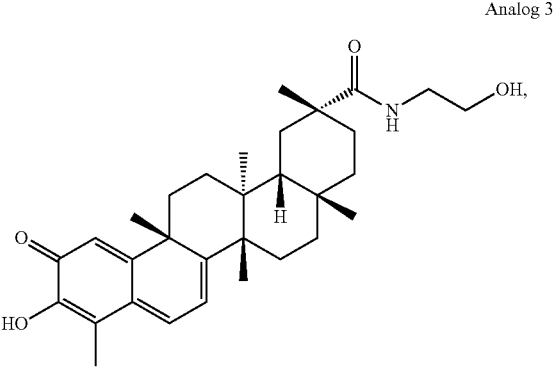

Analog 3

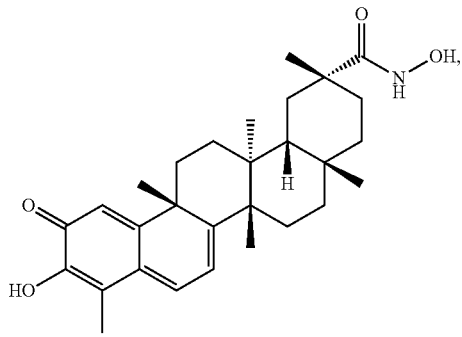

Analog 4 or
a pharmaceutically acceptable salt, a stereoisomer, or a tautomer thereof,
b) a secretome of a distinct cell preparation that has been contacted with a composition comprising the one or more of the Analog 1, the Analog 2, the Analog 3, the Analog 4, or a pharmaceutically acceptable salt, a stereoisomer, or a tautomer or a pro drug thereof or with the combination thereof, wherein the cells, tissue, graft or organ are contacted with the composition in vitro or ex vivo prior to or during a transplant procedure; and wherein the cells are non-cancerous.

21. The method of claim 1, wherein the compound is contacted at a concentration of $10^{-6}$ to $10^{-10}$ M, and/or wherein the method further comprises washing the cell, cell preparation, tissue, graft or organ after contacting to remove the compound.

22. The method of claim 20, wherein the compound is contacted at a concentration of $10^{-6}$ to $10^{-10}$ M, and/or wherein the method further comprises washing the stem cells, tissue, graft or organ after contacting to remove the compound.

23. The method of claim 1, wherein the method further comprises washing the cell, the cell preparation, the tissue, the graft or the organ and recuperating the cell, the cell preparation, the tissue, the graft or the organ for up to 24 hours after contacting the cell, the cell preparation, the tissue, the graft or the organ with the composition.

24. The method of claim 21, wherein the method further comprises, adding a long-term storage medium, optionally a cryopreservation media.

25. The method of claim 1, wherein the composition is contacted for between 5 minutes to 4 hours.

26. An in vitro or ex vivo method of modulating the state of a cell, a cell preparation, a tissue, a graft or an organ so as to increase resistance to hypoxic stress
the method comprising
contacting the cell, the cell preparation, the tissue, the graft or the organ with:
a) a composition comprising one or more of the following compounds:

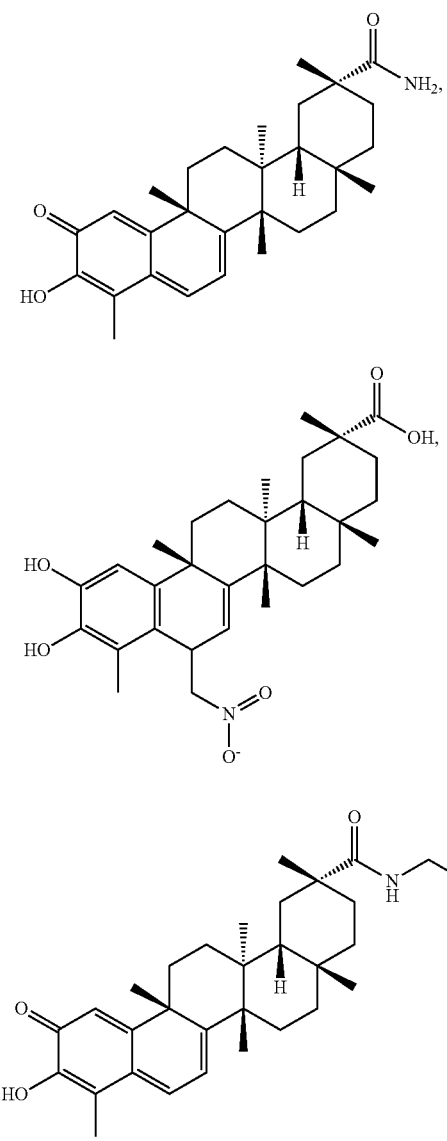

or
a pharmaceutically acceptable salt, a stereoisomer, or a tautomer thereof, b) a secretome of: a distinct cell preparation that has been contacted with a composition comprising the one or more of the Analog 1, the Analog 2, and the Analog 3, or a pharmaceutically acceptable salt, a stereoisomer, or a tautomer thereof or with the combination thereof, wherein the cell or cell preparation is non-cancerous.

27. The method of claim 26, further comprising contacting the cell, the cell preparation, the tissue, the graft or the organ with: one or more adjunct agent selected from: of tert-butylhydroquinone (tBHQ), bis(2-hydroxybenzylidene)acetone (2HBA), epigallocatechin gallate (EGCG), carnosol, curcumin, ascorbic acid, melatonin, edaravone and andrographolide and/or wherein the cell, tissue, graft or organ is suitable for transplantation in a mammal.

28. The method of claim 27, wherein the mammal suffers from or is susceptible of suffering from an ischemic disease or degenerative disease.

29. The method of claim 28, wherein the ischemic disease is stroke, myocardial infarction (MI), peripheral arterial disease (PAD), transient ischemic attack, microangiopathy, brain ischemia, bowel ischemia, liver ischemia, pulmonary ischemia, renal ischemia, or vascular dementia.

30. The method of claim 26, wherein the method is performed in vitro on cells prior to freezing or during conditioning and/or wherein the cells or the cell preparation comprises stem cells.

31. The method of claim 30, wherein the stem cells are mesenchymal stem cells, CD34+ cells, CD133+ cells, pluripotent, induced pluripotent stem cells, hematopoietic stem cells or progenitor cells, wherein the stem cells are autologous stem cells isolated from a mammal in need, or wherein the stem cells are allogenic stem cells isolated from a mammal donor.

32. The method of claim 31, wherein the allogenic stem cells from the mammal donor is HLA-typed matched, immune-privileged, hypoimmunogenic or immune-evasive with the a mammal in need.

33. The method of claim 26, wherein the method is performed in vitro or performed during ex vivo organ perfusion and/or wherein the organ is a heart, kidney, liver or lung.

34. The method of claim 26, wherein the method further comprises transplanting the cell, cell preparation, tissue, graft or organ into a subject in need thereof and/or wherein the composition is contacted for between 5 minutes to 4 hours.

* * * * *